(12) United States Patent
Rausch et al.

(10) Patent No.: US 11,992,481 B2
(45) Date of Patent: May 28, 2024

(54) USE OF 2-SUBSTITUTED INDAZOLES FOR THE TREATMENT AND PROPHYLAXIS OF AUTOIMMUNE DISEASES

(71) Applicant: Bayer Pharma Aktiengesellschaft, Berlin (DE)

(72) Inventors: Alexandra Rausch, Berlin (DE); Stefan Joachim Jodl, Kleinmachnow (DE); Jörn Krätzschmar, Berlin (DE); Ulrich Bothe, Berlin (DE); Nicole Schmidt, Wuppertal (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 17/673,644

(22) Filed: Feb. 16, 2022

(65) Prior Publication Data
US 2022/0249456 A1 Aug. 11, 2022

Related U.S. Application Data

(63) Continuation of application No. 16/863,330, filed on Apr. 30, 2020, now abandoned, which is a
(Continued)

(30) Foreign Application Priority Data

Jun. 1, 2016 (EP) .................................. 16172507

(51) Int. Cl.
*A61K 31/4439* (2006.01)
*A61P 19/02* (2006.01)
(Continued)

(52) U.S. Cl.
CPC .......... *A61K 31/4439* (2013.01); *A61P 19/02* (2018.01); *A61P 29/00* (2018.01); *A61P 37/06* (2018.01)

(58) Field of Classification Search
CPC ...... A61K 31/4439; A61P 19/02; A61P 29/00; A61P 37/06; A61P 37/02; Y02A 50/30
(Continued)

(56) References Cited

U.S. PATENT DOCUMENTS

| 9,951,086 B2 | 4/2018 | Bothe |
| 10,308,634 B2 | 6/2019 | Bothe |

(Continued)

FOREIGN PATENT DOCUMENTS

| EP | 2489663 A1 | 8/2012 |
| WO | 2004011328 A1 | 2/2004 |

(Continued)

OTHER PUBLICATIONS

US 7,979,887 B2, 02/2011, Ohrai (withdrawn)
(Continued)

*Primary Examiner* — Taylor V Oh
(74) *Attorney, Agent, or Firm* — Morrison & Foerster LLP

(57) ABSTRACT

The present application relates to substituted indazoles, to the use thereof alone or in combinations for treatment and/or prophylaxis of autoimmune disorders, and to the use thereof for production of medicaments for treatment and/or prophylaxis of autoimmune disorders, especially for treatment and/or prophylaxis of arthritides (especially psoriatic arthritis, rheumatoid arthritis, Bekhterev's disease, reactive arthritis, systematic juvenile idiopathic arthritis), systematic lupus erythematosus, multiple sclerosis, psoriasis, atopic dermatitis, allergic eczema and chronic-inflammatory bowel disorders (especially Crohn's disease and ulcerative colitis).

12 Claims, 15 Drawing Sheets

Related U.S. Application Data continuation of application No. 16/306,506, filed as application No. PCT/EP2017/062535 on May 24, 2017, now abandoned.

(51) Int. Cl.
*A61P 29/00* (2006.01)
*A61P 37/06* (2006.01)

(58) Field of Classification Search
USPC ...................................................... 514/218
See application file for complete search history.

(56) References Cited

U.S. PATENT DOCUMENTS

| | | |
|---|---|---|
| 10,435,396 B2 | 10/2019 | Bothe |
| 10,501,417 B2 | 12/2019 | Thaler |
| 10,501,437 B2 | 12/2019 | Thaler |
| 10,633,365 B2 | 4/2020 | Thaler |
| 10,759,758 B2 | 9/2020 | Thaler |
| 10,793,545 B2 | 10/2020 | Bothe |
| 2007/0185058 A1 | 8/2007 | Conte et al. |
| 2010/0094000 A1 | 4/2010 | Fukumoto et al. |
| 2016/0311833 A1 | 10/2016 | Bothe et al. |
| 2017/0349570 A1 | 12/2017 | Bothe et al. |
| 2018/0201609 A1 | 7/2018 | Gummadi et al. |
| 2018/0289685 A1 | 10/2018 | Bothe |
| 2019/0388410 A1 | 12/2019 | Bothe |
| 2020/0216413 A1 | 7/2020 | Beddies |
| 2021/0053941 A1 | 2/2021 | Bothe et al. |
| 2022/0241261 A1 | 8/2022 | Bothe et al. |
| 2022/0388982 A1 | 12/2022 | Bothe et al. |
| 2023/0174508 A1 | 6/2023 | Bothe et al. |

FOREIGN PATENT DOCUMENTS

| | | |
|---|---|---|
| WO | 2005082866 A2 | 9/2005 |
| WO | 2005082866 A3 | 4/2006 |
| WO | 2006061715 A2 | 6/2006 |
| WO | 2006061715 A3 | 11/2006 |
| WO | 2006116412 A8 | 3/2007 |
| WO | 2008001883 A1 | 1/2008 |
| WO | 2009117421 A2 | 9/2009 |
| WO | 2009117421 A3 | 1/2010 |
| WO | 2012061926 A1 | 5/2012 |
| WO | 2012107475 A1 | 8/2012 |
| WO | 2012112743 A1 | 8/2012 |
| WO | 2013174744 A1 | 11/2013 |
| WO | 2015091426 A1 | 6/2015 |
| WO | 2015104662 A1 | 7/2015 |
| WO | 2015193846 A1 | 12/2015 |
| WO | 2016083433 A1 | 6/2016 |
| WO | 2016174183 A1 | 11/2016 |
| WO | 2017148902 A1 | 9/2017 |
| WO | 2017157792 A1 | 9/2017 |
| WO | 2017186689 A1 | 11/2017 |
| WO | 2017186693 A1 | 11/2017 |
| WO | 2017186700 A1 | 11/2017 |
| WO | 2017186703 A1 | 11/2017 |
| WO | 2017207481 A1 | 12/2017 |

OTHER PUBLICATIONS

Akash, M.S.H. et al. (2012). "Interleukin-1 Receptor Antagonist: A New Therapy for Type 2 Diabetes Mellitus," Journal of Pharmaceutical Sciences 101(5): 1647-1658.
Araùjo, J.A.P. et al. (2016). "Th17 cells and CD4+ multifunctional T cells in patients with systemic lupus erythematosus," Rev Bras Beumatol 56(1): 28-36.
Ashimori, A. et al. (1990). "Novel 1,4-Dihydropyridine Calcium Antagonists.," Chem. Pharm. Bul.. 38(9): 2446-2458.
Bascherini, V. et al. (2015) "The protean ocular involvement in monogenic autoinflammaroty diseases: state of the art," Clin Rheumatol 34: 1171-1180.
Bendele, A.M. (2001). "Animal models of osteoarthritis," J. Musculoskel Neuron Interact 1(4): 363-376.
Brenner, M. et al. (2009). "Targeted treatment of pyoderma gangrenosum in PAPA (pyogenic arthritis, pyoderma gangrenosum and acne) syndrome with the recombinant human interleukin-1 receptor antagonist anakinra," British Journal of Dermatology 161: 1199-1201.
Brucklacher-Waldert, V. et al. (2009). "Phenotypical and functional characterization of T helper 17 cells in multiple sclerosis," Brain 132: 3329-3341.
Bunting, M.M. et al. (2013). "Interleukin-33 Drives Activation of Alveolar Macrophages and Airway Inflammation in a Mouse Model of Acute Exacerbation of Chronic Asthma," BioMed Research International 10 pages.
Burmester, G.R. et al. (2016). "Tocilizumab in early progressive rheumatoid arthritis: Function, a randomized controlled trial," Ann Rheum Dis 75: 1081-1091.
Byers, D.E. et al. (2013). "Long-term IL-33-producing epithelial progenitor cells in chronic obstructive lung disease," The Journal of Clinical Investigation 123(9): 3967-3982.
Candia, L. et al. (2007). "Toll-like receptor-2 expression is upregulated in antigen-presenting cells from patients with psoriatic arthritis: a pathogenic role for innate immunity," J. Rheumatol 34: 374-379.
Cario, E. (2010). "Toll-like Receptors in Inflammatory Bowel Diseases: A Decade Later," Inflamm Bowel Dis 16(9): 1583-1597.
Carrasco, S. et al. (2011). "Toll-like reception (TLR) 2 is upregulated on peripheral blook monocytes of patients with psoriatic arthritis: a role for a gram-positive inflammatory trigger," Clinical and Experimental Rheumatology 29: 958-962.
Carrier, Y. et al. (2011). "Inter-Regulation of TH17 Cytokines and the IL-36 Cytokines in Vitro and in Vivo: Implications in Psoriasis Pathogenesis," Journal of Investigative Dermatology 131: 2428-2437.
Caso, F. et al. (2014). "Biological Treatments in Behçet's Disease: Beyond Anti-TNF Therapy," Mediators of Inflammation Article ID 107421, 14 pages.
Cevikbas, F. et al. (2012). "IL-33: A Novel Danger Signal System in Atopic Dermatitis," Journal of Investigative Dermatology 132: 1326-1329.
Chang, J.H. et al. (2012). "Recent advances in Toll-like receptors and anterior uveitis," Clinical and Experimental Ophthalmology 40: 821-828.
Chaudhary, D. et al. (2015). "Recent Advances in the Discovery of Small Molecule Inhibitors of Interleukin-1 Receptor-Associate Kinase 4 (IRAK4) as a Therapeutic Target for Inflammation and Oncology Disorders," J. Med. Chem. 58: 96-110.
Chen, D-Y. et al. (2013). "Involvement of TLR7 MyD88-dependent signaling pathway in the pathogenesis of adult-onset Still's disease," Arthritis Research & Therapy 15: 1-12.
Chen, J-Q. et al. (2016). "Toll-Like receptor Pathways in Autoimmune Diseases," Clinic Rev Allerg Immunol 50: 1-17.
Chiang, E.Y. et al. (2011). "Immune Complex-Mediated Cell Activation from Systemic Lupus Erythematosus and Rhematoid Arthritis Patients Elaborate Different Requirement for IRAK1/4 Kinase Activity across Human Cell Types," J Immunol 186: 1279-1288.
Chopra, P. et al. (2013). "Treatment of Complex Regional Pain Syndrome (CRPS) Using Low Dose Naltrexone (LDN)," J Neuroimmune Pharmacol 8: 470-476.
Christensen, S.R. et al. (2006). "Toll-like Receptor 7 and TLR9 Dictate Autoantibody Specificity and Have Opposing Inflammatory and Regulatory Roles in a Murine Model of Lupus," Immunity 25: 417-428.
Ciccia, F. et al. (2015). "Difference in the expression of IL-9 and IL-17 correlates with different histological pattern of vascular wall injury in gian cell arteritis," Rheumatology 54: 1596-1604.
Cinetto, F. et al. (2016). "Advances in understanding the immunopathology of sarcoidosis and implications on therapy," Expert Review of Clinical Immunology 12(9): 973-988.
Coccia, M. et al. (2012). "IL-1β mediates chronic intestinal inflammation by promoting the accumulation of IL-17A secreting innate lymphoid cells and CD4+ Th17 cells," J. Exp. Med. 209(9): 1595-1609.

(56) References Cited

OTHER PUBLICATIONS

Cordiglieri, C. et al. (2014). "Innate immunity in myasthenia gravis thymus: Pathogenic effects of Toll-like receptor 4 signaling on autoimmunity," Journal of Autoimmunity 52: 74-89.
Cottet, F. et al. (2002). "Trifluoromethyl-Substituted Pyridines Through Displacement of Iodine by in situ Generated (Trifluoromethyle)copper," Eur. J. Org. Chem. 2: 327-330.
Cottet, F. et al. (2003). "Recommendable Routes to Trifluoromethyl-Substituted Pyridine- and Quinolinecarboxylic Acids," Eur. J Org Chem. 8: 1559-1568.
Cottet, F. et al. (2004). "Logistic flexibility in the preparation of isomeric halopyridinecarboxylic acids," Tetrahedron 60: 11869-11874.
Cottet, F. et al. (2004). "Futher Metalations and Funcionalizations of Chloro-, Bromo- and Iodo(trifluoromethyl) pyridines," Synthesis 10: 1619-1624.
Couillin, I. et al. (2009). "IL-1R1/MyD88 Signaling in Critical for Elastase-Induced Lung Inflammation and Emphysema," J Immunol 183: 8195-8202.
Crow, M.K. (Feb. 2010). "Interferon-alpha: a therapeutic target in systemic lupus erythematosus," Rheim Dis Clin North Am. 36(1): 173-x.
D'Elia, E. et al. (2015). "Successful treatmeant of subacute constrictive pericarditis with interleukin-1β receptor antagonist (anakinra)," Rheumatol, 294-295.
Damasio (1996). "Alzheimer's Disease and Related Dementias," Cecil Textbook of Medicine, 20th Edition, vol. 2, pp. 1992-1996.
Dasu, M.R. et al. (2012). "Toll-like receptors and diabetes: a therapeutic perspective," Clinical Science 122: 203-214.
Datta, S. et al. (2004). "Toll IL-1 Receptors Differ in Their Ability to Promote the Stabilization of Adenosine and Uridine-Rich Elements Containing mRNA," J Immunol 173: 2755-2761.
David, B.T. et al. (2013). "A toll-like receptor 9 antagonist reduces pain hypersensitivity and the inflammatory response in spinal cord injury," Neurobiology of Disease 54: 194-205.
Davidson, D.J. et al. (2006). "IRAK-4 Mutation (Q293X): Rapid Detection and Characterization of Defective Post-Transcriptional TLR/IL-1R Responses in Human Myeloid and Non-Myeloid Cells," J. Immunol 177: 8202-8211.
Davies, R.R. (1955). "Indazole Derivatives: The Synthesis of Various Amino- and Hydroxy-indazoles and Derived Sulphonic Acids," Journal of the Chemical Society, 2412-2419.
De Koning, H.D. (2014). "Schnitzler's syndrome: lessons from 281 cases," Clinical and Translational Allergy 4(41): 1-15.
Del Rey, A. et al. (2012). "Chronic neuropathic pain-like behavior and brain-borne IL-1β," Ann. N.Y. Acad. Sci. 1262: 101-107.
Deng, J. et al. (Feb. 27, 2009). "TLR4 and TLR5 induce distinct types of vasculitis," Circ Res. 104(4): 488-195.
Deng, Y. et al. (2016). "The Inflammatory Response in Psoriasis: a Comprehensive Review," Clin Rev Allergy Immunol. 50: 377-389.
Dermer, G.B. (Mar. 12, 1994). "Another Anniversary for the War on Cancer," Bio/Technology 12:320.
Devaraj, S. et al. (Aug. 31, 2011). "Knockout of Toll-like Receptor-2 attenuates both the Pro-Inflammatory State of Diabetes and Incipient Diabetic Nephropathy," Arterioscler Thromb Vase Biol. 31(8): 1796-1804.
Dieleman, L.A. et al. (1994). "Dextran Sulfate Sodium-Induced Colitis Occurs in Severe Combined Immunodeficient Mice," Gastroenterol 107: 1643-1652.
Dinarello, C.A. (2009). "Immunological and Inflammatory Functions of the Interleukin-1 Family," Annu. Rev. Immunol. 27:519-550.
Dinarello, C.A. (2011). "A clinical perspective of IL-1β as the gatekeeper of inflammation," Eur. J. Immunol. 41: 1203-1217.
Dispenza, M.C. et al. (2012). "Systemic isotretinoin therapy normalizes exaggerated TLF-2-mediated innate immune responses in acne patients," J. Invest Dermatol. 132(9): 2198-2205.
Esendagli, G. et al. (2013). "Evaluation of Th 17-related cytokines and receptor in multiple sclerosis patients under interferon beta-1 therapy," Journal of Neuroimmunology 225: 81-84.

Ferraccioli, G. et al. (Nov.-Dec. 2010). "Interleukin-1β and Interleukin-6 in Arthritis Animal Models: Roles in the Early Phase of Transition from Acute to Chronic Inflammation and Relevance for Human Rheumatoid Arthritis," Mol Med 16(11-12): 552-557.
Firinu, D. et al. (2016). "SAPHO Syndrome: Current Developments and Approaches to Clinical Treatment," Curr Rheumatol Rep 18: 35.
Fischer, S. et al. (2003). "Atopisches Ekzem," Hautarzt 54: 914-924.
Flannery, S. et al. (2010). "The interleukin-1 receptor-associated kinases: Critical regulators of innate immune signalling," Biochemical Pharmacology 80:1981-1991.
Foster, A.M. et al. (2014). "IL-36 promotes myeloid cell infiltration, activation and inflammatory activity in skin," J Immunol. 192(12): 6053-6061.
Freshney, R.I. et al. (1983). "Culture of Animal Cells," Chapter 1 in a Manual of Basic Technique, Alan R. Liss, Inc., New York, NY, pp. 1-6.
Fresno, M. et al. (2011). "Toll-like receptors, inflammation, metabolism and obesity," Archives of Physiology and Biochemistry 117(3): 151-164.
Fujino, S. et al. (2003). "Increased expression of interleukin 17 in inflammatory bowel disease," Gut 52: 65-70.
Furst, D.E. et al. (2014). "Rheumatoid arthritis pathophysiology: update on emerging cytokine and cytokine-associated cell targets," Rheumatology 53: 1560-1596.
Gadakh, A.V. et al. (2012). "Heteroaryl Hydroxycarbonylation: An efficient, robust, practically scalable approach using formyl acetate as the co source," Synthetic Communications 42: 658-666.
Gambuzza, M. et al. (2011). "Targeting Toll-like receptors: Emerging therapeutics from multiple sclerosis management," Journal of Neuroimmunology 239: 1-12.
Gerdes, H. et al. (1980). "3-Oxatricyclo[5.3.1.01,4]undec-4-en, ein stark gespannter Vierring-Enolether," 3. Chemische Berichte 113: 1907-1920 (Abstract Only).
Geremia, A. et al (2014). "Innate and adaptive immunity in inflammatory bowel disease," Autoimmunity Reviews 13: 3-10.
Geremia, A. et al. (2012). "The IL-23/IL-17 pathway in inflammatory bowel disease," Expert Reviews 6(2): 223-237.
Gilliet, M. et al. (2004). "Psoriasis Triggered by Toll-like Receptor 7 Agonist Imiquimod in the Presence of Dermal Plasmacytoid Dendritic Cell Precursors," Arch Dermatol 140: 1490-1495.
Goh, F.G. et al. (2012). "Intrinsic danger: activation of Toll-like receptors in rheumatoid arthritis," Rheumatology 51: 7-23.
Gresnigt, M.S. et al. (2013). "Biology of IL-36 cytokines and their role in disease," Seminars in Immunology 25: 458-465.
Guerrero, A.T.G. et al. (2012). "Toll-like receptor 2/MyD88 signaling mediates zymosan-induced joint hypernociception in mice: Participation of TNF-β, IL-1β and CXCL1/KC," European Journal of Pharmacology 674: 51-57.
Gura, T. (1997). "Systems for Identifying New Drugs Are Often Faulty," Science 278(5340):1041-1042, , 5 pages.
Gül, A. et al. (2012). "Interleukin-1β-regulating antibody XOMA 052 (gevokizumab) in the treatment of acute exacerbations of resistant uveitis of Behçet's disease: an open-label pilot study," Ann Rheum Dis 71:563-566.
Haenuki, Y. et al. (2012). "A critical role of IL-33 in experimental allergic rhinitis," J Allergy Clin Immunol 130(1): 184-194.
Hagberg, N. et al. (2015). "Systemic Lupus Erythematosus—A Disease with a Dysregulated Type I Interferon System," Scandinavian Journal of Immunology 82: 199-207.
Hao, L-Y. et al. (2013). "Inflammasomes in inflammatory bowel disease pathogenesis," Current Opinion 29(4): 363-369.
Heimesaat, M.M. et al. (2007). "Shift Towards Pro-inflammatory Intestinal Bacteria Aggravates Acute Murine Colitis via Toll-like Receptors 2 and 4," PLoS One 7: 1-7.
Heimesaat, M.M. et al. (2010). "MyD88/TLR9 mediated immunopathology and gut microbiota dynamics in a novel murine model of intestinal graft-versus-host disease," Gut 59: 1079-1087.
Henderson, C. et al. (2010). "Monogenic IL-1 Mediated Autoinflammatory and Immunodeficiency Syndromes: Finding the Right Balance in Response to Danger Signals," Clin Immunol. 135(2): 210-222.

(56) References Cited

OTHER PUBLICATIONS

Hoffmann, R. (Dec. 1999). "The Potential Role of Cytokines and T Cells in Alopecia Areata," Journal of Investigative Dermatology Symposium Proceedings 4(3): 235-238.

Holmdahl, R. et al. (1989). "Collagen induced arthritis as an experimental model for rheumatoid arthritis," APMIS 97: 575-584.

Holtmann, H. et al. (2001). "The MAPK Kinase Kinase TAK1 Plays a Central Role in Coupling the Interleukin-1 Receptor to Both Transcriptional and RNA-targeted Mechanisms of Gene Regulation," The Journal of Biological Chemistry 276(5): 3508-3516.

Imaoka, H. et al. (2008). "Interleukin-18 production and pulmonary function in COPD," Eur Respir J. 31: 287-297.

Isailovic, N. et al. (2015). "Interleukin-17 and innate immunity in infections and chronic inflammation," Journal of Autoimmunity 60: 1-11.

Jain, S. et al. (2015). "Effectiveness and Safety of Anakinra for Management of Refractory Pericarditis," The American Journal of Cardiology 116: 1277-1279.

Janeway, C.A. et al. (2002). "Innate Immune Recognition," Annu. Rev. Immunol. 20:197-216.

Jialal, I. et al. (2014). "Global toll-like receptor 4 knockout results in decreased renal inflammation, fibrosis and podocytophathy," Journal of Diabetes and Its Complications 28: 755-761.

Johnson, J. et al. (2001). "Relationships between drug activity in NCI preclinical in vitro and in vivo models and early clinical trials," British Journal of Cancer 84(10): 1424-1431.

Kaesler, S. et al. (2014). "Toll-like receptor 2 ligands promote chronic atopic dermatitis through IL-4-mediated suppression of IL-10," J. Allergy Clin Immunol 134(1): 92-99.

Kang, M-J. et al. (2007). "IL-18 is Inducted and IL-18 Receptor $\alpha$ Plays a Critical Role in the Pathogenesis of Cigarette Smoke-Induced Pulmonary Emphysema and Inflammation," J Immunol 178: 1948-1959.

Kaplan, M. et al. (2014). "Effectiveness of interleukin-1 receptor antagonist (Anakinra) on cerulean-induced experimental acute pancreatitis in rats," Scandinavian Journal of Gastroenterology 49: 1124-1130.

Kawayama, T. et al. (2012). "Interleukin-18 in Pulmonary Inflammatory Diseases," Journal of Interferon & Cytokine Research 32(10): 443-451.

Kezic, J. et al. (2011). "Endotoxin-induced uveitis is primarily dependent on radiation-resistant cells and on MyD88 but not TRIF," Journal of Leukocyte Biology 90(2): 305-311.

Kim, D. et al. (2009). "Toll-Like Receptors in Peripheral Nerve Injury and Neuropathic Pain," Current Topics in Microbiology and Immunology 336: 169-186.

Kim, G-T et al. (2010). "Expression of TLR2, TLR4, and TLR9 in dermatomyositis and polymyositis," Clin Rheumatol 29: 273-279.

Kim, T.W. et al. (2007). "A critical role for IRAK4 kinase activity in Toll-like receptor-mediated innate immunity," JEM 204(5):1025-1036.

Kobayashi, T. et al. (2008). "IL23 differentially regulates the Th1/Th17 balance in ulcerative colitis and Crohn's disease," Gut 57: 1982-1689.

Kobori, A. et al. (2010). "Interleukin-33 expression is specifically enhanced in inflamed mucosa of ulcerative colitis," J. Gastroenterol 45: 999-1007.

Kollewe, C. et al. (2004). "Sequential Autophosphorylation Steps in the Interleukin-1 Receptor-associated Kinase-1 Regulate its Availability as an Adapter in Interleukin-1 Signaling," The Journal of Biological Chemistry 279(7): 5227-5236.

Kreisel, D. et al. (2013). "Innate immunity and organ transplantation: focus on lung transplantation," Transpl Int. 26 (1): 2-10.

Ku, C. et al. (2007). "Selective predisposition to bacterial infections in IRAK-4-deficient children: IRAK-4-dependent TLRs are otherwise redundant in protective immunity," JEM 204(10):2407-2422.

Kwok, Y.H. et al. (2012). "Increased Responsiveness of Peripheral Blood Mononuclear Cells to in Vitro TLF 2, 4 and 7 Ligand Stimulation in Chronic Pain Patients," PLOS One 7(8): 1-8.

Layzer (1996). "Degenerative Diseases of the Nervous System," Cecil Textbook of Medicine, 20th Edition, vol. 2, pp. 2050-2057.

Lee, B. et al. (2015). "Angelica gigas ameliorate depression-like symptoms in rats following chronic corticosterone injection," BMC Complementary and Alternative Medicine 15: 210.

Leiss, H. et al. (2013). "Pristane-induced lupus as a model of human lupus arthritis: evolvement of autoantibodies, internal organ and joint inflammation," Lupus 22: 778-792.

Leonardi, S. et al. (Jan.-Feb. 2015). "Serum interleukin 17, interleukin 23, and interleukin 10 values in children with atopic eczema/dermatitis syndrome (AEDS): Association with clinical severity and phenotype," Allergy and Asthma Proceedings 36(1): 74-81.

Leuenberger, M. et al. (2016). "PASS Syndrome: An IL-1-Driven Autoinflammatory Disease," Dermatology 232: 254-258.

Leventhal, J.S. et al. (2012). "Toll-like receptors in transplantation: sensing and reacting to injury," Kidney International 81: 826-832.

Li, D. et al. (2014). "IL-33 promotes ST2-dependent lung fibrosis by the induction of alternatively activated macrophages and innate lymphoid cells in mice," J. Allergy Clin Immunol 134(6): 1422-1432.e11.

Li, J. et al. (2013). "Toll-like receptors as therapeutic targets for autoimmune connective tissue diseases," Pharmacology & Therapeutics 138: 441-451.

Li, M. et al. (2009). "The Critical Role of Toll-Like Receptor Signaling Pathways in the Induction and Progression of Autoimmune Diseases," Current Molecular Medicine 9: 365-374.

Li, X-L. et al. (Jun. 2013). "Elevated Serum Level of IL-33 and sST2 in Patients With Ankylosing Spondylitis: Associated With Disease Activity and Vascular Endothelial Growth Factor," Journal of Investigative Medicine 61(5): 848-851.

Li, X. (2015). "Protective effect of neutralizing anti-IL-18$\alpha$ monoclonal antibody on a mouse model of acute graft-versus-host disease," Oncology Reports 34: 2031-2039.

Li, X. et al. (2008). "IRAK4 in TLR/IL-1R signaling: Possible clinical applications," Eur. J. Immunol. 38: 614-618.

Li, Y. et al. (2011). "Increased memory Th17 cells in patients with neuromyelitis optica and multiple sclerosis," Journal of Neuroimmunology 234: 155-160.

Liu, T. et al. (2013). "New insights into the mechanisms of itch: are pain and itch controlled by distinct mechanisms?" Pflugers Arch. 465(12): 1-24.

Liu, Y. et al. (2013). "Epigenetics in Immune-Mediated Pulmonary Diseases," Clinic Rev Allerg Immunol 45: 314-330.

Liu-Bryan, R. et al. (2005). "Innate Immunity Conferred by Toll-like Receptors 2 and 4 and Myeloid Differentiation Factor 88 Expression Is Pivotal to Monosodium Urate Monohydrate Crystal-Induced Inflammation," Arthritis & Rheumatism 52(9): 2936-2946.

Lloyd, C.M. et al. (2010). "IL-33 family members and asthma—bridging innate and adaptive immune responses," Curr Opin Immunol 22(6): 800-806.

Lock, C. et al. (May 2002). "Gene-microarray analysis of multiple sclerosis lesions yields new targets validated in autoimmune encephalomyelitis," Nature Medicine 8(5): 500-508.

Lubberts, E. et al. (Jul. 2015). "The IL-23-IL-17 axis in inflammatory arthritis," Nature Reviews 11: 415-430.

Lugrin, J. et al. (2015). "Cutting Edge: IL-1$\alpha$ Is a Crucial Danger Signal Triggering Acute Myocardial Inflammation during Myocardial Infarction," The Journal of Immunology 194: 499-503.

Lyn-Cook, B.D. et al. (2014). "Increased expression of Toll-like receptors (TLRs) 7 and 9 and other cytokines in systemic lupus erythematosus (SLE) patients: Ethnic differences and potential new targets for therapeutic drugs," Molecular Immunology 61: 38-43.

Malajian, D. et al. (2015). "New pathogenic and therapeutic paradigms in atopic dermatitis," Cytokine 73: 311-318.

Malkov, A.V. et al. (2003). "A long-range chiral relay via tertiary amide group in asymmetric catalysis: new amino acid-derived N,P-ligands for copper-catalyzed conjugate addition," Chem Commun, 1948-1949.

Marinoni, B. et al. (2014). "The Th17 axis in psoriatic disease: pathogenetic and therapeutic implications," Autoimmun Highlights 5: 9-19.

Martínez-González, I. et al. (2013). "Human Mesenchymal Stem Cells Overexpressing the IL-33 Antagonist Soluble IL-1 Receptor-

(56) References Cited

OTHER PUBLICATIONS

Like-1 Attenuate Endotoxin-Induced Acute Lung Injury," Am J Respir Cell Mol Biol 49(4): 552-562.

Mathian, A. et al. (Nov. 2011). "Factor Influencing the Efficacy of Two Injections of a Pandemic 2009 INfluenze A (H1N1) Nonadjuvanted Vaccine in Systemic Lupus Erythematosus," Arthritis & Rheumatism 63(11): 3502-3511.

McCann, F. E. et al. (2010). "Apremilast, a novel PDE4 inhibitor, inhibits spontaneous production of tumour necrosis factor-alpha from human rheumatoid synovial cells and ameliorates experimental arthritis," Arthritis Research & Therapy 12: R107.

McGettrick, A.F. et al. (2007). "Toll-like receptors: key activators of leucocytes and regulator of haematopoiesis," British Journal of Haematology 139: 185-193.

McInnes, I. B. et al. (Dec. 8, 2011). "The Pathogenesis of Rheumatoid Arthritis," The New England Journal of Medicine 365(23): 2205-2219.

McKenzie, A.N.J. et al. (Dec. 2014). "Type-2 Innate Lymphoid Cells in Asthma and Allergy," AnnalsATS 11(5) S263-S270.

Miller, L.S. (2008). "Toll-like receptors in skin," Adv Dermatol. 24: 71-87.

Minkis, K. et al. (2012). "Interleukin 1 Receptor Antagonist Deficiency Presenting as Infantile Pustulosis Mimicking Infantile Pustular Psoriasis," Arch Dermatol. 148(6): 747-752.

Moco, S. et al. (2007). "Metabolomics technologies and metabolite identification," Trends in Analytical Chemistry, 26(9): 855-866.

Morytko, M. et al. (2008). "Synthesis and in vitro activity of N1-cyano-4-(2-phenylacetyl)-N-o-tolylpiperzaine-1-carboximidamide P2X7 antagonists," Bioorganic & Medicinal Chemistry Letters 18: 2093-2096.

Motshwene, P.G. et al. (2009). "An Oligomeric Signaling Platform Formed by the Toll-like Receptor Signal Transducers MyD88 and IRAK-4," The Journal of Biological Chemistry 284(37):25404-25411.

Márquez, A. et al. (2014). "Influence of the IL17A locus in giant cell arteritis susceptibility," Ann Rheum Dis 73: 1742-1745.

Nakanishi, W. et al. (2013). "IL-33, but Not IL-25, Is Crucial for the Development of House Dust Mite Antigen-Induced Allergic Rhinitis," PLoS One 8(10): 1-8.

Narayanan, S. et al. (2008). "Interleukin-1 Receptor-1-deficient Mice Show Attenuated Production of Ocular Surface Inflammatory Cytokines in Experimental Dry Eye," Cornea 27(7): 811-817.

Nickerson, K.M. et al. (2010). "TLR9 Regulates TLR7- and MyD88-Dependent Autoantibody Production and Disease in a Murine Model of Lupus," J Immunol 184: 1840-1848.

Nicotra, L. et al. (2012). "Toll-Like Receptors in Chronic Pain," Exp Neurol. 234(2): 316-329.

Niebuhr, M. et al. (2008). "Dysregulation of toll-like receptor-2 (TLR-2)-induced effects in monocytes from patients with atopic dermatitis: impact of the TLR-2 R753Q polymorphism," Allergy 63: 728-734.

Nordström, D. et al. (2012). "Beneficial Effect of Interleukin 1 Inhibition with Anakinra in Adult-onset Still's Disease. An Open, Randomized, Multicenter Study," The Journal of Rheumatology 39(10): 2008-2011.

Nygaard, U. et al. (2016). "TSLP, IL-31, IL-33 and sST2 are new biomarkers in endophenotypic profiling of adult and childhood atopic dermatitis," JEADV 30: 1930-1938.

O'Hara, F. et al. (2013). "Radical-Based Regioselective C-H Functionalization of Electron-Deficient Heteroarenes: Scope, Tunability, and Predicatbility," J Am Chem Soc. 135(32): 12122-12134.

Okayasu, I et al. (1990). "A Novel Method in the Induction of Reliable Experimental Acute and Chronic Ulcerative Colitis in Mice," Gastroenterology 98: 694-702.

Okiyama, N. et al. (Nov. 2012). "T Lymphocytes and Muscle Condition Act Like Seeds and Soil in a Murine Polymyositis Model," Arthritis & Rheumatism 64(11): 3741-3749.

Omenetti, A. et al. (2016). "Disease activity accounts for long-term efficacy of IL-1 blockers in pyogenic sterile arthritis pyoderma gangresnosum and severe acne syndrome," Rheumatology 55: 1325-1335.

Ouziel, R. et al. (Jun. 2012). "The ST2 Pathway Is Involved in Acute Pancreatitis," The American Journal of Pathology 180(6): 2330-2339.

Panzer, R. et al. (2014). "TLR2 and TLR4 expression in atopic dermatitis, contact dermatitis and psoriasis," Experimental Dermatology 23: 345-368.

Park, H.J. et al. (Jan. 2014). "Toll-like receptor signaling regulates cisplatin-induced mechanical allodynia in mice," Cancer Chemother Pharmacol. 73(1): 25-34.

Paul, W.E. (Sep. 2015). "History of Interleukin-4," Cytokine 75(1): 3-7.

Pauwels, N.S. et al. (2011). "Role of IL-1α and the Nlrp3/caspase-1/IL-1β axis in cigarette smoke-induced pulmonary inflammation and COPD," European Respiratory Journal 38(5): 1019-1028.

Pearce, H. et al. (2008). "Failure Modes in Anticancer Drug Discovery and Development," Cancer Drug Design and Discovery, ed. Stephen Neidle, Chapter 18, 424-435.

Pettersson, T. et al. (2012). "Setting up TRAPS," Annals of Medicine 44: 109-118.

Piggott, D.A. et al. (Feb. 2005). "MyD88-dependent induction of allergic Th2 responses to intranasal antigen," The Journal of Clinical Investigation 115(2): 459-467.

Price, E.W. et al. (2014). "Modular syntheses of H4octapa and H2dedpa, and yttrium coordination chemistry relevant to 86Y/90Y radiopharmaceuticlas," Dalton Transactions 43: 7176-7190.

Qiu, C. et al. (2013). "Anti-interleukin-33 inhibits cigarette smoke-induced lung inflammation in mice," Immunology 138: 76-82.

Rakoff-Nahoum, S. et al. (2006). "Role of Toll-like Receptors in Spontaneous Commensal-Dependent Colitis," Immunity 25: 319-329.

Ramirez, S.R. et al. (2012). "Toll-like Receptors and Diabetes Complications: Recent Advances," Current Diabetes Reviews 8: 480-488.

Raychaudhuri, S. et al. (2015). "Role of IL-17 in the pathogenesis of psoriatic arthritis and axial spondyoarthritis," Clin Rheumatol 34: 1019-1023.

Redfern, R. L. et al. (2010). "Toll-like receptors in ocular surface disease," Experimental Eye Research 90: 679-687.

Ritchlin, C. T. et al. (May 2016). "New therapies for psoriasis and psoriatic arthritis," Current Opinion 28(3): 204-210.

Roger, T. et al. (Feb. 17, 2009). "Protection from lethal Gram-negative bacterial sepsis by targeting Toll-like receptor 4," PNAS 106(7): 2348-2352.

Rovedatti, L. et al. (2009). "Differential regulation of interleukin 17 and interferon γ production in inflammatory bowel disease," Gut 58: 1629-1636.

Ruperto, N. et al. (2012). "Two Randomized Trials of Canakinumab in Systemic Juvenile Idiopathic Arthritis," The New England Journal of Medicine 367(25): 2396-2406.

Ryu, H.C. et al. (2014). "2-Alkyl/alkeyl substituted pyridine C-region analogues of 2-(3-fluoro-4-methylsulfonylaminophenyl)propanamides as highly potent TRPV1 antagonists," Bioorganic & Medicinal Chemistry Letters 24:4039-4043.

Röse, L. et al. (2012). "Extended DNFB-induced contact hypersensitivity models display characteristics of chronic inflammatory dermatoses," Experimental Dermatology 21: 25-31.

Saluja, R. et al. (2015). "The role of IL-33 and mast cells in allergy and inflammation," Clinical and Translational Allergy 5(33): 1-8.

Saluja, R. et al. (2015). "The role of the IL-33/IL-1RL1 axis in mast cell and basophil activation in allergic disorders," Molecular Immunology 63: 80-85.

Satoh, M. et al. (Nov. 1995). "Anti-nuclear antibody production and immune-complex glomerulonephritis in BALB/c mice treated with pristane," Proc. Natl. Acad. Sci. USA 92: 10934-10938.

Scanzello, C.R. et al. (2008). "Innate immune system activation in osteoarthritis: is osteoarthritis a chronic wound?" Current Opinion in Rheumatology 20: 565-572.

(56) References Cited

OTHER PUBLICATIONS

Schlosser, M. et al. (2003). "The Direct Metalation and Subsequent Functionalization of Trifluoromethyl-Substituted Pyridines and Quinolines," Eur. J. Org. Chem., 1569-1575.
Schmidt, E. et al. (1996). "Detection of IL-1α, IL-1β and IL-1 receptor antagonist in blister fluid of bullous pemphigoid," Journal of Dermatological Science 11: 142-147.
Schmidt, M. et al. (Sep. 2010). "Crucial role for human Toll-like receptor 4 in the development of contact allergy to nickel," Nature Immunology 11(9): 814-820.
Schrepf, A. et al. (Oct. 2015). "Toll-like Receptor 4 and Comorbid Pain in Interstitial Cystitis/Bladder Pain Syndrome: A Multidisciplinary Approach to the Study of Chronic Pelvic Pain Research Network Study," Brain Behav Immun. 49: 66-74.
Scianaro, R. et al. (2014). "Deregulation of the IL-1β axis in chronic recurrent multifocal osteomyelitis," Pediatric Rheumatology 12(3): 1-6.
Sedimbi, S.K. et al. (2013). "IL-18 in inflammatory and autoimmune disease," Cell. Mol. Life Sci. 70: 4795-4802.
Seganish (2016). "Inhibitors of interleukin-1 receptor-associated kinase 4 (IRAK4): a patent review (2012-2015)," Expert Opinion on Therapeutic Patents, 26(8): 917-932.
Selway, J.L. et al. (2013). "Toll-like receptor 2 activation and comedogenesis: implications for the pathogenesis of acne," BMC Dermatology 13(10): 1-7.
Shi, Y. et al. (2010). "Monosodium urate crystals in inflammation and immunity," Immunological Reviews 233: 203-217.
Siddique, I. et al. (2011). "Mechanism of Regulation of Na—H Exchanger in Inflammatoy Bowel Disease: Role of TLR-4 Signaling Mechanism." Dig Dis Sci 56: 1656-1662.
Simone, J.V. et al. (1996). "Oncology," Part XIV in Cecil Textbook of Medicine, 20th edition, Bennet, J.C. et al. eds., W.B. Saunders Company, pp. 1004-1010.
Skabyska, Y, et al. (2016). "How the innate immune system trains immunity: lessons from studying atopic dermatitis and cutaneous bacteria," Journal of the German Society of Dermatology pp. 153-156.
Staschke, K.A. et al. (2009). "IRAK4 kinase Activity is Required for Th17 Differentiation and Th17-mediated Disease," J Immunol 183(1): 568-577.
Stokes, J.A. (2013). "Toll-like receptor signaling adapter proteins govern spread of neuropathic pain and recovery following nerve injury in male mice," Journal of Neuroinflammation 10(148): 1-14.
Sugihara, T. et al. (2010). "The increased musosal mRNA expressions of complement C3 and interleukin-17 in inflammatory bowel disease," Clinical & Experimental Immunology 160: 386-393.
Sun, M. et al. (2014). "The Role of Interleukin-1 Receptor-Associated Kinases in Vogt-Koyanagi-Herada Disease," PLOS One 9(4): 1-8.
Sun, Y. et al. (2009). "Inhibition of Corneal Inflammation by the TLR4 Antagonist Eritoran Tetrasodium (E5564)," Invest Ophthalmol Vis Sci. 50(3): 1247-1254.
Suzuki, N. et al. (2002). "Severe impairment of interleukin-1 and Toll-like receptor signaling in mice lacking IRAK-4," Nature 416: 750-754.
Swamy, K.C.K. et al. (2009). "Mitsunobu and Related Reactions: Advances and Applications," Chem. Rev. 109: 2551-2651.
Talabot-Ayer, D. et al. (2014). "Immune-mediated experimental arthritis in IL-33 deficient mice," Cytokine 69: 68-74.
Terhorst, D. et al. (2010). "The Role of Toll-Like Receptors in Host Defenses and Their Relevance to Dermatologic Disease," Am J. Clin Dermatol 11(1): 1-10.
Theoharides, T. C. et al. (Jul. 2015). "Targeting IL-33 in Autoimmunity and Inflammation," The Journal of Pharmacology and Experimental Therapeutics 354: 24-31.
Thibault, D. L. et al. (2009). "Type I interferon receptor controls B-cell expression of nucleic acid-sensing Toll-like receptors and autoantibody production in a murine model of lupus," Arthritis Research & Therapy 11(4): 1-10.

Thibault, D.L. et al. (Apr. 2008). "IRF9 and STAT1 are required for IgG autoantibody production and B cell expression of TLR7 in mice," The Journal of Clinical Investigation 118(4):1417-1426.
Timper, K. et al. (2015). "Safety, pharmacokinetics, and preliminary efficacy of a specific anti-IL-1alpha therapeutic antibody (MABp1) in patients with type 2 diabetes mellitus," Journal of Diabetes and Its Complications 29: 955-960.
U.S. Appl. No. 16/306,235, filed Nov. 30, 2018, for Beddies et al.
U.S. Appl. No. 17/009,553, filed Sep. 1, 2020, for Bothe et al. (Also published as US20210053941, cited herewith).
U.S. Appl. No. 17/544,641, filed Dec. 7, 2021, for Bothe et al.
Valcur, E. et al. (2009). "Amide bond formation: beyond the myth of coupling reagents," Chem. Soc. Rev. 38: 606-631.
Van De Veerdonk, F.L. (Jul. 2013). "New insights in the immunobiology of IL-1 family members," Frontiers in Immunology 4(167): 1-11.
Van Der Fits, L. et al. (2009). "Imiquimod-Induced Psoriasis-Like Skin Inflammation in Mice Is Mediated via the IL-23/IL-17 Axis," The Journal of Immunology 182: 5836-5845.
Vennegaard, M.T. et al. (2014). "Epicutaneous exposure to nickel induces nickel allergy in mice via a MyD88-dependent and interleukin-1-dependent pathway," Contact Dermatitis 71: 224-232.
Viguier, M. et al. (2010). "Successful Treatment of Generalized Pustular Psoriasis With the Interleukin-1-Receptor Antagonist Anakinra: Lack of Correlation with IL1RN Mutations," Annals of Internal Medicine 153: 66-67.
Vijmasi, T. et al. (2013). "Topical administration of interleukin-1 receptor antagonist as a therapy for aqueous-deficient dry eye in autoimmune disease," Molecular Vision 19: 1957-1965.
Volin, M.V. et al. (2011). "Interleukin-18: A Mediator of Inflammation and Angiogenesis in Rheumatoid Arthritis," Journal of Interferon & Cytokine Research 31(10): 745-781.
Walsh, D. et al. (2013). "Pattern recognition receptors-Molecular orchestrators of inflammation in inflammatory bowel disease," Cytokine & Growth Factor Reviews 24: 91-104.
Wan, Y.Y. et al. (2006). "The kinase TAK1 integrates antigen and cytokine receptor signaling for T cell development, survival and function," Nature Immunology 7(8): 851-858.
Wang, C. et al. (2001). "TAK1 is a ubiquitin-dependent kinase of MMK and IKK," Nature 412: 346-351.
Wolf, G. et al. (2008). "Interleukin-1 signaling in required for induction and maintenance of postoperative incisional pain: Genetic and pharmacological studies in mice," Brain, Behavior, and Immunity 22: 1072-1077.
Wollina, U. et al. (2013). "Acne inversa (Hidradenitis suppurativa): A review with a focus on pathogenesis and treatment," Indian Dermatology Online Journal 4(1): 1-11.
Won, K.A. et al. (Mar. 2014). "The Glial-Neuronal GRK2 Pathway Participates in the Development of Trigeminal Neuropathic Pain in Rats," The Journal of Pain 15(3): 250-261.
Wu, Y-W. et al. (2015). "Toll-like receptors: potential targets for lupus treatment," Acta Pharmacologica Sinica 36: 1395-1407.
Yamada, A. et al. (2017). "Targeting IL-1 in Sjogren's syndrome," Expert Opin. Ther. Targets 17(4): 393-401.
Yang, H. et al. (2005). "IL-1 Receptor Antagonist-Mediated Therapeutic Effect in Murine Myasthenia Gravis Is Associated with Suppressed Serum Proinflammatory Cytokines, C3, and Anti-Acetylcholine Receptor IgG1," The Journal of Immunology 175: 2018-2025.
Yap, D. Y. H. et al. (2013). "The role of cytokines in the pathogenesis on systemic lupus erythematosus—from bench to bedside," Nephrology 18: 243-255.
Yin, H. et al. (2012). "Adenovirus-mediated delivery of soluble ST2 attenuates ovalbumin-induced allergic asthma in mice," Clinical & Experimental Immunology 170: 1-9.
Zambrano-Zaragoza, J.F. et al. (2014). "Th17 Cells in Autoimmune and Infectious Diseases," International Journal of Inflammation 1-12.
Zarpelon, A. et al. (2013). "IL-33/ST2 signaling contributes to carrageenan-induced innate inflammation and inflammatory pain: role of cytokines, endothelin-1 and prostaglandin E2," British Journal of Pharmacology 169: 90-101.

(56) References Cited

OTHER PUBLICATIONS

Zhou, F. et al. (2005). "Arthritis in Mice That Are Deficient in Interleukin-1 Receptor Antagonist Is Dependent on Genetic Background," Arthritis & Rheumatism 52(12): 3731-3738.
Zhu, F-G. et al. (2013). "A novel antagonist of Toll-like receptors 7, 8 and 9 suppresses lupus disease-associated parameters in NZBW/F1 mice," Autoimmunity 46(7): 419-428.
Zong, M. (2014). "Anakinra treatment in patients with refractory inflammatory myopathies and possible predictive response biomarkers: a mechanistic study with 12 months follow-up," Ann Rheum Dis 73: 913-920.
U.S. Appl. No. 17/869,673, filed Jul. 20, 2022, for Bothe et al.
U.S. Appl. No. 17/869,674, filed Jul. 20, 2022, for Bothe et al.

USE OF 2-SUBSTITUTED INDAZOLES FOR THE TREATMENT AND PROPHYLAXIS OF AUTOIMMUNE DISEASES

CROSS REFERENCE TO RELATED APPLICATIONS

This application is a continuation application of U.S. patent application Ser. No. 16/863,330, filed Apr. 30, 2020, which is a continuation application of U.S. patent application Ser. No. 16/306,506, which adopts the international filing date of May 24, 2017, which is a national stage application under 35 U.S.C. § 371 of International Application No. PCT/EP2017/062535, filed internationally on May 24, 2017, which claims the benefit of European Application No. 16172507.2, filed Jun. 1, 2016.

FIELD

The present application relates to the use of 2-substituted indazoles for treatment and/or prophylaxis of diseases and to the use thereof for production of medicaments for treatment and/or prophylaxis of diseases, especially of autoimmune disorders mediated by IRAK4, such as peripheral arthritides (psoriatic arthritis, rheumatoid arthritis, reactive arthritis, systemic juvenile idiopathic arthritis), axial arthritis (in particular ankylosing spondylitis), systemic vasculitides such as giant cell arteritis and ANCA (anti-neutrophile cytoplasmic antibody)-associated vasculitides, gout and other crystal arthropathies or metabolic arthritides (hydroxyapatite arthropathy, chondrocalcinosis (calcium pyrophosphate dihydrate (CPPD), endocrine joint disorders such as in cases of hyperactivity of the parathyroid glands (hyperparathyroidism), of the thyroid gland (hyperthyroidism) in the case of diabetes mellitus), sarcoidosis, juvenile idiopathic arthritis, psoriasis, atopic dermatitis, allergic eczema/contact allergy, multiple sclerosis, systemic lupus erythematosus and so called autoinflammatory disorders such as Schnitzler syndrome, CRMO (chronic recurrent multifocal osteomyelitis), SAPHO (acronym for synovitis, acne, pustulosis, hyperostosis and osteitis) syndrome and PAPA (acronym for pyogenic arthritis, pyoderma gangraenosum and acne) syndrome, chronic inflammatory bowel disease, in particular Crohn's disease and ulcerative colitis, and inflammation-induced or chronic pain.

The present invention relates to the use of substituted indazoles of the general formula (I) which inhibit interleukin-1 receptor-associated kinase 4 (IRAK4), for use in the treatment of autoimmune disorders or dysfunctions.

BACKGROUND

Human IRAK4 (interleukin-1 receptor-associated kinase 4) plays a key role in the activation of the immune system. Therefore, this kinase is an important therapeutic target molecule for the development of inflammation-inhibiting substances. IRAK4 is expressed by a multitude of cells and mediates the signal transduction of Toll-like receptors (TLR), except for TLR3, and receptors of the interleukin (IL)-1β family consisting of the IL-1R (receptor), IL-18R, IL-33R and IL-36R (Janeway and Medzhitov, Annu. Rev. Immunol., 2002; Dinarello, Annu. Rev. Immunol., 2009; Flannery and Bowie, Biochemical Pharmacology, 2010).

Neither IRAK4 knockout mice nor human cells from patients lacking IRAK4 react to stimulation by TLRs (except for TLR3) and the IL-1I3 family (Suzuki, Suzuki, et al., Nature, 2002; Davidson, Currie, et al., J Immunol, 2006; Ku, von Bernuth, et al., JEM, 2007; Kim, Staschke, et al., JEM, 2007).

The binding of the TLR ligands or the ligands of the IL-1β family to the respective receptor leads to recruitment and binding of MyD88 [Myeloid differentiation primary response gene (88)] to the receptor. As a result, MyD88 interacts with IRAK4, resulting in the formation of an active complex which interacts with and activates the kinases IRAK1 or IRAK2 (Kollewe, Mackensen, et al., J Biol Chem, 2004; Precious et al., J. Biol. Chem., 2009). As a result of this, the NF (nuclear factor)-κB signalling pathway and the MAPK (mitogen-activated protein kinase) signal pathway is activated (Wang, Deng, et al., Nature, 2001). The activation both of the NF-κB signal pathway and of the MAPK signal pathway leads to processes associated with different immune processes. For example, there is increased expression of various inflammatory signal molecules and enzymes such as cytokines, chemokines and COX-2 (cyclooxygenase-2), for example, and increased mRNA stability of inflammation-associated genes, for example COX-2, IL-6 (interleukin-6), IL-8 (Holtmann, Enninga, et al., J Biol Chem, 2001; Datta, Novotny, et al., J Immunol, 2004). Furthermore, these processes may be associated with the proliferation and differentiation of particular cell types, for example monocytes, macrophages, dendritic cells, T cells and B cells (Wan, Chi, et al., Nat Immunol, 2006; McGettrick and J. O'Neill, Br J Haematol, 2007).

Autoimmune disorders are diseases where the immune system is directed against the body itself ("auto"), thus attacking healthy endogenous tissue. Here, the immune system may be directed either selectively only against a certain organ (e.g. the intestine in the case of ulcerative colitis, the skin in the case of psoriasis or nerves in the case of multiple sclerosis), and they are then classified as a so-called organ-specific autoimmune disorder, or it is directed against the entire system, thus causing a non-organ-specific systemic autoimmune disorder. In the case of a non-organ-specific systemic autoimmune disorder, the immune system attacks various organs of the body (for example in the case of systemic lupus erythematosus with reactions against skin, joints, kidneys, etc.). This uncontrolled malfunction of the immune system subsequently leads to chronic inflammatory processes in the body. If an autoimmune disorder remains untreated, owing to the serious inflammatory reactions, the effected organ is destroyed, which, in certain cases with a severe course (with systemic involvement), may lead to death. Accordingly, early diagnosis and therapy is of great significance.

The kinase IRAK4 or signal transduction via IRAK4 plays a central role in the underlying pathology of numerous autoimmune disorders (Chaudhary et al., J Med Chem, 2015). In particular, the central role of IRAK4 has already been demonstrated by direct comparison of wild type (WT) mice with genetically modified animals having a kinase-inactivated form of IRAK4 (IRAK4 KDKI) in an animal model of multiple sclerosis where IRAK4 KDKI animals had improved MS symptoms 9 Staschke et al., J Immunol, 2009). It has also been shown that the expression of IRAK4 correlates with the degree of Vogt-Koyanagi-Harada syndrome (Sun, Yang, et al., PLoS ONE, 2014). In addition, the high relevance of IRAK4 for immune complex-mediated IFNα (interferon-alpha) production by plasmacytoid dendritic cells, a key process in the pathogenesis of systemic lupus erythematosus (SLE), has been shown (Chiang et al., J Immunol, 2010). As well as the essential role of IRAK4 in congenital immunity, there are also hints that IRAK4 influences the differentiation of what are called the Th17 T cells, components of adaptive immunity. In the absence of IRAK4 kinase activity, fewer IL-17-producing T cells (Th17 T cells) are generated compared to WT mice. The inhibition of IRAK4 enables the prophylaxis and/or treatment of peripheral arthritides (such as psoriatic arthritis, rheumatoid arthritis, reactive arthritis, systemic juvenile idiopathic arthritis), axial arthritis (in particular Bekhterev's disease), sarcoidosis, systemic lupus erythematosus, psoriasis, vitiligo, giant cell arteriitis, atopic dermatitis, allergic eczema/contact allergy, multiple sclerosis and chronic inflammatory bowel diseases (in particular Crohn's disease and ulcerative colitis) (Staschke, et al., J Immunol, 2009; Marquez, et al., Ann Rheum Dis, 2014; Zambrano-Zaragoza, et al., International Journal of Inflammation, 2014; Ciccia, et al., Rheumatology, 2015; Cinetto and Agostini, Expert Rev Clin Immunol, 2016; Lock et al., Nat Med, 2002; Esendagli et al., J Neuroimmunol, 2013; Brucklacher Waldert et al., Brain, 2009; Li et al., J Neuroimmunol, 2011; Zambrano-Zargoza et al., Int J Inflamm, 2014; Geremia and Jewell, Expert Rev Gastroenterol Hepatol, 2012; Kobayashi et al., Gut, 2008; Sugihara et al., Clin Exp Immunol, 2010; Fujino et al., Gut, 2003; Rovedatti et al., Gut 2009).

Owing to the central role of IRAK4 in the MyD88-mediated signal cascade of TLRs (except for TLR3) and the IL-1 receptor family, the inhibition of IRAK4 can be utilized for the prophylaxis and/or treatment of disorders which are mediated by the receptors mentioned. TLRs and also components of the IL-1 receptor family are involved in the pathogenesis of rheumatoid arthritis, psoriatic arthritis, juvenile idiopathic arthritis, myasthenia gravis, vasculitis, for example Behcet's disease and giant cell arteritis, pancreatitis, systemic lupus erythematosus, dermatomyositis and polymyositis, diabetes mellitus (type 1 and type 2), diabetic nephropathy, osteoarthritis, Sjögren syndrome, Still's disease, multiple sclerosis and sepsis (Yang, Tuzun, et al., J Immunol, 2005; Zhou et al., Arthritis Rheum, 2005; Candia, Marquez et al., The Journal of Rheumatology, 2007; Li, Eur J Immunol, 2008; Scanzello, Plaas, et al. Curr Opin Rheumatol, 2008; Deng, Ma-Krupa, et al., Circ Res, 2009; Roger, Froidevaux, et al, PNAS, 2009; Devaraj, Tobias, et al., Arterioscler Thromb Vasc Biol, 2011; Ferraccioli et al., Mol Med, 2010; Kim, Cho, et al., Clin Rheumatol, 2010; Carrasco et al., Clinical and Experimental Rheumatology, 2011; Gambuzza, Licata, et al., Journal of Neuroimmunology, 2011; Fresno, Archives Of Physiology And Biochemistry, 2011; Volin and Koch, J Interferon Cytokine Res, 2011; Akash, Shen, et al., Journal of Pharmaceutical Sciences, 2012; Goh and Midwood, Rheumatology, 2012; Dasu, Ramirez, et al., Clinical Science, 2012; Ouziel, Gustot, et al., Am J Patho, 2012; Ramirez and Dasu, Curr Diabetes Rev, 2012; Okiyama et al., Arthritis Rheum, 2012; Chen et al., Arthritis Res Ther, 2013; Liu et al., Clin Rev Allergy Immunol, 2013; Sedimbi, Hagglof, et al., Cell Mol Life Sci, 2013; Van de Veerdonk et al., Front Immunol, 2013; Zarpelon et al., Br J Pharmacol, 2013; Caso, Costa, et al., Mediators of Inflammation, 2014; Cordiglieri, Marolda, et al., J Autoimmun, 2014; halal, Major, et al., J Diabetes Complications, 2014; Kaplan, Yazgan, et al., Scand J Gastroenterol, 2014; Talabot-Aye, et al., Cytokine, 2014; Zong, Dorph, et al., Ann Rheum Di, 2014; Timper, Seelig, et al., J Diabetes Complications, 2015).

Skin diseases such as psoriasis, atopic dermatitis, Kindler's syndrome, bullous pemphigoid, allergic contact dermatitis, alopecia areata, acne inversa and acne vulgaris are likewise associated with the IRAK4-mediated TLR signalling pathway or the IL-1R family (Schmidt, Mittnacht, et al., J Dermatol Sci, 1996; Hoffmann, J Investig Dermatol Symp Proc, 1999; Gilliet, Conrad, et al., Archives of Dermatology, 2004; Niebuhr, Langnickel, et al., Allergy, 2008; Miller, Adv Dermatol, 2008; Terhorst, Kalali, et al., Am J Clin Dermatol, 2010; Viguier, Guigue, et al., Annals of Internal Medicine, 2010; Carrier et al., J Invest Dermatol, 2011; Cevikbas, Steinhoff, J Invest Dermatol, 2012; Minkis, Aksentijevich, et al., Archives of Dermatology, 2012; Dispenza, Wolpert, et al., J Invest Dermatol, 2012; Minkis, Aksentijevich, et al., Archives of Dermatology, 2012; Liu et al., Clin Rev Allergy Immunol, 2013; Gresnigt and van de Veerdonk, Seminars in Immunology, 2013; Selway, Kurczab, et al., BMC Dermatology, 2013; Sedimbi, Hagglof, et al., Cell Mol Life Sci, 2013; Wollina, Koch, et al. Indian Dermatol Online, 2013; Foster, Baliwag, et al., J Immunol, 2014). TLRs and also IL-1R family members are additionally also involved in the pathogenesis of other inflammatory disorders such as allergy, Behcet's disease, crystal arthropathies such as gout, systematic lupus erythematosus, adult-onset Still's disease and chronic inflammatory bowel disorders such as ulcerative colitis and Crohn's disease, and so inhibition of IRAK4 here is a suitable prophylactic and/or therapeutic approach (Liu-Bryan, Scott, et al., Arthritis & Rheumatism, 2005; Piggott, Eisenbarth, et al., J Clin Inves, 2005; Christensen, Shupe, et al., Immunity, 2006; Cario, Inflammatory Bowel Diseases, 2010; Nickerson, Christensen, et al., The Journal of Immunology, 2010; Rakoff-Nahoum, Hao, et al., Immunity, 2006; Heimesaat, Fischer, et al., PLoS ONE, 2007; Heimesaat, Nogai, et al., Gut, 2010; Kobori, Yagi, et al., J Gastroenterol, 2010; Schmidt, Raghavan, et al., Nat Immunol, 2010; Shi, Mucsi, et al., Immunological Reviews, 2010; Coccia et al., J Exp Med, 2012; Leventhal and Schroppel, Kidney Int, 2012; Chen, Lin, et al., Arthritis Res Ther, 2013; Hao, Liu, et al., Curr Opin Gastroenterol, 2013; Kreisel and Goldstein, Transplant International, 2013; Li, Wang, et al., Pharmacology & Therapeutics, 2013; Walsh, Carthy, et al., Cytokine & Growth Factor Reviews, 2013; Zhu, Jiang, et al., Autoimmunity, 2013; Yap and Lai, Nephrology, 2013; Vennegaard, Dyring-Andersen, et al., Contact Dermatitis, 2014; D'Elia, Brucato, et al., Clin Exp Rheumatol, 2015; Jain, Thongprayoon, et al., Am J Cardiol., 2015; Li, Zhang, et al., Oncol Rep., 2015).

In addition to the disorders already mentioned, IRAK4-mediated TLR processes have been described in the pathogenesis of inflammatory eye disorders such as uveitis, keratitis and allergic conjunctivitis (Li et al., Curr Mol Med. 2009; Bascherini et al., Clin Rheumatol. 2015; Sun and Pearlman, Investigative Ophthalmology & Visual Science, 2009; Redfern and McDermott, Experimental Eye Research, 2010; Kezic, Taylor, et al., J Leukoc Biol, 2011; Chang, McCluskey, et al., Clinical & Experimental Ophthalmology, 2012).

Because of the involvement of TLR-mediated signals and IL-1 receptor family-mediated signals via IRAK4 in the case of pruritus and pain, including acute, chronic, inflammatory and neuropathic pain, there may be assumed to be a therapeutic effect in the indications mentioned through the inhibition of IRAK4. Examples of pain include hyperalgesia, allodynia, post-operative pain, neuropathic pain, abdominal pain, inflammation-induced pain, lower back pain, and chronic pain (Wolf et al., Brain Behav Imm, 2008; Kim et al., Toll-like Receptors: Roles in Infection and Neuropathology, 2009; del Rey, Apkarian, et al., Ann N Y AcSci, 2012; Guerrero et al., Eur J Pharmacol, 2012; Kwok et al., PLoS ONE, 2012; Nicotra, et al., Ex Neurol, 2012; Chopra and Cooper, J Neuroimmune Pharmacol, 2013; David et al., Neurobiol Dis, 2013; Liu and Ji, Pflugers Arch., 2013;

Stokes et al., J Neuroinflammation, 2013; Park, Stokes, et al., Cancer Chemother Pharmacol, 2014; Won et al., J Pain, 2014; Siddique and Khan, Dig Dis Sci. 2011; Schrepf et al., Brain Behav Immun, 2015).

Inflammatory disorders such as CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome; FMF (familial mediterranean fever), HIDS (hyper-IgD syndrome), TRAPS (tumour necrosis factor receptor 1-associated periodic syndrom), juvenile idiopathic arthritis, adult-onset Still's disease, Adamantiades-Behcet's disease, rheumatoid arthritis, osteoarthritis, Schnitzler's syndrome, SAPHO (acronym for synovitis, acne, pustulosis, hyperostosis and osteitis) syndrome, PAPA (acronym for pyogenic arthritis, Pyoderma gangraenosum and acne) syndrome, PASS (acronym for pyoderma gangraenosum, acne vulgaris, hidradenitis suppurativa and ankylosing spondylitis) syndrome and Sjögren syndrome are treated by blocking the IL-1 signal pathway; therefore here, too, an IRAK4 inhibitor is suitable for treatment of the diseases mentioned (Narayanan et al., Cornea 2008; Brenner et al., Br J Dermatol, 2009; Henderson and Goldbach-Mansky, Clin Immunol, 2010; Dinarello, European Journal of Immunology, 2011; Gul, Tugal-Tutkun, et al., Ann Rheum Dis, 2012; Pettersson, Annals of MedicinePetterson, 2012; Ruperto et al., N Engl J Med, 2012; Nordström et al., J Rheumatol, 2012; Vijmasi et al., Mol Vis, 2013; Yamada et al., Expert Opin Ther Target, 2013; de Koning, Clin Transl Allergy, 2014). The ligand of IL-33R, IL-33, is involved particularly in the pathogenesis of atopic dermatitis and allergic eczema/dermatitis and Bekhterev's disease, and so the inhibition of IRAK4 for prophylaxis and/or treatment is a suitable therapeutic approach (Li et al., J Investig Med, 2013; Theoharides et al., J Pharmacol Exp Ther. 2015; Saluja et al., Clin Transl Allergy. 2015; Firinu et al., Curr Rheumatol Rep, 2016; Leuenberger et al., Dermatology, 2016; Nygaard et al., J Eur Acad Dermatol Venereol. 2016; Omenetti et al., Rheumatology (Oxford), 2016). Components of the IL-1 receptor family are associated with different inflammatory disorders such as asthma, COPD, idiopathic interstitial pneumonia, allergic rhinitis, pulmonary fibrosis, acute respiratory distress syndrome (ARDS) and CRMO (chronic recurrent multifocal osteomyelitis), and so prophylactic and/or therapeutic action is to be expected in the indications mentioned through the inhibition of IRAK4 (Kang et al., J Immunol, 2007; Imaoka et al., Eur Resp J, 2008; Couillin et al., J Immunol, 2009; Lloyd, Curr Opin Immunol, 2010; Pauwels, et al., Eur Respir J, 2011; Haenuki, et al., J Allergy Clin Immunol, 2012; Yin, et al., Clin Exp Immunol, 2012; Alexander-Brett, et al., J Clin Invest, 2013; Bunting, et al., BioMed Res Int, 2013; Byers, et al., J Clin Invest, 2013; Kawayama, et al., J Interferon Cytokine Res, 2013; Martinez-Gonzalez et al., Am J Respir Cell Mol Biol, 2013; Nakanishi et al., PLoS ONE, 2013; Qiu et al, Immunol, 2013; Li, et al., J Allergy Clin Immunol, 2014; Saluja, et al., Mol Immunol, 2014; Scianaro et al., Pediatr Rheumatol Online, 2014; Lugrin, et al., J Immunol, 2015).

As standard therapy in cases of autoimmune disorders such as multiple sclerosis, systemic lupus erythematosus, psoriasis and peripheral arthritides, use is made of immunosuppressants which substantially suppress the immune system.

Current pharmacological therapy of multiple sclerosis (MS) follows different approaches:

therapy of the acute MS episode using high-dose systemic steroids, symptomatic therapy with various medicaments matching the symptoms and a therapy for the prevention of new MS episodes. Here, use is made of parenteral (e.g. beta-interferons, glatiramer acetate, natalizumab), and oral medicaments (e.g. fingolimod (dimethyl fumarate), teriflunomide), and also of cortisone preparations (e.g. prednisolone or methyl prednisolone).

For the therapy of systemic lupus erythematosus (SLE), use is made of immunosuppressants or immunomodulators such as NSAIDs, hydroxychloroquin, systemic steroids (glucocorticoids), mycophenolat mofetil (MMF), azathioprine, leflunomide, methotrexate, cyclosporine or cyclophosphamide, frequently in combination and as interval/maintenance therapy, or belimumab or rituximab, antibodies to be applied parenterally.

Psoriasis therapy depends on the degree of severity and is carried out using topical steroids and vitamin D3 analogues (or a combination of both) or topic dithranol or retinoid, frequently together with exfoliating compounds (such as salicylic acid or urea) to be applied externally, and phototherapy. In some cases, calcineurine inhibitors such as tacrolimus and pimecrolimus are employed, too. Systemic therapies available are, inter alia, methotrexate, cyclosporine, fumaric esters, apremilast, retinoid TNF blockers and other active compounds. Biologics such as TNF blockers (e.g. etanercept, infliximab, adalimumab, golimumab and certolizumab pegol) or interleukin-inhibiting monoclonal antibodies such as ustekinumab and secukinumab are also used in psoriasis treatments.

For the treatment of atopic dermatitis (neurodermatitis) and allergic eczema, use is made of steroids, salicylic acid, urea, calcineurine inhibitors such as tacrolimus, antibiotics (e.g. mupirocin), antihistamines, cyclosporine and phototherapy.

For the therapy of arthritides such as rheumatoid arthritis, psoriatic arthritis and Bekhterev's disease, in addition to NSAIDs (non-steroidal anti-inflammatory drugs), hydroxychloroquine and steroids (e.g. prednisone), the so-called chemical disease-modifying drugs (DMARDS) such as methotrexate, sulfasalazine and leflunomide, TNF-blockers and other active compounds are available. Biologics such as TNF blockers (infliximab, adalimumab, golimumab and certolizumab pegol, and also etanercept), rituximab, abatacept or interleukin-inhibiting monoclonal antibodies such as ustekinumab, tocilizumab and secukinumab, or Jak/STAT inhibitors such as tofacitinib are used for treating arthritides.

Patients with chronic inflammatory bowel disorders are treated, for example, with antibiotics such as ciprofloxacin and metronidazole, antidiuretics such as loperamide or laxatives (bisacodyl) and probiotic bacteria (Mutaflor, VSL #3®, *Lactobacillus* GG, *Lactobacillus plantarum*, *L. acidophilus*, *L. casei*, *Bifidobacterium infantis* 35624, *Enterococcus fecium* SF68, *Bifidobacterium longum*, *Escherichia coli* Nissle 1917). Furthermore, the patients respond to topical treatment with steroids (e.g. with budesonide) or systemic treatment with steroids (e.g. prednisolone). Moreover, sulfasalazine, azathioprine, mercaptopurine, methotrexate, cyclosporine, TNF-blockers (e.g. adalimumab, etanercept) and integrin antibodies (e.g. vedolizumab, natalizumab) are used for treatment.

However, the known therapeutical approaches do not eliminate the cause of the disorder and may result in life-threatening infections.

In certain cases all of the therapies described may cause serious side-effects, e.g. osteoporosis, negative effects on glucose levels (systemic steroids), in some cases lethal infections, reactivation of tuberculosis (TNF blockers), organ damage (pancreatitis, hepatitis, pneumonitis), infusion and injection reactions, auto-antibody formation (most parenteral biologics), increased risk of cancer (TNF blockers) and others. None of the therapies mentioned cures the disorders described, and new episodes and exacerbations are very frequent, in particular when the therapy is discontinued.

It is an object of the present invention to provide alternative options for the treatment of autoimmune disorders, in particular of multiple sclerosis, systemic lupus erythematosus, psoriasis, peripheral arthritides (in particular psoriatic arthritis, rheumatoid arthritis, reactive arthritis, systemic juvenile idiopathic arthritis), axial arthritis (in particular Bechterew disease), chronic inflammatory bowel disorders (in particular Crohn's disease, ulcerative colitis), atopic dermatitis and allergic eczema/contact dermatitis.

DETAILED DESCRIPTION

Figure 1:
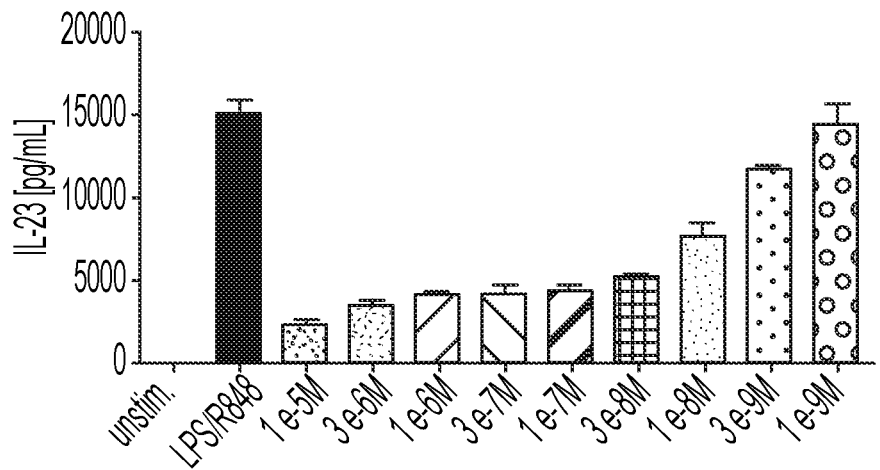
FIG. 1: Inhibition of IL-23 in human monocyte-generated DCs for Example Compound 12. Data is shown as mean values with standard deviations.

The problem addressed by the present invention is solved by the use of compounds of the general formula (I)

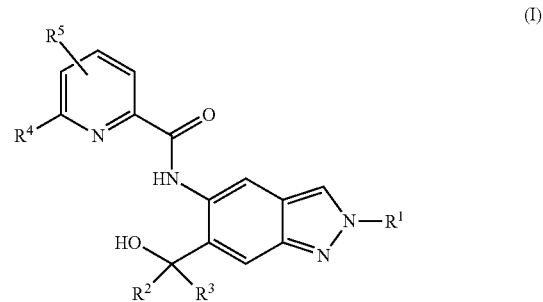

(I)

in which:
$R^1$ is $C_1$-$C_6$-alkyl, where the $C_1$-$C_6$-alkyl radical is unsubstituted or mono- or polysubstituted identically or differently by
  halogen, hydroxyl, an unsubstituted or mono- or polyhalogen-substituted $C_3$-$C_6$-cycloalkyl, or an $R^6$, $R^7SO_2$, $R^7SO$ or $R^8O$ radical,
or a group selected from:

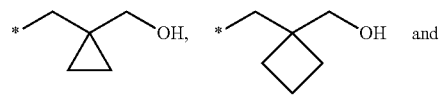

and

-continued

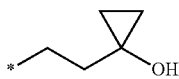

where * represents the bonding site of the group to the rest of the molecule;
$R^2$ and $R^3$ always have the same definition and are both either hydrogen or $C_1$-$C_6$-alkyl;
$R^4$ is halogen, cyano, an unsubstituted or a singly or multiply, identically or differently substituted $C_1$-$C_6$-alkyl or an unsubstituted or a singly or multiply, identically or differently substituted $C_3$-$C_6$-cycloalkyl, and the substituents are selected from the group of halogen and hydroxyl;
$R^5$ is hydrogen, halogen or an unsubstituted or mono- or poly-halogen-substituted $C_1$-$C_6$-alkyl;
$R^6$ is an unsubstituted or mono- or di-methyl-substituted monocyclic saturated heterocycle having 4 to 6 ring atoms, which contains a heteroatom or a heterogroup from the group of O, S, SO and $SO_2$;
$R^7$ is $C_1$-$C_6$-alkyl, where the $C_1$-$C_6$-alkyl radical is unsubstituted or mono- or polysubstituted identically or differently by halogen, hydroxyl or $C_3$-$C_6$-cycloalkyl, or $R^7$ is $C_3$-$C_6$-cycloalkyl;
$R^8$ is $C_1$-$C_6$-alkyl, where the $C_1$-$C_6$-alkyl radical is unsubstituted or mono- or polysubstituted identically or differently by halogen;
and the diastereomers, enantiomers, metabolites, salts, solvates or solvates of the salts thereof for treatment and/or prophylaxis of autoimmune disorders which are mediated by IRAK4.

A further embodiment of the invention consists in the use of the compounds of the general formula (I) for the treatment and/or prophylaxis of multiple sclerosis, systemic lupus erythematosus, psoriasis, atopic dermatitis and allergic eczema, arthritis (in particular psoratic arthritis, Bechterew disease, rheumatoid arthritis, reactive arthritis, systemic juvenile idiopathic arthritis), chronic inflammatory bowel disorders (in particular Crohn's disease, ulcerative colitis).

For the purpose of the present invention, multiple sclerosis (MS), which is also referred to as encephalomyelitis disseminata (ED), is understood to mean a chronic inflammatory disorder of the central nervous system which embraces the brain and spinal cord and during the course of which nerve structures, in particular the myelin sheath, are destroyed by an autoreactive immune system. In most cases, the onset of the disorder is in early adulthood, and it may lead to various symptoms such as impaired vision, pain and/or paralysis. The frequency of multiple sclerosis among women is about twice that among men. There is still no cure for MS, but its course can be attenuated using medicaments such as teriflunomide, dimethyl fumarate and fingolimod. From individual to individual, the course of MS may differ strongly. The two most significant forms of progression of MS is the episodic and the chronically progressive (progredient) course. Frequently (in about 80% of patients), an initially episodic remitting course (relapsing remitting, RR-MS for short) later changes to a chronically progredient course (secondary progressive, SP-MS for short). Less often (in about 10% of MS cases) there is a chronically progressive course even at the beginning (primary progressive, PP-MS for short), without any episodes of the disorder being noticeable beforehand.

For the purpose of the present invention, systemic lupus erythematosus (SLE) is to be understood as meaning a chronic and life-threatening autoimmune disorder which may lead to multiple organ pathologies, skin manifestations (e.g. butterfly rash) and a kidney disorder (lupus nephritis). Here, the formation of autoreactive B cells secreting anti-DNA (deoxyribonucleic acid) and other autoantibodies leads to the formation of pathogenetically relevant immune complexes. These can then activate cells of the immune system, for example plasmacytoid dendritic cells (pDCs) via endosomal nucleic acid-specific toll-like receptors (TLR), specifically TLR7 and TLR9. This results in the production of type I interferon (such as IFN-alpha and TNF-α) (Chen et al., Clinic Rev Allerg Immunol, 2015). In addition to INF-α and TNF-α, in SLE patients a significant increase of the serum levels of IL-6 and IFN-γ compared to healthy individuals is also observed (Lyn-Cook et al., Mol Immunol, 2014). Also, there is an increased frequency of circulating ThH17 cells (T helper cells of type 17) followed by an increase of IL-17 serum levels, both of which correlate with the degree of severity of the disorder (Zambrano-Zargoza et al., Int J Inflamm, 2014).

For the purpose of the present invention, psoriasis is understood as meaning a chronic skin inflammation with episodic progression and increased flaking of the skin. Characteristic symptoms are silver-white roundish skin lesions which flake strongly and preferably occur at knees, elbows and scalp. The affected areas are frequently very itchy. Responsible for the development of psoriasis is a chronic inflammatory reaction mediated by Th1 and Th17 cells (T helper cells of type 1 or type 17). During this inflammatory reaction, proinflammatory cytokines such as IFN-γ, TNF-α, IL-23 and IL-17 are produced (Deng et al., Clin Rev Allergy Immunol. 2016; Zambrano-Zargoza et al., Int J Inflamm, 2014; Chen et al., Clinic Rev Allerg Immunol, 2015). This results in ceratinocytes proliferating and migrating into the horny layer of the skin about seven times more rapidly (instead of 28 days, in the case of psoriasis patients this only takes about 4 days). This results in a rapid neoformation of the epidermis. In addition to the skin, the nails are also frequently affected, displaying indentations and brownish spots. In about 25% of the patients, the joints are also affected, which is referred to as psoriatic arthritis (Raychaudhuri et al., Clin Rheumatol., 2015).

For the purpose of the present invention, atopic dermatitis (neurodermatitis) and allergic eczema is to be understood as meaning a chronic inflammatory skin disorder associated with itching. Whereas allergic eczema is the result of a specific inappropriate overreaction of the immune system to an external allergen which, per se, would not be harmful to the organism, in contrast, in the case of neurodermatitis patients the protective function of the skin is reduced. In atopic patients, contact with physical, chemical or microbial stimuli may then result in inflammation. Atopic dermatitis frequently starts in infancy and childhood and typically progresses with episodes which may alternate with phases with few symptoms, if any (Malajian and Guttman-Yassky, Cytokine, 2015). Allergic reactions such as allergic eczema may trigger or maintain atopic dermatitis (Fischer et al., Der Hautarzt, 2003). In many neurodermatitis patients, an increased level of immunoglobulin E (IgE), which plays an important role in allergic reactions, can be detected. Allergic eczema requires uncovering of the causes, i.e. the allergen, by an epicutane test, and subsequently allergen avoidance is of central importance. An immune reaction of type Th2 is common to inflammatory skin disorders, i.e. owing to the allergen contact or due to the defective skin barrier and thus invasion of, for example, bacteria, the autoreactive immune system in these patients is stimulated via TLR or receptors of the IL-1 family, resulting in the activation of Th2 cells. As a consequence of this immune response, proinflammatory cytokines such as IL-4, IL-5, IL-13, IL-18, IL-33, etc., are produced (Kaesler et al., J Allergy Clin Immunol. 2014; Panzer et al., Exp Dermatol, 2014; Skabytska et al., J Dtsch Dermatol Ges, 2016; Paul, Cytokine, 2015; Malajian and Guttman-Yassky, Cytokine, 2015; McKenzie, Ann Am Thorac Soc. 2014).

For the purpose of the present invention, arthritis (psoriatic arthritis, rheumatoid arthritis, reactive arthritis, Bechterew disease, systemic juvenile idiopathic arthritis) is to be understood as meaning an inflammatory joint disorder. Here, axial arthritis characterized by an inflammation of the spinal joints (e.g. Bechterew disease) is distinguished from peripheral arthritis where the joints of the extremities such as toes, ankles, knee, fingers, hands or else elbows are mainly affected. Here, peripheral arthritis can be symmetrical, i.e. the same joints of both sides of the body are both affected (e.g. rheumatoid arthritis) or else asymmetrical, i.e. inflamed joints are distributed unevenly over both sides of the body (e.g. psoriatic arthritis). Here, the mobility of the inflamed joints is painfully restricted, and the skin above is reddened and hyperthermic. The arthritic disorders are characterized by episodic progredient progression which may result in destruction of the joints and serious disability up to invalidity. Autoreactive B cells, Th1 cells and Th17 cells and also proinflammatory cytokines such as IFN-γ, TNF, IL-6, IL-12, IL-23 and IL-17 play a central role in induction, but also progression, of the pathological processes of arthritis. These immune cells also induce the production of metalloproteinases as well as maturation and activation of osteoclasts, which then results in destruction of the cartilage and the bone in the joint affected (Raychaudhuri et al., Clin Rheumatol, 2015; Burmester et al., Ann Rheum Dis, 2015; Furst and Emery, Rheumatol, 2014; McInnes and Schett, Engl J Med, 2011).

For the purpose of the present invention, chronic inflammatory bowel disease (IBD) with its main forms Crohn's disease and ulcerative colitis is to be understood as meaning an episodic inflammation of the gastrointestinal tract which can persist the entire life. Although Crohn's disease and ulcerative colitis share many pathological characteristics and clinical symptoms (such as bloody diarrhoea with abdominal cramps followed by weight loss) they also differ in many aspects. Whereas in the case of Crohn's disease inflammation may occur in the entire gastrointestinal tract from the oral cavity to the anus, in the case of ulcerative colitis patients it is limited to the colon. Also, in the case of Crohn's disease, the spread of the intestinal inflammation is more uneven, i.e. healthy and inflamed sections alternate, whereas in the case of ulcerative colitis the inflammation is spread evenly from the anus over the colon. In addition, there may also be symptoms outside of the gastrointestinal tract, for example at the joints and the skin, and also liver inflammations. Furthermore, ulcerative colitis patients in particular have an increased risk of bowel cancer (Geremia et al., Autoimmunity Rev, 2014). Both diseases occur more frequently between the ages of 20 and 40, however, children and adolescents may also be affected. The chronic-inflammatory bowel disorders cannot be cured; however, frequency and intensity of the episodes of the disease can be reduced by treatment with medicaments, for example by sulfasalazine, steroids or biologics (such as anti-TNF antibodies) and lifestyle modification.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt" or "x HCl", "x CF$_3$COOH", "x Na$^+$" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

Compounds of the formula (I) are understood to mean the compounds as such as well as the salts, solvates and solvates of the salts thereof, the compounds that are encompassed by formula (I) and are of the formulae mentioned below and the salts, solvates and solvates of the salts thereof and the compounds that are encompassed by the formula (I) and are mentioned below as embodiments and the salts, solvates and solvates of the salts thereof if the compounds that are encompassed by the formula (I) and are mentioned below are not already salts, solvates and solvates of the salts.

Preferred salts in the context of the present invention are physiologically acceptable salts of the compounds of the general formula (I). However, the invention also encompasses salts which themselves are unsuitable for pharmaceutical applications but which can be used, for example, for the isolation or purification of the compounds of the general formula (I).

Physiologically acceptable salts of the compounds of the general formula (I) include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the general formula (I) also include salts of conventional bases, by way of example and with preference alkali metal salts (e.g. sodium and potassium salts), alkaline earth metal salts (e.g. calcium and magnesium salts) and ammonium salts derived from ammonia or organic amines having 1 to 16 carbon atoms, by way of example and with preference ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine. Solvates in the context of the invention are described as those forms of the compounds of the general formula (I) which form a complex in the solid or liquid state by coordination with solvent molecules. Hydrates are a specific form of the solvates in which the coordination is with water.

The compounds of the general formula (I) may, depending on their structure, exist in different stereoisomeric forms, i.e. in the form of configurational isomers or else, if appropriate, of conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably used for this purpose, especially HPLC chromatography on an achiral or chiral phase.

If the compounds of the general formula (I) can occur in tautomeric forms, the present invention encompasses all the tautomeric forms.

The compounds of the general formula (I) can also be present in the form of all suitable isotopic variants of the compounds of the general formula (I). An isotopic variant of an inventive compound is understood here as meaning a compound in which at least one atom within the inventive compound has been exchanged for another atom of the same atomic number, but with a different atomic mass than the atomic mass which usually or predominantly occurs in nature. Examples of isotopes which can be incorporated into an inventive compound are those of hydrogen, carbon, nitrogen, oxygen, phosphorus, sulphur, fluorine, chlorine, bromine and iodine, such as 2H (deuterium), 3H (tritium), 13C, 14C, 15N, 17O, 18O, 32P, 33P, 33S, 34S, 35S, 36S, 18F, 36Cl, 82Br, 123I, 124I, 129I and 131I. Particular isotopic variants of an inventive compound, such as, in particular, those in which one or more radioactive isotopes have been incorporated, may be beneficial, for example, for the examination of the mechanism of action or of the active ingredient distribution in the body; because of the comparative ease of preparability and detectability, particularly compounds labelled with 3H or 14C isotopes are suitable for this purpose. In addition, the incorporation of isotopes, for example of deuterium, may lead to particular therapeutic benefits as a consequence of greater metabolic stability of the compound, for example an extension of the half-life in the body or a reduction in the active dose required; such modifications of the compounds of the general formula (I) may therefore in some cases also constitute a preferred embodiment of the present invention. Isotopic variants of the compounds of the general formula (I) can be prepared by the processes known to those skilled in the art, for example by the methods described further below and the procedures described in the working examples, by using corresponding isotopic modifications of the respective reagents and/or starting compounds.

The term compounds of the general formula (I) additionally also encompasses prodrugs of the compounds of the general formula (I). The term "prodrugs" in this context refers to compounds which may themselves be biologically active or inactive but are converted (for example metabolically or hydrolytically) to compounds of the general formula (I) during their residence time in the body.

In the context of the present invention, unless specified otherwise, the substituents have the following meanings:

Alkyl in the context of the invention represents a straight-chain or branched alkyl radical having the particular number of carbon atoms specified. Examples include methyl, ethyl, n-propyl, isopropyl, n-butyl, isobutyl, 1-methylpropyl, 2-methylpropyl, tert-butyl, n-pentyl, 1-ethylpropyl, 1-methylbutyl, 2-methylbutyl, 3-methylbutyl, 2,2-dimethylpropyl, n-hexyl, 1-methylpentyl, 2-methylpentyl, 3-methylpentyl, 4-methylpentyl, 1-ethylbutyl and 2-ethylbutyl. Preference is given to methyl, ethyl, n-propyl, n-butyl, 2-methylbutyl, 3-methylbutyl and 2,2-dimethylpropyl.

Cycloalkyl in the context of the invention is a monocyclic saturated alkyl radical having the number of carbon atoms specified in each case. Preferred examples include cyclopropyl, cyclobutyl, cyclopentyl and cyclohexyl.

Alkoxy in the context of the invention represents a straight-chain or branched alkoxy radical having the particular number of carbon atoms specified. 1 to 6 carbon atoms are preferred. Examples include methoxy, ethoxy, n-propoxy, isopropoxy, 1-methylpropoxy, n-butoxy, isobutoxy, tert-butoxy, n-pentoxy, isopentoxy, 1-ethylpropoxy, 1-methylbutoxy, 2-methylbutoxy, 3-methylbutoxy and n-hexoxy. Particular preference is given to a linear or branched alkoxy radical having 1 to 4 carbon atoms. Examples which may be mentioned as being preferred are methoxy, ethoxy, n-propoxy, 1-methylpropoxy, n-butoxy and isobutoxy.

Halogen in the context of the invention is fluorine, chlorine and bromine. Preference is given to fluorine.

Hydroxyl in the context of the invention is OH.

A monocyclic saturated heterocycle is a monocyclic saturated heterocycle which has 4 to 6 ring atoms and contains a heteroatom or a heterogroup from the group of O, S, SO and $SO_2$. A heterocycle having a heteroatom or a heterogroup from the group of O, SO and $SO_2$ is preferred. Examples include: oxetane, tetrahydrofuran, tetrahydro-2H-pyran-4-yl, 1,1-dioxidotetrahydro-2H-thiopyran-3-yl, 1,1-dioxidotetrahydro-2H-thiopyran-2-yl, 1,1-dioxidotetrahydro-2H-thiopyran-4-yl, 1,1-dioxidotetrahydrothiophen-3-yl, 1,1-dioxidotetrahydrothiophen-2-yl, 1,1-dioxidothietan-2-yl or 1,1-dioxidothietan-3-yl. Particular preference is given here to oxetane and tetrahydrofuran. Very particular preference is given to oxetan-3-yl.

A symbol * at a bond denotes the bonding site in the molecule.

When radicals in the compounds of the general formula (I) are substituted, the radicals may be mono- or polysubstituted, unless specified otherwise. In the context of the present invention, all radicals which occur more than once are defined independently of one another. Substitution by one, two or three identical or different substituents is preferred.

A preferred embodiment of $R^1$ is a $C_2$-$C_6$-alkyl radical substituted by 1, 2 or 3 fluorine atoms. Particular preference is given to 2,2,2-trifluoroethyl, 3,3,3-trifluoropropyl and 4,4,4-trifluorobutyl. Very particular preference is given to a 4,4,4-trifluorobutyl radical.

A further preferred embodiment of $R^1$ is a $C_2$-$C_6$-alkyl radical substituted by one or two hydroxyl group(s) or one $C_1$-$C_3$-alkoxy or a tri-fluorine-substituted $C_1$-$C_3$-alkoxy. Particular preference is given to a $C_2$-$C_5$-alkyl radical substituted by hydroxyl or $C_1$-$C_3$-alkoxy or trifluoromethoxy or 2,2,2-trifluoroethoxy. Very particular preference is given to 3-hydroxy-3-methylbutyl, 3-methoxypropyl, 3-hydroxypropyl, 3-trifluoromethoxypropyl, 2-methoxyethyl or 2-hydroxyethyl. Especially preferred is the 3-hydroxy-3-methylbutyl radical.

Further preferably, $R^1$ is a $C_2$-$C_6$-alkyl radical substituted by a $C_1$-$C_6$-alkyl-$SO_2$ group. A methyl-$SO_2$-substituted $C_2$-$C_4$-alkyl radical is particularly preferred. Especially preferred for $R^1$ are 2-(methylsulphonyl)ethyl or 3-(methylsulphonyl)propyl. From the latter group, 2-(methylsulphonyl)ethyl is particularly preferred.

Additionally preferably, $R^1$ is a $C_1$-$C_3$-alkyl radical substituted by oxetanyl, tetrahydrofuranyl, tetrahydro-2H-pyran-4-yl, 1,1-dioxidotetrahydro-2H-thiopyran-3-yl, 1,1-dioxidotetrahydro-2H-thiopyran-2-yl, 1,1-dioxidotetrahydro-2H-thiopyran-4-yl, 1,1-dioxidotetrahydrothiophen-3-yl, 1,1-dioxidotetrahydrothiophen-2-yl, 1,1-dioxidothietan-2-yl or 1,1-dioxidothietan-3-yl. Particular preference is given to a $C_1$-$C_3$-alkyl radical substituted by an oxetane group. Especially preferred for $R^1$ is an oxetan-3-ylmethyl group.

For $R^2$ and $R^3$, which always have the same definition, hydrogen or methyl are preferred. Methyl is particularly preferred.

In the case of $R^4$, preference is given to an unsubstituted or mono- or poly-halogen-substituted $C_1$-$C_3$-alkyl radical or a $C_1$-$C_3$-alkyl radical substituted by one hydroxyl group or a $C_1$-$C_3$-alkyl radical substituted by one hydroxyl group and three fluorine atoms.

For $R^4$, particular preference is given to the following radicals: methyl, ethyl, trifluoro-$C_1$-$C_3$-alkyl, difluoro-$C_1$-$C_3$-alkyl, hydroxymethyl, 1-hydroxyethyl, 2-hydroxypropan-2-yl and 2,2,2-trifluoro-1-hydroxyethyl. For $R^4$, particular preference is given to the methyl, trifluoromethyl and difluoromethyl radicals. Particular preference is given here to a trifluoromethyl radical.

A preferred embodiment of $R^1$ is hydrogen, fluorine, chlorine or $C_1$-$C_3$-alkyl. More preferably, $R^1$ is hydrogen, fluorine or methyl. Most preferably, $R^1$ is hydrogen or fluorine.

Particular preference is also given to compounds in which $R^4$ is methyl or trifluoromethyl and $R^1$ is fluorine. Very particular preference is given to compounds in which $R^4$ is methyl and $R^1$ is fluorine, where $R^1$ is in the ortho position to $R^4$.

For $R^6$, preferred embodiments include oxetanyl, tetrahydrofuranyl, tetrahydro-2H-pyran-4-yl, 1,1-dioxidotetrahydro-2H-thiopyran-3-yl, 1,1-dioxidotetrahydro-2H-thiopyran-2-yl, 1,1-dioxidotetrahydro-2H-thiopyran-4-yl, 1,1-dioxidotetrahydrothiophen-3-yl, 1,1-dioxidotetrahydrothiophen-2-yl, 1,1-dioxidothietan-2-yl or 1,1-dioxidothietan-3-yl. Particular preference is given here to oxetanyl. Very particular preference is given to oxetan-3-yl.

$R^7$ is exclusively connected to the functional groups —$SO_2$— and —SO—, i.e. is an $R^7$-substituted —$SO_2$— or SO group. In this connection, $R^7$ is preferably $C_1$-$C_4$-alkyl, where the $C_1$-$C_4$-alkyl radical is unsubstituted or monosubstituted by hydroxyl or by cyclopropyl or substituted by three fluorine atoms. Additionally preferred for $R^7$ is a cyclopropyl radical. Particularly preferred for $R^7$ are methyl, ethyl or hydroxyethyl. Very particular preference is given to methyl for $R^7$.

This means that, in the case of a $C_1$-$C_6$-alkyl radical substituted by $R^7SO_2$— or $R^7SO$—, in the context of $R^1$, preference is given to a $C_1$-$C_6$-alkyl substituted by a $C_1$-$C_6$-alkyl-$SO_2$ or a $C_1$-$C_6$-alkyl-SO. For $R^1$, preference is given here especially to methylsulphonylethyl and methylsulphonylpropyl. Very particular preference is given here to methylsulphonylethyl.

For $R^8$, preference is given to an unsubstituted $C_1$-$C_4$-alkyl radical or a tri-fluorine-substituted $C_1$-$C_4$-alkyl radical. Particular preference is given to methyl, ethyl, trifluoromethyl or 2,2,2-trifluoroethyl. Very particular preference is given to methyl, trifluoromethyl or 2,2,2-trifluoroethyl.

Preference is given to the use of compounds of the formula (I) in which $R^1$ is $C_1$-$C_6$-alkyl, where the $C_1$-$C_6$-alkyl radical is unsubstituted or mono- or polysubstituted identically or differently by fluorine, hydroxyl or an $R^6$, $R^7SO_2$, $R^7SO$ or $R^8O$ radical;

$R^2$ and $R^3$ always have the same definition and are both either hydrogen or $C_1$-$C_3$-alkyl;

$R^4$ is halogen, cyano or $C_1$-$C_3$-alkyl, where the $C_1$-$C_3$-alkyl radical is unsubstituted or mono- or polysubstituted identically or differently by halogen or hydroxyl;

$R^5$ is hydrogen, fluorine, chlorine or $C_1$-$C_3$-alkyl;

$R^6$ is oxetanyl or tetrahydrofuranyl;

$R^7$ is $C_1$-$C_4$-alkyl, where the $C_1$-$C_4$-alkyl radical is unsubstituted or monosubstituted by hydroxyl or by cyclopropyl or substituted by three fluorine atoms;

$R^8$ is unsubstituted $C_1$-$C_4$-alkyl or tri-fluorine-substituted $C_1$-$C_4$-alkyl;

and the diastereomers, enantiomers, metabolites, salts, solvates or solvates of the salts thereof for treatment and/or prophylaxis of autoimmune disorders which are mediated by IRAK4, especially for treatment and prophylaxis of multiple sclerosis, systemic lupus erythematosus, psoriasis, arthritis (psoriatic arthritis, Bekhterev's disease, rheumatoid arthritis, reactive arthritis, systemic juvenile idiopathic arthritis), chronic-inflammatory bowel disorders (Crohn's disease, ulcerative colitis), atopic dermatitis and allergic eczema.

Preference is additionally given to the use of compounds of the formula (I) in which $R^1$ is $C_2$-$C_6$-alkyl, where $C_2$-$C_6$-alkyl is unsubstituted, or $C_2$-$C_6$-alkyl is mono-, di- or tri-fluorine-substituted or $C_2$-$C_6$-alkyl is monosubstituted by hydroxyl, $R^6$, $R^7SO_2$, or $R^8O$, or in which $R^1$ is an oxetanyl-substituted $C_1$-$C_3$-alkyl;

$R^2$ and $R^3$ always have the same definition and are both either hydrogen or methyl;

$R^4$ is an unsubstituted or mono- or poly-halogen-substituted $C_1$-$C_3$-alkyl radical or a $C_1$-$C_3$-alkyl radical substituted by one hydroxyl group or a $C_1$-$C_3$-alkyl radical substituted by one hydroxyl group and three fluorine atoms;

$R^5$ is hydrogen, fluorine or $C_1$-$C_3$-alkyl;

$R^7$ is $C_1$-$C_3$-alkyl;

$R^8$ is $C_1$-$C_4$-alkyl, where the $C_1$-$C_4$-alkyl radical is unsubstituted or mono-, di- or tri-fluorine-substituted;

and the diastereomers, enantiomers, metabolites, salts, solvates or solvates of the salts thereof for treatment and/or prophylaxis of autoimmune disorders which are mediated by IRAK4, especially for treatment and prophylaxis of multiple sclerosis, systemic lupus erythematosus, psoriasis, arthritis (psoriatic arthritis, Bekhterev's disease, rheumatoid arthritis, reactive arthritis, systemic juvenile idiopathic arthritis), chronic-inflammatory bowel disorders (Crohn's disease, ulcerative colitis), atopic dermatitis and allergic eczema.

Particular preference is also given to the use of compounds of the general formula (I) in which $R^1$ is a $C_2$-$C_5$-alkyl radical substituted by hydroxyl or $C_1$-$C_3$-alkoxy or trifluoromethoxy or 2,2,2-trifluoroethoxy or trifluoromethyl or is a methyl-$SO_2$-substituted $C_2$-$C_4$-alkyl radical or is an oxetan-3-yl-substituted $C_1$-$C_2$-alkyl radical;

$R^2$ and $R^3$ always have the same definition and are both hydrogen or methyl;

$R^4$ is methyl, ethyl, trifluoro-$C_1$-$C_3$-alkyl, difluoro-$C_1$-$C_3$-alkyl, hydroxymethyl, 1-hydroxyethyl, 2-hydroxypropan-2-yl and 2,2,2-trifluoro-1-hydroxyethyl and $R^5$ is hydrogen, fluorine or methyl;

and the diastereomers, enantiomers, metabolites, salts, solvates or solvates of the salts thereof for treatment and/or prophylaxis of autoimmune disorders which are mediated by IRAK4, especially for treatment and prophylaxis of multiple sclerosis, systemic lupus erythematosus, psoriasis, arthritis (psoriatic arthritis, Bekhterev's disease, rheumatoid arthritis, reactive arthritis, systemic juvenile idiopathic arthritis), chronic-inflammatory bowel disorders (Crohn's disease, ulcerative colitis), atopic dermatitis and allergic eczema.

Very particular preference is given to the use of compounds in which $R^1$ is 4,4,4-trifluorobutyl, 3-hydroxy-3-methylbutyl, 3-hydroxybutyl, 3-methoxypropyl, 3-hydroxypropyl, 3-hydroxy-2-methylpropyl, 3-hydroxy-2,2-dimethylpropyl, 3-trifluoromethoxypropyl, 2-methoxyethyl, 2-hydroxyethyl, 2-(methylsulphonyl)ethyl or 3-(methylsulphonyl)propyl;

$R^2$ and $R^3$ are both methyl or hydrogen and
$R^4$ is difluoromethyl, trifluoromethyl or methyl and
$R^5$ is hydrogen or fluorine;

and the diastereomers, enantiomers, metabolites, salts, solvates or solvates of the salts thereof for treatment and/or prophylaxis of autoimmune disorders which are mediated by IRAK4, especially for treatment and prophylaxis of multiple sclerosis, systemic lupus erythematosus, psoriasis, arthritis (psoriatic arthritis, Bekhterev's disease, rheumatoid arthritis, reactive arthritis, systemic juvenile idiopathic arthritis), chronic-inflammatory bowel disorders (Crohn's disease, ulcerative colitis), atopic dermatitis and allergic eczema.

Very particular preference is also given to the use of compounds in which $R^1$ is 3-hydroxy-3-methylbutyl, 3-hydroxybutyl, 3-hydroxy-2-methylpropyl, 3-hydroxy-2,2-dimethylpropyl, 3-(methylsulphonyl)propyl or 2-(methylsulphonyl)ethyl;
$R^2$ and $R^3$ are both methyl;
$R^4$ is difluoromethyl or trifluoromethyl; and
$R^5$ is hydrogen;

and the diastereomers, enantiomers, metabolites, salts, solvates or solvates of the salts thereof for treatment and/or prophylaxis of autoimmune disorders which are mediated by IRAK4, especially for treatment and prophylaxis of multiple sclerosis, systemic lupus erythematosus, psoriasis, arthritis (psoriatic arthritis, Bekhterev's disease, rheumatoid arthritis, reactive arthritis, systemic juvenile idiopathic arthritis), chronic-inflammatory bowel disorders (Crohn's disease, ulcerative colitis), atopic dermatitis and allergic eczema.

Particular preference is additionally also given to the use of compounds in which $R^1$ is 3-hydroxy-3-methylbutyl, 3-hydroxybutyl, 3-hydroxy-2-methylpropyl, 3-hydroxy-2,2-dimethylpropyl, 3-(methylsulphonyl)propyl or 2-(methylsulphonyl)ethyl;
$R^2$ and $R^3$ are both methyl;
$R^4$ is methyl and
$R^5$ is fluorine, where $R^5$ is in the ortho position to $R^4$;

and the diastereomers, enantiomers, metabolites, salts, solvates or solvates of the salts thereof for treatment and/or prophylaxis of autoimmune disorders which are mediated by IRAK4, especially for treatment and prophylaxis of multiple sclerosis, systemic lupus erythematosus, psoriasis, arthritis (psoriatic arthritis, Bekhterev's disease, rheumatoid arthritis, reactive arthritis, systemic juvenile idiopathic arthritis), chronic-inflammatory bowel disorders (Crohn's disease, ulcerative colitis), atopic dermatitis and allergic eczema.

The present invention especially provides the use of following compounds for treatment and/or prophylaxis of autoimmune disorders which are mediated by IRAK4:

1) N-[6-(2-Hydroxypropan-2-yl)-2-(2-methoxyethyl)-2H-indazol-5-yl]-6-(trifluoromethyl)pyridine-2-carboxamide
2) N-[6-(Hydroxymethyl)-2-(2-methoxyethyl)-2H-indazol-5-yl]-6-(trifluoromethyl)pyridine-2-carboxamide
3) N-[6-(2-Hydroxypropan-2-yl)-2-(3-methoxypropyl)-2H-indazol-5-yl]-6-(trifluoromethyl)pyridine-2-carboxamide
4) N-[6-(Hydroxymethyl)-2-(3-methoxypropyl)-2H-indazol-5-yl]-6-(trifluoromethyl)pyridine-2-carboxamide
5) N-[2-(2-Hydroxyethyl)-6-(2-hydroxypropan-2-yl)-2H-indazol-5-yl]-6-(trifluoromethyl)pyridine-2-carboxamide
6) N-[6-(2-Hydroxypropan-2-yl)-2-(3-hydroxypropyl)-2H-indazol-5-yl]-6-(trifluoromethyl)pyridine-2-carboxamide
7) N-[2-(2-Hydroxyethyl)-6-(hydroxymethyl)-2H-indazol-5-yl]-6-(trifluoromethyl)pyridine-2-carboxamide
8) N-[6-(2-Hydroxypropan-2-yl)-2-(oxetan-3-ylmethyl)-2H-indazol-5-yl]-6-(trifluoromethyl)pyridine-2-carboxamide
9) N-[6-(Hydroxymethyl)-2-(oxetan-3-ylmethyl)-2H-indazol-5-yl]-6-(trifluoromethyl)pyridine-2-carboxamide
10) N-{6-(2-Hydroxypropan-2-yl)-2-[3-(methylsulphonyl)propyl]-2H-indazol-5-yl}-6-(trifluoromethyl)pyridine-2-carboxamide
11) N-[2-(3-Hydroxy-3-methylbutyl)-6-(2-hydroxypropan-2-yl)-2H-indazol-5-yl]-6-(trifluoromethyl)pyridine-2-carboxamide
12) N-{6-(2-Hydroxypropan-2-yl)-2-[2-(methylsulphonyl)ethyl]-2H-indazol-5-yl}-6-(trifluoromethyl)pyridine-2-carboxamide
13) 6-(Difluoromethyl)-N-[2-(3-hydroxy-3-methylbutyl)-6-(2-hydroxypropan-2-yl)-2H-indazol-5-yl]pyridine-2-carboxamide
14) 6-(Difluoromethyl)-N-{6-(2-hydroxypropan-2-yl)-2-[2-(methylsulphonyl)ethyl]-2H-indazol-5-yl}pyridine-2-carboxamide
15) 6-(Difluoromethyl)-N-[6-(2-hydroxypropan-2-yl)-2-(3-hydroxypropyl)-2H-indazol-5-yl]pyridine-2-carboxamide
16) N-[6-(2-Hydroxypropan-2-yl)-2-(4,4,4-trifluorobutyl)-2H-indazol-5-yl]-6-(trifluoromethyl)pyridine-2-carboxamide
17) N-{6-(2-Hydroxypropan-2-yl)-2-[3-(trifluoromethoxy)propyl]-2H-indazol-5-yl}-6-(trifluoromethyl)pyridine-2-carboxamide
18) N-{6-(2-Hydroxypropan-2-yl)-2-[3-(2,2,2-trifluoroethoxy)propyl]-2H-indazol-5-yl}-6-(trifluoromethyl)pyridine-2-carboxamide
19) 5-Fluoro-N-[2-(3-hydroxy-3-methylbutyl)-6-(2-hydroxypropan-2-yl)-2H-indazol-5-yl]-6-methylpyridine-2-carboxamide
20) N-[2-(3-Hydroxy-3-methylbutyl)-6-(2-hydroxypropan-2-yl)-2H-indazol-5-yl]-6-methylpyridine-2-carboxamide
21) 6-(2-Hydroxypropan-2-yl)-N-[6-(2-hydroxypropan-2-yl)-2-(4,4,4-trifluorobutyl)-2H-indazol-5-yl]pyridine-2-carboxamide
22) N-{2-[2-(1-Hydroxycyclopropyl)ethyl]-6-(2-hydroxypropan-2-yl)-2H-indazol-5-yl}-6-(trifluoromethyl)pyridine-2-carboxamide.

The invention further provides for the use of the above-mentioned compounds 1) to 22) for treatment and/or prophylaxis of multiple sclerosis, systemic lupus erythematosus, psoriasis, arthritis (psoriatic arthritis, Bekhterev's disease, rheumatoid arthritis, reactive arthritis, systemic juvenile idiopathic arthritis), chronic-inflammatory bowel disorders (Crohn's disease, ulcerative colitis), atopic dermatitis and allergic eczema.

The invention further provides for the use of compounds of the general formula (III)

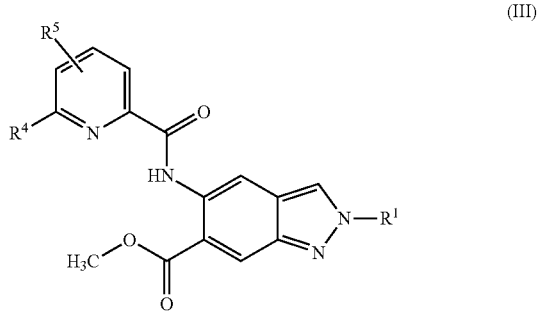

(III)

in which

R¹ is 4,4,4-trifluorobutyl, 3-hydroxy-3-methylbutyl, 3-methoxypropyl, 3-hydroxypropyl, 3-hydroxybutyl, 3-hydroxy-2-methylpropyl, 3-hydroxy-2,2-dimethylpropyl, 3-trifluoromethoxypropyl, 2-methoxyethyl, 2-hydroxyethyl, 2-(methylsulphonyl)ethyl, 3-(methylsulphonyl)propyl or 2-(1-hydroxycyclopropyl)ethyl;

R⁴ is difluoromethyl, trifluoromethyl or methyl; and

R⁵ is hydrogen or fluorine;

and the diastereomers, enantiomers, metabolites, salts, solvates or solvates of the salts thereof for treatment and/or prophylaxis of autoimmune disorders which are mediated by IRAK4.

A further embodiment of the invention is the use of compounds of the general formula (III), in which R¹, R⁴ and R⁵ are as defined above, for treatment and/or prophylaxis of multiple sclerosis, systemic lupus erythematosus, psoriasis, arthritis (psoriatic arthritis, Bekhterev's disease, rheumatoid arthritis, reactive arthritis, systemic juvenile idiopathic arthritis), chronic-inflammatory bowel disorders (Crohn's disease, ulcerative colitis), atopic dermatitis and allergic eczema.

A likewise further embodiment of the invention is the use of the following compounds of the general formula (III):

methyl 5-{[(5-fluoro-6-methylpyridin-2-yl)carbonyl]amino}-2-(3-hydroxy-3-methylbutyl)-2H-indazole-6-carboxylate and methyl 2-(3-hydroxy-3-methylbutyl)-5-({[6-(trifluoromethyl)pyridin-2-yl]carbonyl}amino)-2H-indazole-6-carboxylate for treatment and/or prophylaxis of autoimmune disorders which are mediated by IRAK4, especially for treatment and/or prophylaxis of multiple sclerosis, systemic lupus erythematosus, psoriasis, arthritis (psoriatic arthritis, Bekhterev's disease, rheumatoid arthritis, reactive arthritis, systemic juvenile idiopathic arthritis), chronic-inflammatory bowel disorders (Crohn's disease, ulcerative colitis), atopic dermatitis and allergic eczema.

The compounds of the general formula (III) are inhibitors of interleukin-1 receptor associated kinase-4 (IRAK4).

The compounds of the general formula (I) act as inhibitors of IRAK4 kinase and have an unforeseeable useful pharmacological activity spectrum.

Thus, in addition to the subject matter mentioned above, the present invention also provides the use of the compounds of the general formula (I) for treatment and/or prophylaxis of diseases in man and animals.

Treatment and/or prophylaxis of autoimmune disorders, such as inflammatory nervous disorders (MS), inflammatory joint disorders (various forms of arthritis), inflammatory skin disorders (psoriasis, atopic dermatitis and allergic eczema), inflammatory bowel disorders (IBD) and multi-organ disorders (SLE) with the inventive IRAK4 inhibitors is particularly preferred.

The compounds of the general formula (I) are suitable for prophylaxis and/or treatment of various disorders and disease-related states, especially disorders mediated by TLR (except for TLR3) and/or the IL-1 receptor family and/or disorders whose pathology is mediated directly by IRAK4. IRAK4-associated disorders include multiple sclerosis, arthritis (psoriatic arthritis, rheumatoid arthritis, Bekhterev's disease, reactive arthritis, systemic juvenile idiopathic arthritis), gout, Vogt-Koyanagi-Harada syndrome, systematic lupus erythematosus, chronic-inflammatory bowel disorders (Crohn's disease, ulcerative colitis), psoriasis, atopic dermatitis and allergic eczema.

The compounds of the general formula (I) can also be used for prophylaxis and/or treatment of disorders mediated by MyD88 and TLR (except for TLR3). This includes multiple sclerosis, rheumatoid arthritis, psoriatic arthritis, reactive arthritis, systemic juvenile idiopathic arthritis, Bekhterev's disease, systemic lupus erythematosus, osteoarthritis, Sjögren syndrome, giant cell arteritis, sepsis, poly- and dermatomyositis, skin disorders such as psoriasis, atopic dermatitis, alopecia areata, allergic eczema, acne inversa and acne vulgaris, chronic-inflammatory bowel disorders such as Crohn's disease and ulcerative colitis.

Because of the mechanism of action of the inventive compounds of the general formula (I), they are suitable for prophylaxis and/or treatment of the TLR-mediated disorders such as rheumatoid arthritis, psoriatic arthritis, reactive arthritis, systemic juvenile idiopathic arthritis, Bekhterev's disease, psoriasis, atopic dermatitis, systemic lupus erythematosus, Behçet's disease, gout. In addition, the inventive compounds of the general formula (I) are suitable for prophylaxis and/or treatment in the case of multiple sclerosis, adult-onset Still's disease, allergic eczema and chronic inflammatory bowel disorders, such as ulcerative colitis and Crohn's disease.

The prophylaxis and/or treatment of pruritus and pain, especially of acute, chronic, inflammatory and neuropathic pain, is also provided by the compounds of the general formula (I).

Moreover, the compounds of the general formula (I) are suitable for the treatment and/or prevention of disorders mediated via the IL-1 receptor family. These disorders include CAPS (cryopyrin-associated periodic syndromes) including FCAS (familial cold autoinflammatory syndrome), MWS (Muckle-Wells syndrome), NOMID (neonatal-onset multisystem inflammatory disease) and CONCA (chronic infantile, neurological, cutaneous, and articular) syndrome, FMF (familial mediterranean fever), HIDS (hyper-IgD syndrome), TRAPS (tumour necrosis factor receptor 1-associated periodic syndrome), juvenile idiopathic arthritis, adult-onset Still's disease, gout, Adamantiades-Behçet's disease, rheumatoid arthritis, psoriasis, arthritis, Bekhterev's disease, reactive arthritis, systematic juvenile idiopathic arthritis, osteoarthritis, keratoconjunctivitis sicca and Sjögren syndrome, multiple sclerosis, systematic lupus erythematosus, alopecia areata, type 1 diabetes mellitus, type 2 diabetes mellitus and the sequelae of myocardial infarction. Pulmonary disorders such as asthma, COPD, idiopathic interstitial pneumonia and ARDS, chronic-inflammatory bowel disorders such as Crohn's disease and ulcerative colitis are associated with dysregulation of the IL-1 receptor family and are suitable for therapeutic and/or prophylactic use of the compounds of the general formula (I).

The compounds of the general formula (I) can also be used for treatment and/or prevention of IL-1 receptor family-mediated neurological disorders such as multiple sclerosis and dermatological disorders such as psoriasis, atopic dermatitis, acne inversa, alopecia areata and allergic contact dermatitis.

In addition, the compounds of the general formula (I) are suitable for the treatment and/or prophylaxis of pain disorders, especially of acute, chronic, inflammatory and neuropathic pain. This preferably includes hyperalgesia, allodynia, pain from arthritis (such as osteoarthritis, rheumatoid arthritis, psoriatic arthritis, Bekhterev's disease and reactive arthritis, systemic juvenile idiopathic arthritis), post-operative pain, pain caused by spinal cord injuries, inflammation-induced pain, lower back pain and chronic pain.

The present invention further also provides a method for treatment and/or prevention of disorders, especially the disorders mentioned above, using an effective amount of at least one of the compounds of the general formula (I).

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

With reference to autoimmune disorders mediated by IRAK4, for the purpose of the present invention "prevention", "prophylaxis" or "preclusion" is to be understood as meaning a maintenance therapy after remission of the disorder for preventing a recidivism (relapse). This means that a new acute inflammatory episode can be prevented or at least delayed.

"Remission of a disorder" is to be understood as meaning temporary or permanent ceasing of disease symptoms of a physical or psychic nature but without achieving permanent recovery.

"Recidivism" or "relapse" is to be understood as meaning the reoccurrence of a disease or its symptoms after a treatment which was temporarily successful, or after spontaneous remission.

The treatment or prevention of a disease, a condition, a disorder, an injury or a health problem may be partial or complete.

The compounds of the general formula (I) can be used alone or, if required, in combination with other active ingredients. The present invention further provides medicaments containing at least one of the compounds of the general formula (I) and one or more further active ingredients, especially for treatment and/or prevention of the above-mentioned disorders. Preferred examples of active ingredients suitable for combinations include:

General mention may be made of active ingredients such as antibacterial (e.g. penicillins, vancomycin, ciprofloxacin, mupirocin), antiviral (e.g. aciclovir, oseltamivir) and antimycotic (e.g. naftifin, nystatin) substances, gamma globulins, immunomodulatory and immunosuppressive compounds such as cyclosporine, Methotrexat®, TNF blockers (e.g. Humira®, etanercept, infliximab, golimumab and certolizumab pegol), IL-1 inhibitors (e.g. anakinra, canakinumab, rilonacept), phosphodiesterase inhibitors (e.g. apremilast), Jak/STAT in general (e.g. tofacitinib, baricitinib, GLPG0634), leflunomide, fingolimod, teriflunomide, dimethyl fumarates (e.g. tecfidera), IL-6 antagonists (Actemra, sarilumab), IL-2 inhibitors (e.g. Stelara), glatiramer acetate (e.g. Copaxone, Glatopa), Tysabri, cyclophosphamide, rituximab, belimumab, calcineurin inhibitors (e.g. tacrolimus), rapamycin, mycophenolate mofetil, interferons (e.g. betaferon), corticosteroids/glucocorticoids (e.g. prednisone, prednisolone, dexamethasone, methylprednisolone, hydrocortisone, betamethasone), cyclophosphamide, azathioprine and sulfasalazine; paracetamol, antihistamines (e.g. azelastine in Allergodil®, hydroxyzine in Atarax®, clemastine in Tavegil®), non-steroidal anti-inflammatory substances (NSAIDS) (aspirin, ibuprofen, naproxen, etodolac, celecoxib, colchicine).

In addition to those mentioned above, the inventive IRAK4 inhibitors can also be combined with the following active ingredients:

6-mercaptopurine, ACE inhibitors (e.g. benazepril), acetylcholinesterase inhibitors (e.g. donepezil), angiotensin receptor blockers (e.g. losartan, valsartan), anion exchangers (e.g. colestyramin, colestipol, colesevelam), antibiotics such as, for example, ciprofloxacin and metronidazol, anti-CD3 antibodies, anticholinergics (e.g. glycopyrronium), antidiabetics such as, for example, metformin, antidiarrheal drugs such as, for example, loperamide or laxatives (bisacodyl), anticonvulsive drugs (e.g. gabapentin); anti-T-lymphocyte globulin/antilymphocyte globulin, apremilast, azathioprine, basiliximab, belimumab, beta-2 sympathomimetics (e.g. salbutamol), beta-blockers (e.g. metoprolol), beta-interferon (IFN-beta) (e.g. IFN beta-1b, IFN beta-1a Avonex® and Betaferon®), biologics for B cell and T cell therapy (e.g. rituximab, abatacept), calcineurine inhibitors (e.g. tacrolimus), calcium channel blockers (e.g. nifedipine), chloroquin, cortisone, cyclophosphamide, cyclosporin, daclizumab, dithranol, diuretics (e.g. hydrochlorothiazide), DPP-4 (dipeptidyl peptidase 4) inhibitors (e.g. linagliptin, saxagliptin, sitagliptin, vildagliptin), ezetimib, statins (e.g. simvastatin, fluvastatin), fibrates (e.g. bezafibrate, etofibrate, fenofibrate, gemfibrozil), fingolimod, fumarates (dimethyl fumarates), glatiramer acetate, glinides (e.g. nateglinide), glucocorticoids, urea, hydroxychloroquine, IgE antibodies, immunoglobulines, immunosuppressive drugs such as mitoxantrone, azathioprine and cyclophosphamide, incretin mimetics (hormone glucose-dependent insulinotropic peptide (GIP)- and glucagon-like peptide 1 (GLP-1)-analogues/agonists) (e.g. exenatide, liraglutide, lixisenatide), insulin sensitizers (e.g. pioglitazone) and insulin therapy (e.g. NPH insulin, insulin lispro), interferons, integrin antibodies (e.g. vedolizumab, natalizumab), Jak/STAT inhibitors (e.g. tofacitinib, baricitinib, GLPG0634), cortisol-containing preparations, leukotriene receptor antagonists (e.g. montelukast), leflunomide, MAO (monoaminooxidase) inhibitors (e.g. selegiline), mesalazine, methotrexate, methylxanthines (e.g. theophylline), natalizumab, nicotinic acid derivatives (e.g. nicotinic acid/laropiprant), PDE-4 (phosphodiesterase type 4) inhibitors (e.g. roflumilast), phototherapy, probiotic bacteria (Mutaflor, VSL #3®, Lactobacillus GG, Lactobacillus plantarum, L. acidophilus, L. casei, Bifidobacterium infantis 35624, Enterococcus fecium SF68, Bifidobacterium longum, Escherichia coli Nissle 1917), rapamycin, retinoid, rituximab, salicylic acid, secukinumab, SGLT2 (sodium/glucose cotransporter 2) inhibitors/gliflozin (e.g. dapagliflozin, empagliflozin), statins (e.g. simvastatin, fluvastatin), sulfasalazine, sulfonyl ureas (e.g. glibenclamide, tolbutamide), teriflunomide, tocilizumab, topic steroids, ustekinumab, vedolizumab, vitamin D3 analogues such as, for example, calcipotriol, tacalcitol or calcitriol; cell division inhibitors (e.g. azathioprine, mycophenolate mofetil, mycophenolic acid, everolimus or sirolimus) and α-glucosidase inhibitors (e.g. acarbose, miglitol, voglibiose).

Mention should also be made of medicaments comprising at least one of the compounds of the general formula (I) and one or more further active ingredients, especially EP4 inhibitors (prostaglandin E2 receptor 4 inhibitors), P2×3 inhibitors (P2X purinoceptor 3), PTGES inhibitors (prostaglandin E synthase inhibitors), P2×4 inhibitors (P2X purinoceptor 4), MKNK1/2 inhibitors (MAP kinase-interacting serine/threonine-protein kinase 1/2) or AKR1C3 inhibitors (aldo-keto reductase family 1 member C3 inhibitors), for treatment and/or prevention of the aforementioned disorders.

The compounds of the general formula (I) can act systemically and/or locally. For this purpose, they can be administered in a suitable manner, for example by the oral, parenteral, subcutaneous, intraarticular, pulmonal, nasal, sublingual, lingual, buccal, rectal, dermal, transdermal or conjunctival route, via the ear or as an implant or stent.

The compounds of the general formula (I) can be administered in administration forms suitable for these administration routes.

Suitable administration forms for oral administration are those which work according to the prior art and release the compounds of the general formula (I) rapidly and/or in a modified manner and which contain the compounds of the general formula (I) in crystalline and/or amorphous and/or dissolved form, for example tablets (uncoated or coated tablets, for example with gastric juice-resistant or retarded-dissolution or insoluble coatings which control the release of the inventive compound), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can be accomplished with avoidance of a resorption step (for example by an intravenous, intraarterial, intraarticular, intracardiac, intraspinal or intralumbar route) or with inclusion of a resorption (for example by an intramuscular, subcutaneous, intracutaneous, percutaneous or intraperitoneal route). Administration forms suitable for parenteral administration include preparations for injection and infusion in the form of solutions, suspensions, emulsions, lyophilizates or sterile powders.

For the other administration routes, suitable examples are inhalable medicament forms (including powder inhalers, nebulizers), nasal drops, solutions or sprays, tablets, films/oblates or capsules for lingual, sublingual or buccal administration, suppositories, ear or eye preparations, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral or parenteral administration, especially oral administration.

The compounds of the general formula (I) can be converted to the administration forms mentioned. This can be accomplished in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersing or wetting agents (for example sodium dodecylsulphate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavour and/or odour correctants.

The present invention further provides medicaments which comprise at least one inventive compound, typically together with one or more inert, nontoxic, pharmaceutically suitable excipients, and the use thereof for the aforementioned purposes.

In general, it has been found to be advantageous in the case of parenteral administration to administer amounts of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg of body weight.

It may nevertheless be necessary in some cases to deviate from the stated amounts, specifically as a function of the body weight, route of administration, individual response to the active ingredient, nature of the preparation and time or interval over which administration takes place. Thus in some cases it may be sufficient to manage with less than the abovementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

Unless stated otherwise, the percentages in the tests and examples which follow are percentages by weight; parts are parts by weight. Solvent ratios, dilution ratios and concentration data for the liquid/liquid solutions are based in each case on volume.

Preparation of the Compounds of the General Formula (I)

The compounds which are described in the present application, and the preparation thereof, are presented in the as-yet unpublished application PCT/EP2015/077596.

The preparation of the compounds of the general formula (I) is illustrated by the synthesis schemes which follow.

Starting materials used for synthesis of the compounds of the general formula (I) are carboxylic acids (Intermediate V3), which are commercially available or can be prepared by routes known from the literature or analogously to routes known from the literature (see, for example, European Journal of Organic Chemistry 2003, 8, 1559-1568, Chemical and Pharmaceutical Bulletin, 1990, 38, 9, 2446-2458, Synthetic Communications 2012, 42, 658-666, Tetrahedron, 2004, 60, 51, 11869-11874) (see, for example, Synthesis Scheme 1). Some carboxylic acids V3 can be prepared proceeding from carboxylic esters (Intermediate V2) by hydrolysis (cf., for example, the reaction of ethyl 6-(hydroxymethyl)pyridine-2-carboxylate with aqueous sodium hydroxide solution in methanol, WO200411328) or—in the case of a tert-butyl ester—by reaction with an acid, for example hydrogen chloride or trifluoroacetic acid (cf., for example, Dalton Transactions, 2014, 43, 19, 7176-7190). The carboxylic acids V3 can also be used in the form of their alkali metal salts. The Intermediates V2 can optionally also be prepared from the Intermediates V1 which bear a chlorine, bromine or iodine as substituent $X^1$ by reaction in a carbon monoxide atmosphere, optionally under elevated pressure, in the presence of a phosphine ligand, for example 1,3-bis(diphenylphosphino)propane, a palladium compound, for example palladium(II) acetate, and a base, for example triethylamine, with addition of ethanol or methanol in a solvent, for example dimethyl sulphoxide (for preparation methods see, for example, WO2012112743, WO 2005082866, Chemical Communications (Cambridge, England), 2003, 15, 1948-1949, WO200661715). The Intermediates V1 are either commercially available or can be prepared by routes known from the literature. Illustrative preparation methods are detailed in WO 2012061926, European Journal of Organic Chemistry, 2002, 2, 327-330, Synthesis, 2004, 10, 1619-1624, Journal of the American Chemical Society, 2013, 135, 32, 12122-12134, Bioorganic and Medicinal Chemistry Letters, 2014, 24, 16, 4039-4043, US2007185058, WO2009117421.

Synthesis Scheme 1

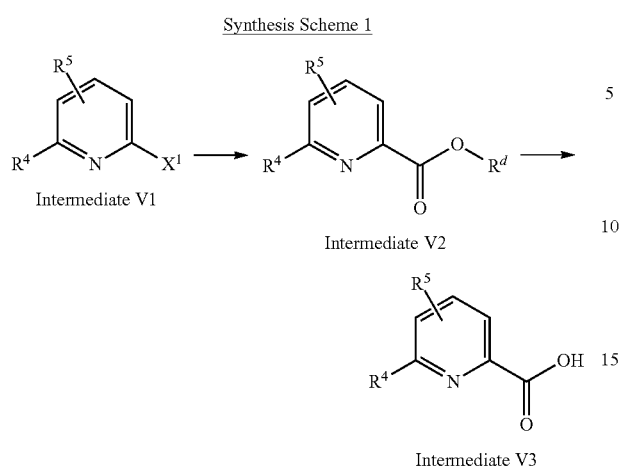

$X^1$ is chlorine, bromine or iodine.

$R^d$ is methyl, ethyl, benzyl or tert-butyl.

$R^4$, $R^5$ are each as defined in the general formula (I).

Methyl 5-amino-1H-indazole-6-carboxylate (Intermediate 2) can be obtained proceeding from methyl 1H-indazole-6-carboxylate (Intermediate 0) according to Synthesis Scheme 2 by nitration and reduction of the nitro group of Intermediate 1 with hydrogen in the presence of palladium on charcoal analogously to WO 2008/001883. For preparation of the Intermediates 3 proceeding from Intermediate 2, it is possible to use various coupling reagents known from the literature (Amino Acids, Peptides and Proteins in Organic Chemistry, Vol. 3—Building Blocks, Catalysis and Coupling Chemistry, Andrew B. Hughes, Wiley, Chapter 12—Peptide-Coupling Reagents, 407-442; Chem. Soc. Rev., 2009, 38, 606). For example, it is possible to use 1-(3-dimethylaminopropyl)-3-ethylcarbodiimide hydrochloride in combination with 1-hydroxy-1H-benzotriazole hydrate (HOBt, WO2012107475; Bioorg. Med. Chem. Lett., 2008, 18, 2093), (1H-benzotriazol-1-yloxy)(dimethylamino)-N,N-dimethylmethaniminium tetrafluoroborate (TBTU, CAS 125700-67-6), (dimethylamino)-N,N-dimethyl(3H-[1,2,3]triazolo[4,5-b]pyridin-3-yloxy)methanaminium hexafluorophosphate (HATU, CAS 148893-10-1), propanephosphonic anhydride (as solution in ethyl acetate or DMF, CAS68957-94-8) or di-1H-imidazol-1-ylmethanone (CDI) as coupling reagents, with addition of a base such as triethylamine or N-ethyl-N-isopropylpropan-2-amine in each case to the reaction mixture. Preference is given to the use of TBTU and N-ethyl-N-isopropylpropan-2-amine in THF.

Synthesis Scheme 2

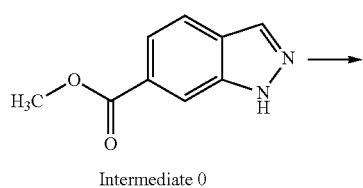

Intermediate 0

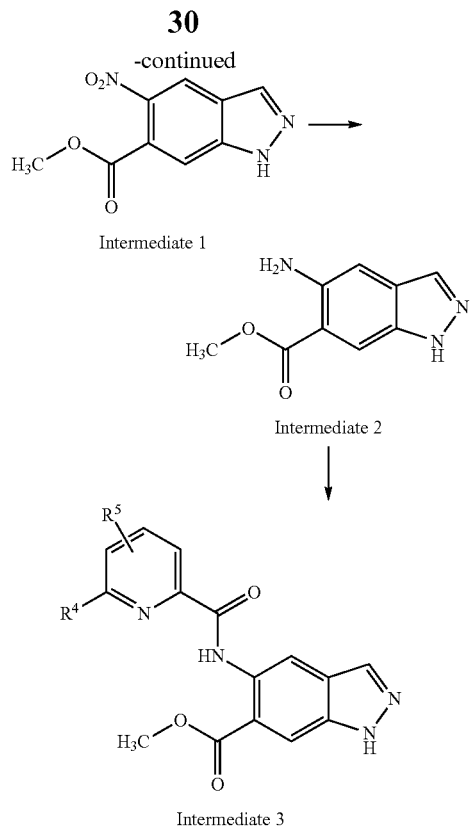

The substituents $R^4$, $R^5$ are each as defined in the general formula (I).

Proceeding from the Intermediates 3, it is possible to prepare 2-substituted indazole derivatives (Intermediate 4) (see synthesis scheme 3). Useful reactions for this purpose include those with optionally substituted alkyl chlorides, alkyl bromides, alkyl iodides or alkyl 4-methylbenzenesulphonates. The alkyl halides or alkyl 4-methylbenzenesulphonates used are commercially available or can be prepared analogously to routes known from literature (for the preparation of alkyl 4-methylbenzenesulphonates, one example is the reaction of an appropriate alcohol with 4-methylbenzenesulphonyl chloride in the presence of triethylamine or pyridine; see, for example, Bioorganic and Medicinal Chemistry, 2006, 14, 12 4277-4294). Optionally, in the case of use of alkyl chlorides or alkyl bromides, it is also possible to add an alkali metal iodide such as potassium iodide or sodium iodide. Bases used may, for example, be potassium carbonate, caesium carbonate or sodium hydride. In the case of reactive alkyl halides, it is also possible in some cases to use N-cyclohexyl-N-methylcyclohexanamine. Useful solvents include, for example, 1-methylpyrrolidin-2-one, DMF, DMSO or THF. Optionally, the alkyl halides or alkyl 4-methylbenzenesulphonates used may have functional groups which have optionally been protected with a protecting group beforehand (see also P. G. M. Wuts, T. W. Greene, Greene's Protective Groups in Organic Synthesis, Fourth Edition, ISBN: 9780471697541). If, for example, alkyl halides or alkyl 4-methylbenzenesulphonates having one or more hydroxyl groups are used, these hydroxyl groups may optionally be protected by a tert-butyl(dimethyl)silyl group or a similar silicon-containing protecting group familiar to those skilled in the art. Alternatively, the hydroxyl groups may also be protected by the tetrahydro-2H-pyran (THP) group or by the acetyl or benzoyl group. The protecting groups used can then be detached subsequently to the synthesis of Intermediate 4, or else after the synthesis of (I). If, for example, a tert-butyl(dimethylsilyl) group is used as protecting group, it can be detached using tetrabutylammonium fluoride in a solvent such as THF, for example. A THP protecting group can be detached, for example, using 4-methylbenzenesulphonic acid (optionally in monohydrate form). Acetyl groups or benzoyl groups can be detached by treatment with aqueous sodium hydroxide solution.

Optionally, the alkyl halides or alkyl 4-methylbenzenesulphonates used may contain functional groups which can be converted by oxidation or reduction reactions known to those skilled in the art (see, for example, *Science of Synthesis*, Georg Thieme Verlag). If, for example, the functional group is a sulphide group, this can be oxidized by methods known in the literature to a sulphoxide or sulphone group. In the case of a sulphoxide group, this can likewise be oxidized to a sulphone group. For these oxidation steps, it is possible to use, for example, 3-chloroperbenzoic acid (CAS 937-14-4) (in this regard, see also, for example, US201094000 for the oxidation of a 2-(methylsulphanyl)ethyl-1H-pyrazole derivative to a 2-(methylsulphinyl)ethyl-1H-pyrazole derivative and the oxidation of a further 2-(methylsulphanyl) ethyl-1H-pyrazole derivative to a 2-(methylsulphonyl)ethyl-1H-pyrazole derivative). If the alkyl halides or tosylates used contain a keto group, this can be reduced by reduction methods known to those skilled in the art to an alcohol group (see, for example, Chemische Berichte, 1980, 113, 1907-1920 for the use of sodium borohydride).

These oxidation or reduction steps can be effected subsequently to the synthesis of Intermediate 4, or else after the synthesis of the compounds of the general formula (I). Alternatively, Intermediate 4 can be prepared via Mitsunobu reaction (see, for example, K. C. K. Swamy et. al. Chem. Rev. 2009, 109, 2551-2651) of Intermediate 3 with optionally substituted alkyl alcohols. It is possible to utilize various phosphines such as triphenylphosphine, tributylphosphine or 1,2-diphenylphosphinoethane in combination with diisopropyl azodicarboxylate (CAS 2446-83-5) or further diazene derivatives mentioned in the literature (K. C. K. Swamy et. al. Chem. Rev. 2009, 109, 2551-2651). Preference is given to the use of triphenylphosphine and diisopropyl azodicarboxylate. If the alkyl alcohol bears a functional group it is possible—as in the case of the abovementioned reactions with alkyl halides—for known protecting group strategies (further pointers can be found in P. G. M. Wuts, T. W. Greene, Greene's Protective Groups in Organic Synthesis, Fourth Edition, ISBN: 9780471697541) and—as in the case of the abovementioned reactions with alkyl halides—for oxidation or reduction steps to be effected correspondingly to the synthesis of Intermediate 4, or else after the synthesis of the compounds of the general formula (I). Proceeding from Intermediate 4, inventive compounds of the general formula (I) where $R^2$ and $R^3$ are defined as $C_1$-$C_6$-alkyl (where $R^2$ and $R^3$ have the same definition) may be obtained by a Grignard reaction (cf., for example, the reaction of a methyl 1H-indazole-6-carboxylate derivative with methylmagnesium bromide in EP 2489663). For the Grignard reaction, it is possible to use alkylmagnesium halides. Particular preference is given to methylmagnesium chloride or methylmagnesium bromide in THF or diethyl ether, or else in mixtures of THF and diethyl ether. Alternatively, proceeding from Intermediate 4, compounds of the general formula (I) where $R^2$ and $R^3$ are defined as $C_1$-$C_6$-alkyl (where $R^2$ and $R^3$ have the same definition) may be obtained by a reaction with an alkyllithium reagent (cf., for example, the reaction of a methyl 2-amino-4-chloro-1-methyl-1H-benzimidazole-7-carboxylate derivative with isopropyllithium or tert-butyllithium in WO2006116412). Proceeding from Intermediate 4, it is possible to prepare compounds of the general formula (I) where $R^2$ and $R^3$ are defined as H by reduction with lithium aluminium hydride in THF, lithium borohydride in THF or sodium borohydride in THF, optionally with addition of methanol, or mixtures of lithium borohydride and sodium borohydride.

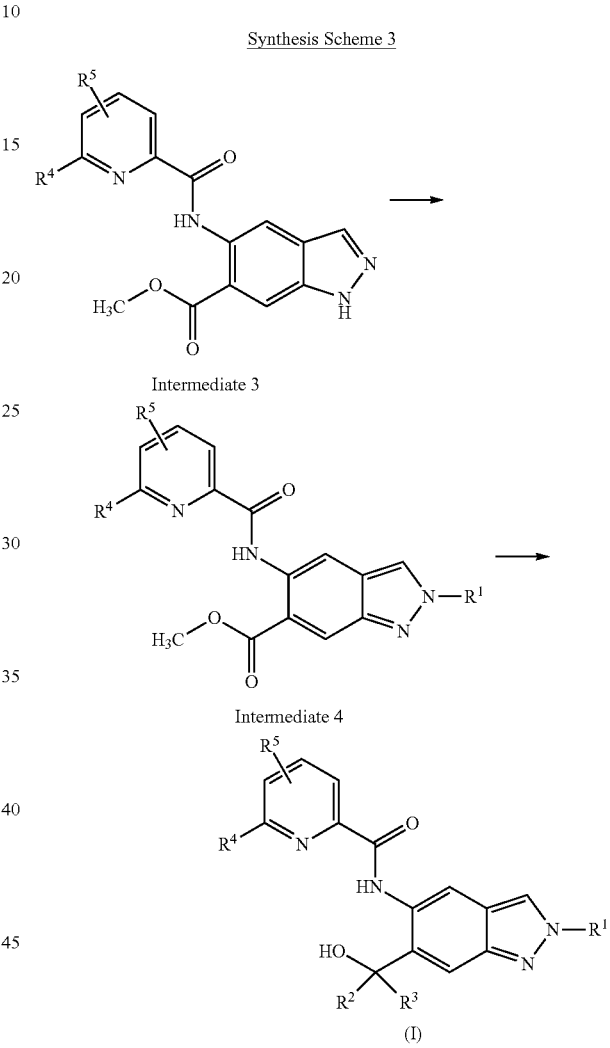

Synthesis Scheme 3

Intermediate 3

Intermediate 4

(I)

The substituents $R^1$, $R^2$, $R^3$, $R^4$, $R^5$ are each as defined in the general formula (I).

Proceeding from Intermediate 3, Intermediate 5 where $R^2$ and $R^3$ are defined as $C_1$-$C_6$-alkyl (where $R^2$ and $R^3$ have the same definition) may be obtained by a Grignard reaction (cf., for example, Synthesis Scheme 4). For this purpose, it is possible to use suitable alkylmagnesium halides, for example methylmagnesium chloride or methylmagnesium bromide in THF or in diethyl ether or else in mixtures of THF and diethyl ether.

Proceeding from Intermediate 5, it is then possible to prepare a portion (I-a) of the compounds of the general formula (I) where $R^2$ and $R^3$ are defined as $C_1$-$C_6$-alkyl (where $R^2$ and $R^3$ have the same definition). For this purpose, analogously to Synthesis Scheme 3 (preparation of Intermediate 3), useful reactions are those of Intermediate 5 with optionally substituted alkyl chlorides, alkyl bromides, alkyl iodides or alkyl 4-methylbenzenesulphonates. It is possible to use protecting group strategies analogously to those described in Synthesis Scheme 3.

Alternatively, for preparation of a portion (I-a) of the compounds of general formula (I) where $R^2$ and $R^3$ are defined as $C_1$-$C_6$-alkyl (where $R^2$ and $R^3$ have the same definition), it is possible to use the Mitsunobu reaction of Intermediate 5 with optionally substituted alkyl alcohols (analogously to Synthesis Scheme 3).

If $R^1$ in the compounds of the formula (I-a) includes a suitable functional group, it is optionally possible subsequently, in analogy to Synthesis Scheme 3, to use oxidation or reduction reactions for preparation of further inventive compounds.

Intermediate 6 by methods as in Synthesis Scheme 3 (preparation of Intermediate 4 from Intermediate 3).

Intermediate 6 can then be converted to Intermediate 7 by reduction of the nitro group. For example, the nitro group can be reduced with palladium on carbon under a hydrogen atmosphere (cf., for example, WO2013174744 for the reduction of 6-isopropoxy-5-nitro-1H-indazole to 6-isopropoxy-1H-indazol-5-amine) or by the use of iron and ammonium chloride in water and ethanol (see, for example, also Journal of the Chemical Society, 1955, 2412-2419), or by the use of tin(II) chloride (CAS 7772-99-8). The use of iron and ammonium chloride in water and ethanol is preferred. The preparation of Intermediate 4 from Intermediate 7 can be effected analogously to Synthesis Scheme 2 (preparation of Intermediate 3 from Intermediate 2).

As described for Synthesis Scheme 3, it is optionally possible to use protecting group strategies in the case of Synthesis Scheme 5 as well. Optionally, it is additionally possible, proceeding from Intermediate 6 or Intermediate 7, as described for Synthesis Scheme 3, to conduct oxidation or reduction reactions known to those skilled in the art (cf., for example *Science of Synthesis*, Georg Thieme Verlag).

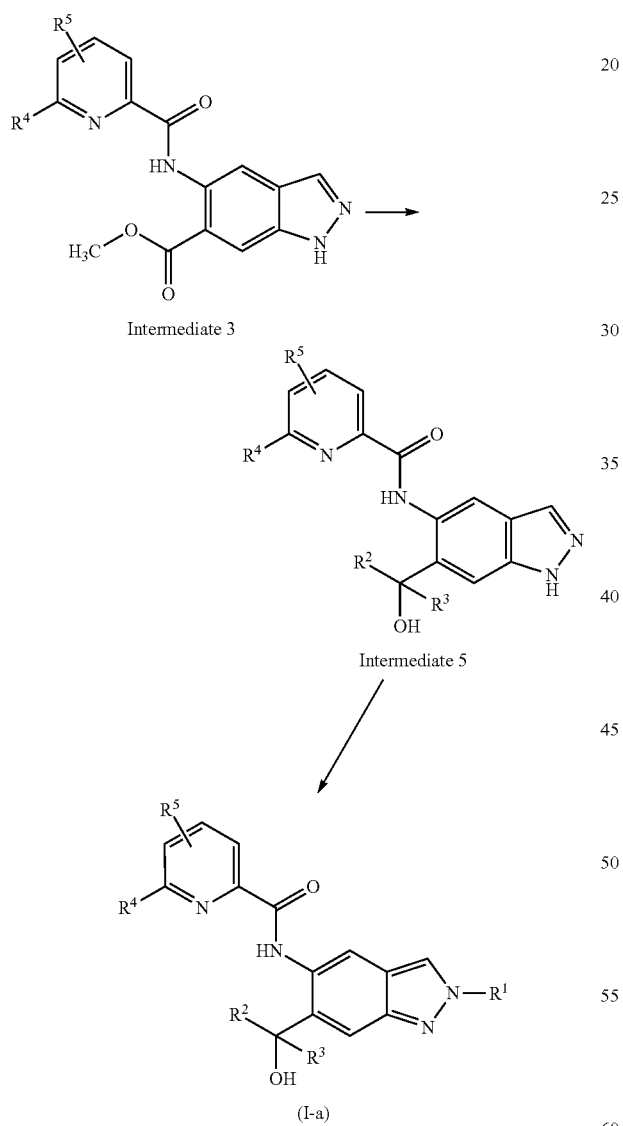

Synthesis Scheme 4

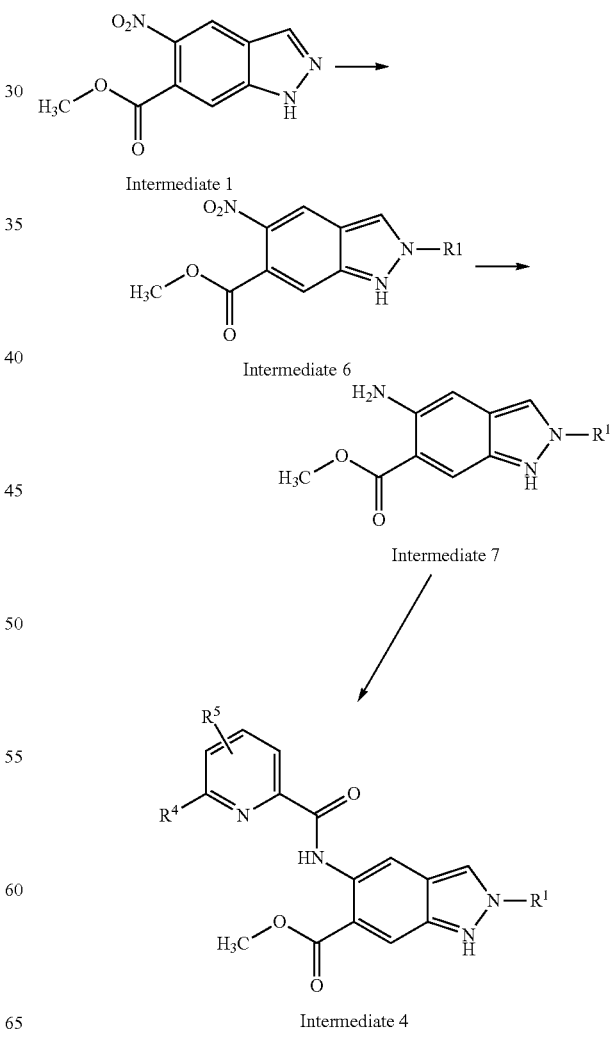

Synthesis Scheme 5

The substituents $R^1$, $R^4$, $R^5$ are each as defined in the general formula (I). $R^2$ and $R^3$ always have the same definition and are both $C_1$-$C_6$-alkyl.

Proceeding from Intermediate 1, it is possible to prepare Intermediate 4 in an alternative manner (see Synthesis Scheme 5). First of all, Intermediate 1 is converted to The substituents $R^1$, $R^4$, $R^5$ are each as defined in the general formula (I).

SYNTHESIS OF THE EXAMPLE COMPOUNDS

Abbreviations and Elucidations

| | |
|---|---|
| DMF | N,N-dimethylformamide |
| DMSO | dimethyl sulphoxide |
| THF | tetrahydrofuran |
| RT | room temperature |
| HPLC | high-performance liquid chromatography |
| h | hour(s) |
| HCOOH | formic acid |
| MeCN | acetonitrile |
| min | minute(s) |
| UPLC | ultrahigh-performance liquid chromatography |
| DAD | diode array detector |
| ELSD | evaporating light scattering detector |
| ESI | electrospray ionization |
| SQD | single quadrupole detector |
| CPG | core-pulled precision glass |
| $NH_3$ | ammonia |

The term sodium chloride solution always means a saturated aqueous sodium chloride solution.

The chemical names of the intermediates and examples were generated using the ACD/LABS (Batch Version 12.01.) software.

Methods

In some cases, the compounds of the general formula (I) and precursors and/or intermediates thereof were analysed by LC-MS.

Method A1: UPLC (MeCN—HCOOH):

Instrument: Waters Acquity UPLC-MS SQD 3001; column: Acquity UPLC BEH C18 1.7 50×2.1 mm; eluent A: water+0.1% by vol. of formic acid (99%), eluent B: acetonitrile; gradient: 0-1.6 min 1-99% B, 1.6-2.0 min 99% B; flow rate 0.8 ml/min; temperature: 60° C.; injection: 2 µl; DAD scan: 210-400 nm; MS ESI+, ESI–, scan range 160-1000 m/z; ELSD.

Method A2: UPLC (MeCN—$NH_3$):

Instrument: Waters Acquity UPLC-MS SQD 3001; column: Acquity UPLC BEH C18 1.7 50×2.1 mm; eluent A: water+0.2% by vol. of ammonia (32%), eluent B: acetonitrile; gradient: 0-1.6 min 1-99% B, 1.6-2.0 min 99% B; flow rate 0.8 ml/min; temperature: 60° C.; injection: 2 µl; DAD scan: 210-400 n; MS ESI+, ESI–, scan range 160-1000 m/z; ELSD.

Method A3: (LC-MS)

Instrument: Agilent 1290 Infinity LC; column: Acquity UPLC BEH C18 1.7 50×2.1 mm; eluent A: water+0.05% by vol. of formic acid, eluent B: acetonitrile+0.05% by vol. of formic acid; gradient: 0-1.7 min 2-90% B, 1.7-2.0 min 90% B; flow rate 1.2 ml/min; temperature: 60° C.; injection: 2 µl; DAD scan: 190-390 nm; MS: Agilent TOF 6230.

Method A4: (LC-MS)

Instrument: Waters Acquity; column: Kinetex (Phenomenex), 50×2 mm; eluent A: water+0.05% by vol. of formic acid, eluent B: acetonitrile+0.05% by vol. of formic acid; gradient: 0-1.9 min 1-99% B, 1.9-2.1 min 99% B; flow rate 1.5 ml/min; temperature: 60° C.; injection: 0.5 µl; DAD scan: 200-400 nm.

In some cases, the compounds of the general formula (I) and the precursors and/or intermediates thereof were purified by the following illustrative preparative HPLC methods:

Method P1: system: Waters Autopurification system: Pump 2545, Sample Manager 2767, CFO, DAD 2996, ELSD 2424, SQD; column: XBridge C18 5 µm 100×30 mm; eluent A: water+0.1% by vol. of formic acid, eluent B: acetonitrile; gradient: 0-8 min 10-100% B, 8-10 min 100% B; flow: 50 ml/min; temperature: room temperature; solution: max. 250 mg/max. 2.5 ml DMSO or DMF; injection: 1×2.5 ml; detection: DAD scan range 210-400 nm; MS ESI+, ESI–, scan range 160-1000 m/z.

Method P2: system: Waters Autopurification system: Pump 254, Sample Manager 2767, CFO, DAD 2996, ELSD 2424, SQD 3100; column: XBridge C18 5 µm 10×30 mm; eluent A: water+0.2% by vol. of ammonia (32%), eluent B: methanol; gradient: 0-8 min 30-70% B; flow: 50 ml/min; temperature: room temperature; detection: DAD scan range 210-400 nm; MS ESI+, ESI–, scan range 160-1000 m/z; ELSD.

Method P3: system: Labomatic, pump: HD-5000, fraction collector: LABOCOL Vario-4000, UV detector: Knauer UVD 2.1S; column: XBridge C18 5 µm 100×30 mm; eluent A: water+0.2% by vol. of ammonia (25%), eluent B: acetonitrile; gradient: 0-1 min 15% B, 1-6.3 min 15-55% B, 6.3-6.4 min 55-100% B, 6.4-7.4 min 100% B; flow: 60 ml/min; temperature: room temperature; solution: max. 250 mg/2 ml DMSO; injection: 2×2 ml; detection: UV 218 nm; Software: SCPA PrepCon5.

Method P4: system: Labomatic, pump: HD-5000, fraction collector: LABOCOL Vario-4000, UV detector: Knauer UVD 2.1S; column: Chromatorex RP C18 10 µm 125×30 mm; eluent A: water+0.1% by vol. of formic acid, eluent B: acetonitrile; gradient: 0-15 min 65-100% B; flow: 60 ml/min; temperature: room temperature; solution: max. 250 mg/2 ml DMSO; injection: 2×2 ml; detection: UV 254 nm; Software: SCPA PrepCon5.

Method P5: system: Sepiatec: Prep SFC100, column: Chiralpak IA 5 µm 250×20 mm; eluent A: carbon dioxide, eluent B: ethanol; gradient: isocratic 20% B; flow: 80 ml/min; temperature: 40° C.; solution: max. 250 mg/2 ml DMSO; injection: 5×0.4 mL; detection: UV 254 nm.

Method P6: system: Agilent: Prep 1200, 2×prep pump, DLA, MWD, Gilson: Liquid Handler 215; column: Chiralcel OJ-H 5 µm 250×20 mm; eluent A: hexane, eluent B: ethanol; gradient: isocratic 30% B; flow: 25 ml/min; temperature: 25° C.; solution: 187 mg/8 ml ethanol/methanol; injection: 8×1.0 ml; detection: UV 280 nm.

Method P7: system: Labomatic, pump: HD-5000, fraction collector: LABOCOL Vario-4000, UV detector: Knauer UVD 2.1S; column: XBridge C18 5 µm 100×30 mm; eluent A: water+0.1% by vol. of formic acid, eluent B: acetonitrile; gradient: 0-3 min: 65% B isocratic, 3-13 min: 65-100% B; flow: 60 ml/min; temperature: room temperature; solution: max. 250 mg/2 ml DMSO; injection: 2×2 ml; detection: UV 254 nm.

Method P8: system: Agilent: Prep 1200, 2×prep pump, DLA, MWD, Gilson: Liquid Handler 215; column: Chiralpak IF 5 µm 250×20 mm; eluent A: ethanol, eluent B: methanol; gradient: isocratic 50% B; flow: 25 ml/min; temperature: 25° C.; solution: 600 mg/7 ml N,N-dimethylformamide; injection: 10×0.7 ml; detection: UV 254 nm.

In some cases, substance mixtures were purified by column chromatography on silica gel.

For preparation of some of the compounds of the general formula (I) and the precursors and/or intermediates thereof, a column chromatography purification ("flash chromatography") was conducted on silica gel using Isolera® devices from Biotage. This was done using cartridges from Biotage, for example the "SNAP Cartridge, KP_SIL" cartridge of different size and "Interchim Puriflash Silica HP 15UM flash column" cartridges from Interchim of different size.

Starting Materials

Intermediate V2-1

Methyl 6-(2-hydroxypropan-2-yl)pyridine-2-carboxylate

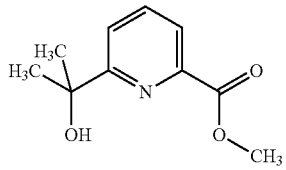

2.00 g (9.26 mmol) of 2-(6-bromopyridin-2-yl)propan-2-ol (CAS 638218-78-7) were dissolved in 20 ml of methanol and 20 ml of DMSO. Subsequently, 250 mg of 1,3-bis(diphenylphosphino)propane, 130 mg of palladium(II) acetate and 3 ml of triethylamine were added. The reaction mixture was purged three times with carbon monoxide at room temperature and stirred under a 13 bar carbon monoxide atmosphere for 30 min. The carbon monoxide atmosphere was removed by applying a vacuum and the mixture was stirred under a 14 bar carbon monoxide atmosphere at 100° C. for 24 h. The autoclave was decompressed, water was added to the reaction mixture, and the reaction mixture was extracted three times with ethyl acetate, washed with saturated aqueous sodium hydrogencarbonate solution and sodium chloride solution, filtered through a hydrophobic filter and concentrated. This gave 1.60 g of a crude product.

UPLC-MS (Method A1): $R_t$=0.76 min (UV detector: TIC), mass found 195.00.

Intermediate V3-1

Potassium 6-(2-hydroxypropan-2-yl)pyridine-2-carboxylate

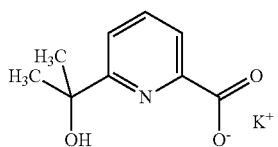

1.60 g of the crude product of Intermediate 0-1 were initially charged in 15 ml of methanol, 0.74 g of potassium hydroxide was added and the mixture was stirred at 50° C. for 16.5 h. After concentration, this gave 2.1 g of a residue which was used without further purification.

UPLC-MS (Method A1): $R_t$=0.47 min (UV detector: TIC), mass found 181.00.

Intermediate 1-1

Methyl 5-nitro-1H-indazole-6-carboxylate

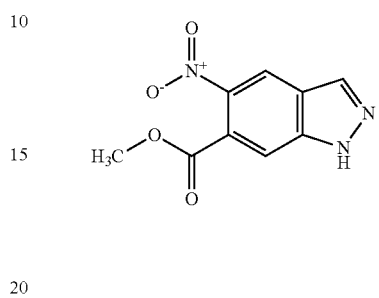

4.60 g (26.1 mmol) of methyl 1H-indazole-6-carboxylate (CAS No: 170487-40-8) were dissolved in 120 ml of sulphuric acid (96%) and cooled to −15° C. in a three-neck flask having a CPG stirrer, dropping funnel and internal thermometer. Over a period of 15 min, the nitrating acid (10 ml of 96% sulphuric acid in 5 ml of 65% nitric acid), which had been prepared and cooled beforehand, was added dropwise to this solution. After the dropwise addition had ended, the mixture was stirred for a further 1 h (internal temperature at −13° C.). The reaction mixture was added to ice, and the precipitate was filtered off with suction, washed with water and dried in a drying cabinet at 50° C. under reduced pressure. 5.49 g of the title compound were obtained.

UPLC-MS (Method A2): $R_t$=0.75 min

MS (ESIpos): m/z=222 (M+H)$^+$ $^1$H NMR (400 MHz, DMSO-d6): δ [ppm]=3.87 (s, 3H), 7.96 (s, 1H), 8.44 (s, 1H), 8.70 (s, 1H), 13.98 (br. s., 1H).

Intermediate 2-1

Methyl 5-amino-1H-indazole-6-carboxylate

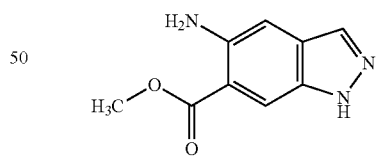

4.40 g (19.8 mmol) of methyl 5-nitro-1H-indazole-6-carboxylate (Intermediate 1-1) were dissolved in 236 ml of methanol and hydrogenated with 1.06 g (0.99 mmol) of palladium on activated carbon under standard hydrogen pressure at 25° C. for 3 h. The reaction mixture was filtered through Celite, the filter was washed with methanol, and the filtrate was concentrated. 3.53 g of the title compound were obtained.

$^1$H NMR (300 MHz, DMSO-d6): δ [ppm]=3.85 (s, 3H) 6.01 (s, 2H) 6.98 (s, 1H) 7.79-7.91 (m, 1H) 7.99 (s, 1H) 12.84 (br. s., 1H).

Intermediate 3-1

Methyl 5-({[6-(trifluoromethyl)pyridin-2-yl]carbonyl}amino)-1H-indazole-6-carboxylate

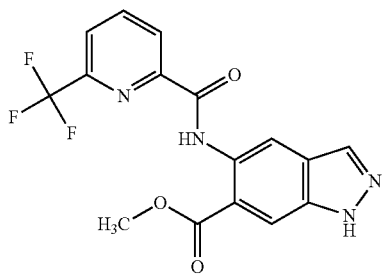 [SMILES: COC(=O)c1cc2[nH]ncc2cc1NC(=O)c1cccc(C(F)(F)F)n1]

4.95 g (25.9 mmol) of 6-(trifluoromethyl)pyridine-2-carboxylic acid were initially charged in 45 ml of THF. 9.07 g (28.2 mmol) of O-(benzotriazol-1-yl)-N,N,N',N'-tetramethyluronium tetrafluoroborate and 4.92 ml (28.2 mmol) of N-ethyl-N-isopropylpropan-2-amine were added and the mixture was stirred at 25° C. for 30 min. Subsequently, 4.50 g (23.5 mmol) of methyl 5-amino-1H-indazole-6-carboxylate (Intermediate 2-1) were added and the mixture was stirred at 25° C. for 24 h. The reaction mixture was filtered with suction through a membrane filter and the solids were washed with THF and with water, and dried in a drying cabinet overnight. 7.60 g of the title compound were obtained.

UPLC-MS (Method A2): $R_t$=1.16 min
MS (ESIpos): m/z=365 (M+H)$^+$
$^1$H NMR (400 MHz, DMSO-d6): δ [ppm]=3.97 (s, 3H), 8.13-8.27 (m, 2H), 8.30 (s, 1H), 8.33-8.45 (m, 1H), 8.45-8.51 (m, 1H), 9.15 (s, 1H), 12.57 (s, 1H), 13.44 (s, 1H).

Intermediate 3-2

Methyl 5-({[6-(difluoromethyl)pyridin-2-yl]carbonyl}amino)-1H-indazole-6-carboxylate

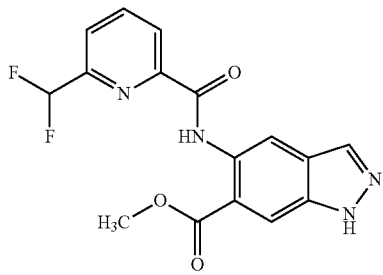 [SMILES: COC(=O)c1cc2[nH]ncc2cc1NC(=O)c1cccc(C(F)F)n1]

2.85 g (23.5 mmol) of 6-(difluoromethyl)pyridine-2-carboxylic acid were initially charged in 30 ml of THF. 6.05 g (18.8 mmol) of O-(benzotriazol-1-yl)-N,N,N',N'-tetramethyluronium tetrafluoroborate and 3.3 ml of N-ethyl-N-isopropylpropan-2-amine were added and the mixture was stirred at room temperature for 10 minutes. Subsequently, 3.00 g (15.7 mmol) of methyl 5-amino-1H-indazole-6-carboxylate were added and the mixture was stirred at room temperature overnight. The reaction mixture was admixed with water, and the precipitate was filtered off with suction and washed repeatedly with water and dichloromethane. This gave 1.53 g (27% of theory) of the title compound. The phases of the filtrate were separated, the organic phase was concentrated, admixed with a little dichloromethane and suspended in an ultrasound bath, and the precipitate was filtered off with suction. This gave a further 1.03 g of the title compound.

1H-NMR (first product fraction, 300 MHz, DMSO-d6): δ [ppm]=3.99 (s, 3H), 7.09 (t, 1H), 8.00 (d, 1H), 8.21-8.40 (m, 4H), 9.14 (s, 1H), 12.53 (s, 1H), 13.44 (s, 1H).

Intermediate 3-3

Methyl 5-({[6-(2-hydroxypropan-2-yl)pyridin-2-yl]carbonyl}amino)-1H-indazole-6-carboxylate

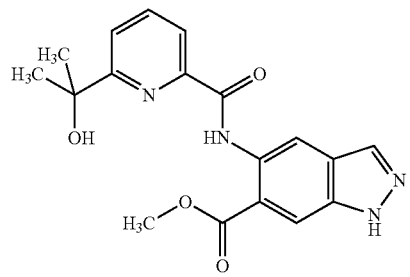 [SMILES: COC(=O)c1cc2[nH]ncc2cc1NC(=O)c1cccc(C(C)(C)O)n1]

2.10 g of potassium 6-(2-hydroxypropan-2-yl)pyridine-2-carboxylate (Intermediate V3-1) were initially charged in 15 ml of THF. 3.69 g (11.5 mmol) of O-(benzotriazol-1-yl)-N,N,N',N'-tetramethyluronium tetrafluoroborate and 2.00 ml of N-ethyl-N-isopropylpropan-2-amine were added and the mixture was stirred at room temperature for 15 min. Subsequently, 1.83 g (9.58 mmol) of methyl 5-amino-1H-indazole-6-carboxylate (Intermediate 2-1) were added and the mixture was stirred at room temperature for 19 h. The mixture was admixed with water and ethyl acetate, the undissolved solids were filtered off, the phases of the filtrate were separated, and the aqueous phase was extracted twice with ethyl acetate, washed with sodium chloride solution, filtered through a hydrophobic filter, concentrated and purified by column chromatography on silica gel (hexane/ethyl acetate). After the solvents had been removed, 1.56 g of the title compound were obtained as a yellow foam.

UPLC-MS (Method A1): $R_t$=1.00 min (UV detector: TIC Smooth), mass found 354.00. 1H-NMR (500 MHz, DMSO-d6): δ [ppm]=1.63 (s, 6H), 3.97 (s, 3H), 5.37 (s, 1H), 7.90-7.95 (m, 1H), 8.03-8.07 (m, 2H), 8.23 (s, 1H), 8.29 (s, 1H), 9.19 (s, 1H), 12.79 (s, 1H), 13.41 (br.s., 1H).

Intermediate 4-1

Methyl 2-(oxetan-3-ylmethyl)-5-({[6-(trifluoromethyl)pyridin-2-yl]carbonyl}amino)-2H-indazole-6-carboxylate

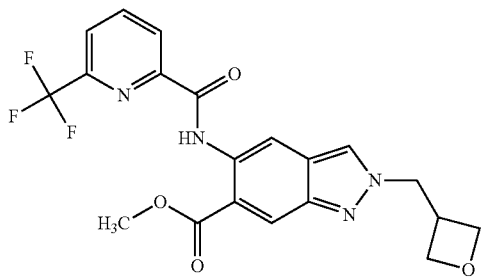 [SMILES: COC(=O)c1cc2nn(CC3COC3)cc2cc1NC(=O)c1cccc(C(F)(F)F)n1]

1.00 g (2.66 mmol) of methyl 5-({[6-(trifluoromethyl)pyridin-2-yl]carbonyl}amino)-1H-indazole-6-carboxylate (Intermediate 3-1) was dissolved in 10 ml of DMF and, after addition of 1.10 g (7.99 mmol) of potassium carbonate and 221 mg (1.33 mmol) of potassium iodide, the mixture was stirred at 25° C. for 30 min. 603 mg (3.99 mmol) of 3-bromomethyloxetane were added, and the mixture was stirred at 25° C. for 24 h. The reaction mixture was partitioned between water and ethyl acetate. The mixture was extracted twice with ethyl acetate, and the combined organic phases were filtered through a hydrophobic filter and concentrated. The residue was purified by column chromatography on silica gel (hexane/ethyl acetate). 260 mg of the title compound were obtained.

UPLC-MS (Method A2): $R_t$=1.24 min
MS (ESIpos): m/z=435 (M+H)$^+$
$^1$H NMR (400 MHz, DMSO-d6): δ [ppm]=3.49-3.64 (m, 1H), 3.95 (s, 3H), 4.49 (t, 2H), 4.68 (dd, 2H), 4.81 (d, 2H), 8.20 (dd, 1H), 8.35-8.41 (m, 1H), 8.43-8.49 (m, 2H), 8.55-8.58 (m, 1H), 9.06 (s, 1H), 12.53 (s, 1H).

Intermediate 4-2

Methyl 2-(2-methoxyethyl)-5-({[6-(trifluoromethyl)pyridin-2-yl]carbonyl}amino)-2H-indazole-6-carboxylate

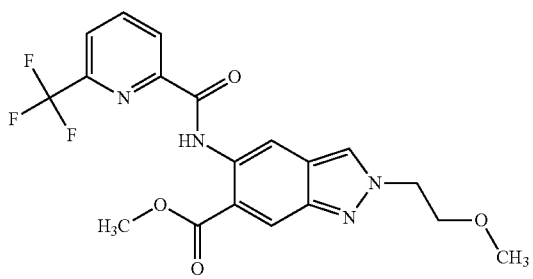 [SMILES: COCCn1cc2cc(NC(=O)c3cccc(C(F)(F)F)n3)c(C(=O)OC)cc2n1]

1.00 g (2.75 mmol) of methyl 5-({[6-(trifluoromethyl)pyridin-2-yl]carbonyl}amino)-1H-indazole-6-carboxylate (Intermediate 3-1) was dissolved in 5 ml of DMF, and 387 µl (4.12 mmol) of 2-bromoethyl methyl ether, 1.14 g (8.23 mmol) of potassium carbonate and 228 mg (1.37 mmol) of potassium iodide were added while stirring. The reaction mixture was stirred at 25° C. for 24 h, diluted with water and extracted twice with ethyl acetate. The combined organic phases were filtered through a hydrophobic filter and concentrated. The residue was purified by column chromatography on silica gel (hexane/ethyl acetate). 12 mg of the title compound were obtained.

UPLC-MS (Method A1): $R_t$=1.24 min
MS (ESIpos): m/z=423 (M+H)$^+$
$^1$H NMR (400 MHz, DMSO-d6): δ [ppm]=3.24 (s, 3H), 3.86 (t, 2H), 3.96 (s, 3H), 4.65 (t, 2H), 8.21 (dd, 1H), 8.35-8.42 (m, 1H), 8.43-8.51 (m, 2H), 8.52 (d, 1H), 9.06 (s, 1H), 12.53 (s, 1H).

Intermediate 4-3

Methyl 2-(3-methoxypropyl)-5-({[6-(trifluoromethyl)pyridin-2-yl]carbonyl}amino)-2H-indazole-6-carboxylate

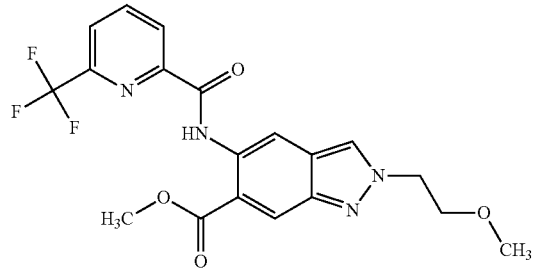 [SMILES: COCCn1cc2cc(NC(=O)c3cccc(C(F)(F)F)n3)c(C(=O)OC)cc2n1]

1.00 g (2.75 mmol) of methyl 5-({[6-(trifluoromethyl)pyridin-2-yl]carbonyl}amino)-1H-indazole-6-carboxylate (Intermediate 3-1) was dissolved in 5 ml of DMF, and 460 µl (4.12 mmol) of 1-bromo-3-methoxypropane, 1.14 g (8.23 mmol) of potassium carbonate and 228 mg (1.37 mmol) of potassium iodide were added while stirring. The reaction mixture was stirred at 25° C. for 72 h, diluted with water and extracted twice with ethyl acetate. The combined organic phases were filtered through a hydrophobic filter and concentrated. The residue was purified by column chromatography on silica gel (hexane/ethyl acetate). 28 mg of the title compound were obtained.

UPLC-MS (Method A1): $R_t$=1.29 min
MS (ESIpos): m/z=437 (M+H)$^+$
$^1$H NMR (400 MHz, DMSO-d6): δ [ppm]=2.17 (quin, 2H), 3.24 (s, 3H), 3.33-3.36 (m, 2H), 3.96 (s, 3H), 4.53 (t, 2H), 8.21 (dd, 1H), 8.35-8.42 (m, 1H), 8.45-8.49 (m, 2H), 8.54 (d, 1H), 9.06 (s, 1H), 12.54 (s, 1H).

Intermediate 4-4

Methyl 2-(3-hydroxy-3-methylbutyl)-5-({[6-(trifluoromethyl)pyridin-2-yl]carbonyl}amino)-2H-indazole-6-carboxylate Preparation Method 1

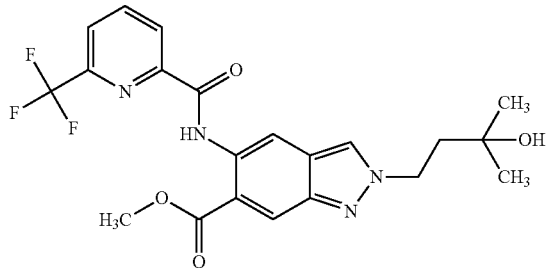 [SMILES: COC(=O)c1cc2nn(CCC(C)(C)O)cc2cc1NC(=O)c1cccc(C(F)(F)F)n1]

930 mg (2.55 mmol) of methyl 5-({[6-(trifluoromethyl)pyridin-2-yl]carbonyl}amino)-1H-indazole-6-carboxylate (Intermediate 3-1), 1.06 g of potassium carbonate and 212 mg of potassium iodide were initially charged in 9 ml of DMF and the mixture was stirred for 15 min. Then 0.62 ml of 4-bromo-2-methylbutan-2-ol was added and the mixture was stirred at 60° C. for 16 h. The mixture was admixed with water and extracted twice with ethyl acetate, and the extract was washed three times with saturated sodium chloride solution, filtered and concentrated. Column chromatography purification on silica gel (hexane/ethyl acetate) gave 424 mg of the title compound.

UPLC-MS (Method A2): $R_t$=1.21 min (UV detector: TIC), mass found 450.00.

$^1$H-NMR (400 MHz, DMSO-$d_6$): δ [ppm]=1.16 (s, 6H) 2.02-2.11 (m, 2H) 3.96 (s, 3H) 4.51-4.60 (m, 3H) 8.20 (dd, J=7.83, 1.01 Hz, 1H) 8.39 (s, 1H) 8.45 (s, 2H) 8.55 (d, J=0.76 Hz, 1H) 9.05 (s, 1H) 12.52 (s, 1H)

Preparation Method 2

1.95 g (7.03 mmol) of methyl 5-amino-2-(3-hydroxy-3-methylbutyl)-2H-indazole-6-carboxylate (Intermediate 7-1) were initially charged in 30 ml of THF. 1.48 g (7.73 mmol) of 6-(trifluoromethyl)pyridine-2-carboxylic acid, 2.71 g (8.44 mmol) of O-(benzotriazol-1-yl)-N,N,N',N'-tetramethyluronium tetrafluoroborate and 1.47 ml (8.44 mmol) of N-ethyl-N-isopropylpropan-2-amine were added and the mixture was stirred at 25° C. for 20.5 h. Water was added, the mixture was extracted three times with ethyl acetate and the extracts were washed with sodium chloride solution, filtered through a hydrophobic filter and concentrated. The residue was separated by column chromatography on silica gel (hexane/ethyl acetate gradient). 2.79 g of the title compound were obtained.

UPLC-MS (Method A1): $R_t$=1.23 min (UV detector: TIC), mass found 450.00.

Intermediate 4-5

Methyl 2-(2-{[tert-butyl(dimethyl)silyl]oxy}ethyl)-5-({[6-(trifluoromethyl)pyridin-2-yl]carbonyl}amino)-2H-indazole-6-carboxylate

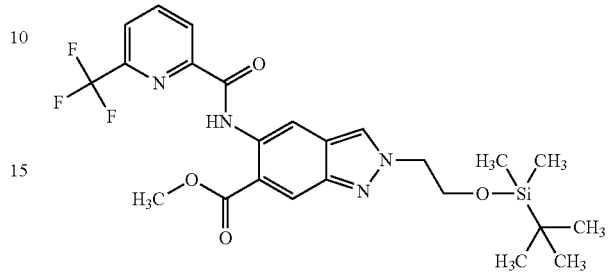

1.00 g (2.66 mmol, 97%) of methyl 5-({[6-(trifluoromethyl)pyridin-2-yl]carbonyl}amino)-1H-indazole-6-carboxylate (Intermediate 3-1) was initially charged in 50 ml of DMF, 1.10 g (7.99 mmol) of potassium carbonate and 221 mg (1.33 mmol) of potassium iodide were added while stirring, and the mixture was stirred at 25° C. for 30 min. Subsequently, 857 µl (3.99 mmol) of (2-bromoethoxy)(tert-butyl)dimethylsilane were added and the mixture was stirred at 25° C. for 24 h. The reaction mixture was diluted with water and extracted with ethyl acetate. The combined organic phases were filtered through a hydrophobic filter and concentrated. The residue was purified by column chromatography on silica gel (hexane/ethyl acetate). 400 mg of the title compound were obtained.

UPLC-MS (Method A1): $R_t$=1.58 min

MS (ESIpos): m/z=523 (M+H)$^+$ $^1$H NMR (300 MHz, DMSO-d6): δ [ppm]=−0.18−−0.13 (m, 6H), 0.74 (s, 9H), 3.96 (s, 3H), 4.08 (t, 2H), 4.57 (t, 2H), 8.15-8.25 (m, 1H), 8.32-8.43 (m, 1H), 8.43-8.52 (m, 3H), 9.07 (s, 1H), 12.53 (s, 1H).

Intermediate 4-6

Methyl 2-(3-{[tert-butyl(dimethyl)silyl]oxy}propyl)-5-({[6-(trifluoromethyl)pyridin-2-yl]carbonyl}amino)-2H-indazole-6-carboxylate

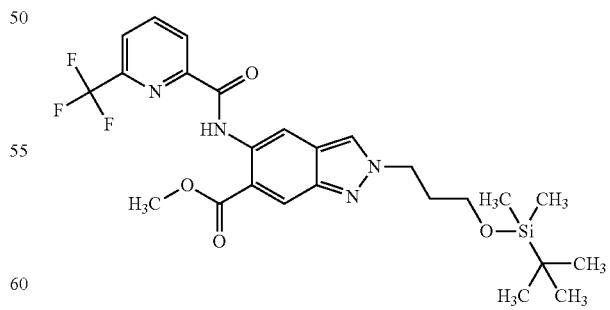

Analogously to Intermediate 4-5, 1.00 g (2.75 mmol) of methyl 5-({[6-(trifluoromethyl)pyridin-2-yl]carbonyl}amino)-1H-indazole-6-carboxylate (Intermediate 3-1) was dissolved in 10 ml of DMF, 1.14 g (8.24 mmol) of potassium carbonate and 228 mg (1.37 mmol) of potassium iodide were added while stirring, and the mixture was stirred at 25° C. for 30 min. Subsequently, 1.04 g (4.12 mmol) of (3-bromopropoxy)(tert-butyl)dimethylsilane were added and the mixture was stirred at 25° C. for 24 h. The reaction mixture was filtered and the filtercake was washed with ethyl acetate. The reaction mixture was partitioned between water and ethyl acetate and the aqueous phase was extracted twice with ethyl acetate. The combined organic phases were filtered through a hydrophobic filter and concentrated. Purification of the residue by preparative HPLC gave 428 mg of the title compound.

UPLC-MS (Method A1): $R_t$=1.63 min

MS (ESIpos): m/z=537 (M+H)$^+$ $^1$H NMR (400 MHz, DMSO-d6): δ [ppm]=−0.02-0.06 (m, 6H), 0.87 (s, 9H), 2.14 (quin, 2H), 3.62 (t, 2H), 3.96 (s, 3H), 4.54 (t, 2H), 8.20 (d, 1H), 8.35-8.42 (m, 1H), 8.43-8.48 (m, 3H), 8.49-8.53 (m, 1H), 9.06 (s, 1H).

Intermediate 4-7

Methyl 5-({[6-(2-hydroxypropan-2-yl)pyridin-2-yl]carbonyl}amino)-2-(4,4,4-trifluorobutyl)-2H-indazole-6-carboxylate

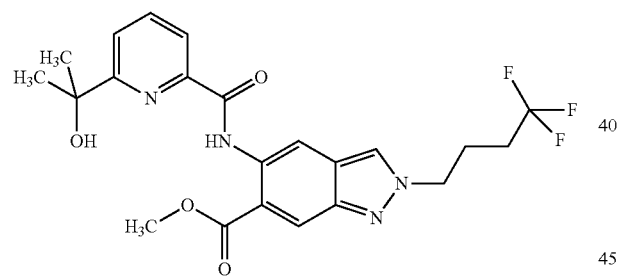

300 mg (0.80 mmol) of methyl 5-({[6-(2-hydroxypropan-2-yl)pyridin-2-yl]carbonyl}amino)-1H-indazole-6-carboxylate (Intermediate 3-3) were initially charged in 4.5 ml of DMF. 287 mg (1.21 mmol) of 1,1,1-trifluoro-4-iodobutane and 333 mg of potassium carbonate were added and the mixture was stirred at 100° C. for 23 h. Water was added, and the mixture was extracted three times with ethyl acetate. The mixture was concentrated and the product was purified by preparative HPLC. This gave 72 mg of the title compound.

UPLC-MS (Method A1): $R_t$=1.26 min (UV detector: TIC), mass found 464.17.

Intermediate 4-8

Methyl 5-{[(5-fluoro-6-methylpyridin-2-yl)carbonyl]amino}-2-(3-hydroxy-3-methylbutyl)-2H-indazole-6-carboxylate

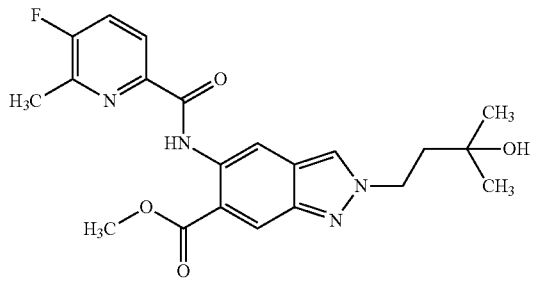 [SMILES: COC(=O)c1cc2nn(CCC(C)(C)O)cc2cc1NC(=O)c1ccc(F)c(C)n1]

195 mg (0.46 mmol) of methyl 5-amino-2-(3-hydroxy-3-methylbutyl)-2H-indazole-6-carboxylate (Intermediate 7-1) were reacted with 78 mg (0.50 mmol) of 5-fluoro-6-methylpyridine-2-carboxylic acid analogous to Intermediate 4-4 (Preparation Method 2) within 19.5 h. 228 mg of a crude product were obtained after analogous aqueous workup.

UPLC-MS (Method A1): $R_t$=1.20 min (UV detector: TIC), mass found 414.00.

Intermediate 4-9

Methyl 2-(3-hydroxy-3-methylbutyl)-5-{[(6-methylpyridin-2-yl)carbonyl]amino}-2H-indazole-6-carboxylate

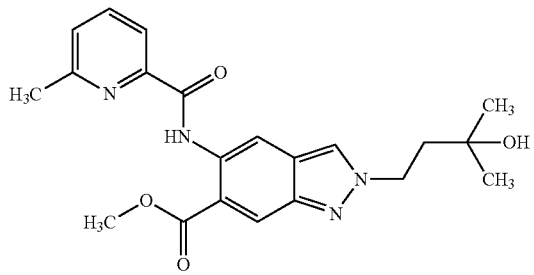 [SMILES: COC(=O)c1cc2nn(CCC(C)(C)O)cc2cc1NC(=O)c1cccc(C)n1]

195 mg (0.45 mmol) of methyl 5-amino-2-(3-hydroxy-3-methylbutyl)-2H-indazole-6-carboxylate (Intermediate 7-1) were reacted with 70 mg (0.50 mmol) of 6-methylpyridine-2-carboxylic acid analogously to preparation of Intermediate 4-4 (Preparation Method 2) within 19.5 h. 278 mg of the title compound as crude product were obtained after analogous aqueous workup.

UPLC-MS (Method A1): $R_t$=1.14 min (UV detector: TIC), mass found 396.00.

Intermediate 4-10

Methyl 2-[3-(2,2,2-trifluoroethoxy)propyl]-5-({[6-(trifluoromethyl)pyridin-2-yl]carbonyl}amino)-2H-indazole-6-carboxylate

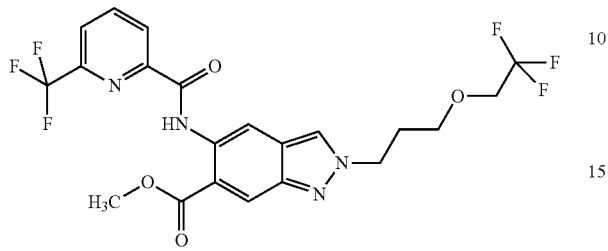

A mixture of 250 mg (0.58 mmol) of methyl 5-({[6-(trifluoromethyl)pyridin-2-yl]carbonyl}amino)-1H-indazole-6-carboxylate (Intermediate 3-1), 193 mg (0.88 mmol) of 3-bromopropyl 2,2,2-trifluoroethyl ether, 242 mg of potassium carbonate and 145 mg of potassium iodide in 3 ml of DMF was stirred at 100° C. for 20 h. Water was added, the mixture was extracted with ethyl acetate and the extract was washed with sodium chloride solution and concentrated. Purification by preparative HPLC gave 52 mg of the title compound.

UPLC-MS (Method A1): $R_t$=1.39 min (UV detector: TIC), mass found 504.12.

Intermediate 4-11

Methyl 5-({[6-(difluoromethyl)pyridin-2-yl]carbonyl}amino)-2-(3-hydroxy-3-methylbutyl)-2H-indazole-6-carboxylate

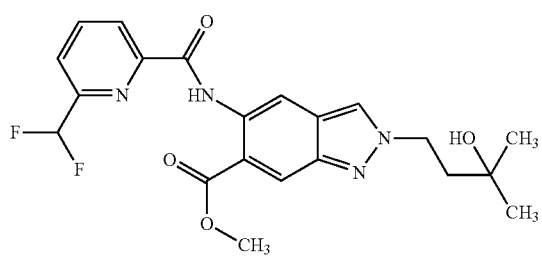 [SMILES: COC(=O)c1cc2nn(CCC(C)(C)O)cc2cc1NC(=O)c1cccc(C(F)F)n1]

2.00 g of methyl 5-amino-2-(3-hydroxy-3-methylbutyl)-2H-indazole-6-carboxylate (Intermediate 7-1) were initially charged in 40 ml of THF. 1.50 g of 6-(difluoromethyl)pyridine-2-carboxylic acid, 2.78 g of O-(benzotriazol-1-yl)-N,N,N',N'-tetramethyluronium tetrafluoroborate (TBTU, CAS Number 125700-67-6) and 1.5 ml of N-ethyl-N-isopropylpropan-2-amine were added and the mixture was stirred at RT for 24 h. Water was added, the mixture was extracted three times with ethyl acetate, and the combined organic phases were washed with sodium chloride solution and filtered through a hydrophobic filter. The mixture was concentrated and the residue was purified by column chromatography on silica gel (hexane/ethyl acetate). This gave 3.05 g of the title compound as a yellow solid.

UPLC-MS (Method A1): Rt=1.15 min (UV detector TIC), mass found 432.00.

$^1$H-NMR (400 MHz, DMSO-$d_6$): δ [ppm]=1.17 (s, 6H), 2.04-2.11 (m, 2H), 3.99 (s, 3H), 4.52-4.60 (m, 3H), 7.10 (t, 1H), 8.00 (dd, 1H), 8.28-8.38 (m, 2H), 8.44-8.47 (m, 1H), 8.56 (d, 1H), 9.05 (s, 1H), 12.49 (s, 1H).

Intermediate 5-1

N-[6-(2-Hydroxypropan-2-yl)-1H-indazol-5-yl]-6-(trifluoromethyl)pyridine-2-carboxamide

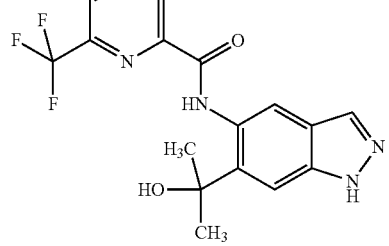

To a solution, cooled in an ice-water cooling bath, of 1.50 g (4.12 mmol) of methyl 5-({[6-(trifluoromethyl)pyridin-2-yl]carbonyl}amino)-1H-indazole-6-carboxylate (Intermediate 3-1) in 20 ml of THF were cautiously added 6.9 ml (5 equivalents) of a 3M methylmagnesium bromide solution in diethyl ether. The mixture was stirred while cooling with an ice bath for 1 h and at room temperature for 19.5 h. Another 2 equivalents of methylmagnesium bromide solution were added and the mixture was stirred at room temperature for a further 24 h. Saturated aqueous ammonium chloride solution was added and the mixture was stirred and extracted three times with ethyl acetate. The combined organic phases were washed with sodium chloride solution, filtered through a hydrophobic filter and concentrated. The residue was purified by column chromatography on silica gel (hexane/ethyl acetate). 763 mg of the title compound were obtained.

$^1$H-NMR (400 MHz, DMSO-$d_6$): δ [ppm]=1.63 (s, 6H), 5.99 (s, 1H), 7.49 (s, 1H), 8.06 (s, 1H), 8.14-8.19 (m, 1H), 8.37 (t, 1H), 8.46 (d, 1H), 8.78 (s, 1H), 12.32 (s, 1H), 12.97 (s, 1H).

Intermediate 5-2

6-(Difluoromethyl)-N-[6-(2-hydroxypropan-2-yl)-1H-indazol-5-yl]pyridine-2-carboxamide

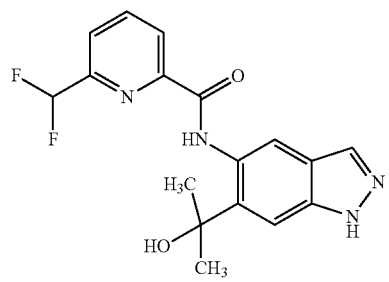 [SMILES: CC(C)(O)c1cc2[nH]ncc2cc1NC(=O)c1cccc(C(F)F)n1]

Analogously to the preparation of Intermediate 5-1, 2.40 g (6.93 mmol) of methyl 5-({[6-(difluoromethyl)pyridin-2-yl]carbonyl}amino)-1H-indazole-6-carboxylate (Intermediate 3-2) in 10 ml of THF were reacted with three portions of 3M methylmagnesium bromide solution in diethyl ether (6.9 ml, then stirring at room temperature for 45 min; 11.6 ml, then stirring at room temperature for 2 h; 6.9 ml, then stirring at room temperature for 2 h). After the workup as for Intermediate 5-1, 2.39 g of a crude product were obtained, which were used further without further purification.

Intermediate 6-1

Methyl 2-(3-hydroxy-3-methylbutyl)-5-nitro-2H-indazole-6-carboxylate

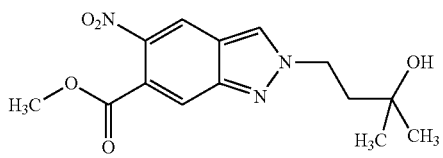 [SMILES: COC(=O)c1cc2nn(CCC(C)(C)O)cc2cc1[N+](=O)[O-]]

5.00 g (22.6 mmol) of methyl 5-nitro-1H-indazole-6-carboxylate (Intermediate 1-1) were initially charged in 40 ml of DMF. 5.65 g (33.9 mmol) of 4-bromo-2-methylbutan-2-ol, 9.37 g (67.8 mmol) of potassium carbonate and 5.63 g (33.9 mmol) of potassium iodide were added and the mixture was stirred at 100° C. for 20 h. Water was added, the mixture was extracted three times with ethyl acetate and the extracts were washed with sodium chloride solution, filtered through a hydrophobic filter and concentrated. The residue was purified by column chromatography on silica gel (hexane/ethyl acetate). The solids obtained were extracted by stirring with diethyl ether, filtered off with suction, washed with diethyl ether and dried. 2.49 g of the title compound were obtained.

UPLC-MS (Method A1): $R_t$=0.93 min (UV detector: TIC), mass found 307.00.

$^1$H-NMR (400 MHz, DMSO-d$_6$): δ [ppm]=1.15 (s, 6H), 2.02-2.11 (m, 2H), 3.84 (s, 3H), 4.54 (s, 1H), 4.58-4.65 (m, 2H), 8.05 (s, 1H), 8.69 (s, 1H), 8.86 (s, 1H).

Intermediate 7-1

Methyl 5-amino-2-(3-hydroxy-3-methylbutyl)-2H-indazole-6-carboxylate

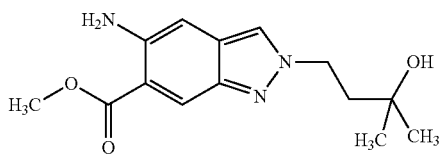 [SMILES: COC(=O)c1cc2nn(CCC(C)(C)O)cc2cc1N]

4.53 g of iron and 217 mg of ammonium chloride were added to 2.49 g (8.10 mmol) of methyl 2-(3-hydroxy-3-methylbutyl)-5-nitro-2H-indazole-6-carboxylate (Intermediate 6-1) in 30 ml of ethanol and 10 ml of water, and the mixture was stirred at 90° C. for 21.5 h. The mixture was filtered through Celite and washed through with ethanol three times, and the filtrate was concentrated and the residue was admixed with water. Extraction was effected three times with ethyl acetate (to improve the phase separation, sodium chloride solution was added). The combined organic phases were washed with sodium chloride solution, filtered through a hydrophobic filter and concentrated. This gave 1.95 g (85% of theory) of the title compound.

UPLC-MS (Method A1): $R_t$=0.67 min (UV detector: TIC), mass found 277.00.

$^1$H-NMR (400 MHz, DMSO-d$_6$): δ [ppm]=1.14 (s, 6H), 1.96-2.08 (m, 2H), 3.85 (s, 3H), 4.39-4.51 (m, 3H), 5.81 (s, 2H), 6.80 (s, 1H), 8.05 (s, 1H), 8.18 (s, 1H).

WORKING EXAMPLES

Example 1

N-[6-(2-Hydroxypropan-2-yl)-2-(2-methoxyethyl)-2H-indazol-5-yl]-6-(trifluoromethyl)pyridine-2-carboxamide

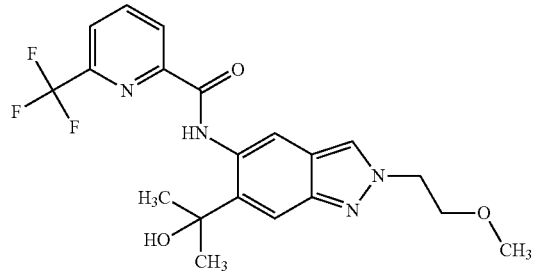 [SMILES: COCCn1cc2cc(NC(=O)c3cccc(C(F)(F)F)n3)c(C(C)(C)O)cc2n1]

75 mg (0.18 mmol) of methyl 2-(2-methoxyethyl)-5-({[6-(trifluoromethyl)pyridin-2-yl]carbonyl}amino)-2H-indazole-6-carboxylate (Intermediate 4-2) were dissolved in 500 µl of THF and admixed with 887 µl (0.89 mmol) of a 1 M methylmagnesium bromide solution in THF. The reaction mixture was stirred at 25° C. for 60 min. Subsequently, 1 ml of a saturated aqueous ammonium chloride solution was added cautiously and the mixture was filtered. The aqueous phase was extracted twice with ethyl acetate, and the organic phases were combined, filtered through a hydrophobic filter and concentrated. The residue was dissolved in 3 ml of DMSO and purified by preparative HPLC. The product-containing fractions were freeze-dried. 20 mg of the title compound were obtained.

UPLC-MS (Method A1): $R_t$=1.08 min
MS (ESIpos): m/z=423 (M+H)$^+$
$^1$H NMR (300 MHz, DMSO-d6): δ [ppm]=1.62 (s, 6H), 3.22 (s, 3H), 3.82 (t, 2H), 4.55 (t, 2H), 5.96 (s, 1H), 7.57 (s, 1H), 8.16 (d1H), 8.29-8.42 (m, 2H), 8.42-8.50 (m, 1H), 8.71 (s, 1H), 12.36 (s, 1H)

Example 2

N-[6-(Hydroxymethyl)-2-(2-methoxyethyl)-2H-indazol-5-yl]-6-(trifluoromethyl)pyridine-2-carboxamide

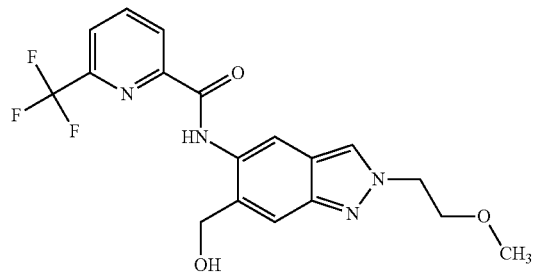 [SMILES: COCCn1cc2cc(NC(=O)c3cccc(C(F)(F)F)n3)c(CO)cc2n1]

13 mg (0.36 mmol) of lithium aluminium hydride were suspended in 1 ml of THF and the mixture was cooled to 0° C. 75 mg (0.17 mmol) of methyl 2-(2-methoxyethyl)-5-({[6-(trifluoromethyl)pyridin-2-yl]carbonyl}amino)-2H-indazole-6-carboxylate (Intermediate 4-2) dissolved in 500 μl of THF were added dropwise and the mixture was stirred at 25° C. for 60 min. The mixture was diluted with water and extracted twice with ethyl acetate, and the combined organic phases were washed with sodium chloride solution, filtered through a hydrophobic filter, concentrated and dried under reduced pressure. This gave 13 mg of the title compound.

UPLC-MS (Method A2): R$_t$=0.99 min

MS (ESIpos): m/z=394 (M+H)$^+$ $^1$H NMR (400 MHz, DMSO-d6): δ [ppm]=3.23 (s, 3H), 3.83 (t, 2H), 4.56 (t, 2H), 4.69 (d, 2H), 5.77 (t, 1H), 7.57 (s, 1H), 8.19 (d, 1H), 8.33-8.41 (m, 2H), 8.43-8.47 (m, 1H), 8.51 (s, 1H), 11.20 (s, 1H)

Example 3

N-[6-(2-Hydroxypropan-2-yl)-2-(3-methoxypropyl)-2H-indazol-5-yl]-6-(trifluoromethyl)pyridine-2-carboxamide

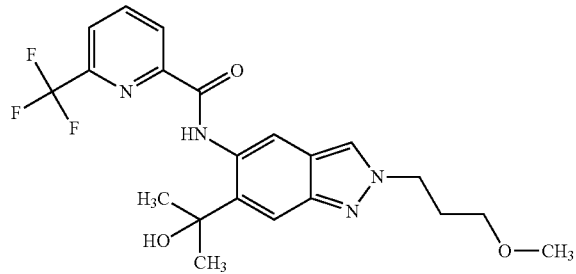 [SMILES: COCCCn1cc2cc(NC(=O)c3cccc(C(F)(F)F)n3)c(C(C)(C)O)cc2n1]

75 mg (0.17 mmol) of methyl 2-(3-methoxypropyl)-5-({[6-(trifluoromethyl)pyridin-2-yl]carbonyl}amino)-2H-indazole-6-carboxylate (Intermediate 4-3) were dissolved in 500 μl of THF and admixed with 859 μl (0.86 mmol) of a 1 M methylmagnesium bromide solution in THF. The reaction mixture was stirred at 25° C. for 60 min. Subsequently, 1 ml of a saturated ammonium chloride solution was added cautiously and the mixture was filtered. The aqueous phase was extracted twice with ethyl acetate, and the organic phases were combined, filtered through a hydrophobic filter and concentrated. The residue was dissolved in 3 ml of DMSO and purified by preparative HPLC. The product-containing fractions were freeze-dried. 25 mg of the title compound were obtained.

UPLC-MS (Method A1): R$_t$=1.13 min

MS (ESIpos): m/z=437 (M+H)$^+$ $^1$H NMR (400 MHz, DMSO-d6): δ [ppm]=1.62 (s, 6H), 2.14 (quin, 2H), 3.23 (s, 3H), 3.26-3.32 (m, 2H), 4.44 (t, 2H), 5.95 (s, 1H), 7.58 (s, 1H), 8.16 (d, 1H), 8.31-8.40 (m, 2H), 8.43-8.48 (m, 1H), 8.72 (s, 1H), 12.36 (s, 1H).

Example 4

N-[6-(Hydroxymethyl)-2-(3-methoxypropyl)-2H-indazol-5-yl]-6-(trifluoromethyl)pyridine-2-carboxamide

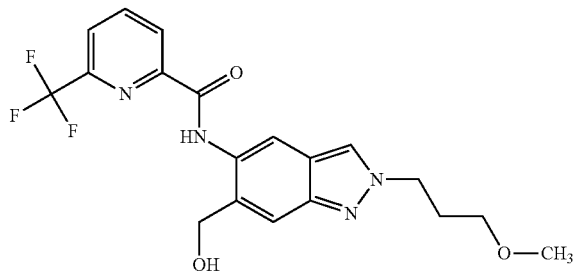 [SMILES: COCCCn1cc2cc(NC(=O)c3cccc(C(F)(F)F)n3)c(CO)cc2n1]

13 mg of lithium aluminium hydride were suspended in THF and the mixture was cooled to 0° C. 75 mg (0.17 mmol) of methyl 2-(3-methoxypropyl)-5-({[6-(trifluoromethyl)pyridin-2-yl]carbonyl}amino)-2H-indazole-6-carboxylate (Intermediate 4-3) in THF were added dropwise and the mixture was allowed to come to room temperature within 30 min. The mixture was diluted with water and filtered, the residue was washed with ethyl acetate and the filtrate was extracted with ethyl acetate. The combined ethyl acetate phases were washed with sodium chloride solution, filtered through a hydrophobic filter and concentrated. The residue was purified by preparative HPLC.

$^1$H NMR (300 MHz, DMSO-d$_6$): δ [ppm]=2.14 (quin, 2H), 3.23 (s, 3H), 3.29 (t, 2H), 4.45 (t, 2H), 4.68 (d, 2H), 5.77 (t, 1H), 7.58 (s, 1H), 8.18 (d, 1H), 8.32-8.48 (m, 3H), 8.51 (s, 1H), 11.21 (s, 1H).

Example 5

N-[2-(2-Hydroxyethyl)-6-(2-hydroxypropan-2-yl)-2H-indazol-5-yl]-6-(trifluoromethyl)pyridine-2-carboxamide Stage A Preparation of N-[2-(2-{[tert-butyl(dimethyl)silyl]oxy}ethyl)-6-(2-hydroxypropan-2-yl)-2H-indazol-5-yl]-6-(trifluoromethyl)pyridine-2-carboxamide

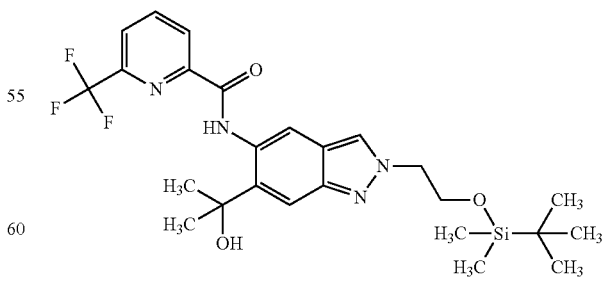

100 mg (0.19 mmol) of methyl 2-(2-{[tert-butyl(dimethyl)silyl]oxy}ethyl)-5-({[6-(trifluoromethyl)pyridin-2-yl]carbonyl}amino)-2H-indazole-6-carboxylate (Intermediate 4-5) were dissolved in 1 ml of THF and admixed with 669

μl (0.67 mmol) of a 1 M methylmagnesium bromide solution in THF. The reaction mixture was stirred at 25° C. for 60 min. Another 287 μl (0.29 mmol) of a 1 M methylmagnesium bromide solution in THF were added and the mixture was stirred at 25° C. for 3 h. Subsequently, 20 ml of a saturated ammonium chloride solution were added cautiously and the mixture was filtered. The aqueous phase was extracted twice with ethyl acetate, and the organic phases were combined, dried over magnesium sulphate, filtered, concentrated and dried under reduced pressure. This gave 50 mg of N-[2-(2-{[tert-butyl(dimethyl)silyl]oxy}ethyl)-6-(2-hydroxypropan-2-yl)-2H-indazol-5-yl]-6-(trifluoromethyl)pyridine-2-carboxamide.

UPLC-MS (Method A2): $R_t$=1.51 min

MS (ESIpos): m/z=523 (M+H)$^+$ $^1$H NMR (300 MHz, DMSO-d6): δ [ppm]=−0.17-−0.09 (m, 6H), 0.78 (s, 9H), 1.62 (s, 6H), 4.04 (t, 2H), 4.47 (t, 2H), 5.98 (s, 1H), 7.57 (s, 1H), 8.16 (d, 1H), 8.29 (s, 1H), 8.37 (t, 1H), 8.45 (d, 1H), 8.73 (s, 1H), 12.38 (s, 1H).

Stage B

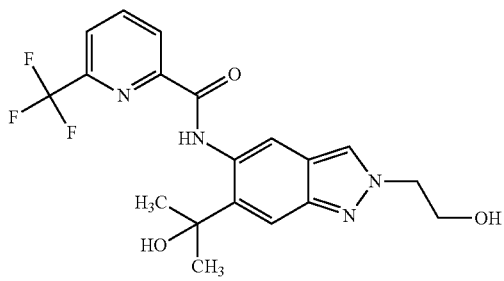 [SMILES: CC(C)(O)c1cc2nn(CCO)cc2cc1NC(=O)c1cccc(C(F)(F)F)n1]

50 mg (96 μmol) of N-[2-(2-{[tert-butyl(dimethyl)silyl]oxy}ethyl)-6-(hydroxymethyl)-2H-indazol-5-yl]-6-(trifluoromethyl)pyridine-2-carboxamide were dissolved in 1.0 ml of THF and admixed with 144 μl (0.14 mmol) of a 1 M solution of tetrabutylammonium fluoride in THF. The reaction mixture was stirred at room temperature for 1 h. The mixture was diluted with water and extracted twice with ethyl acetate, and the combined organic phases were washed with saturated sodium chloride solution, filtered through a hydrophobic filter and concentrated. This gave 36 mg of N-[2-(2-hydroxyethyl)-6-(2-hydroxypropan-2-yl)-2H-indazol-5-yl]-6-(trifluoromethyl)pyridine-2-carboxamide (Example 5).

$^1$H-NMR (400 MHz, DMSO-d$_6$): d [ppm]=1.62 (s, 6H), 3.86 (q, 2H), 4.43 (t, 2H), 4.95 (t, 1H), 5.94 (s, 1H), 7.57 (s, 1H), 8.16 (dd, 1H), 8.30 (s, 1H), 8.37 (t, 1H), 8.45 (d, 1H), 8.72 (s, 1H), 12.36 (s, 1H).

UPLC-MS (Method A2): $R_t$=0.97 min (UV detector: TIC), mass found 408.00.

Example 6

N-[6-(2-Hydroxypropan-2-yl)-2-(3-hydroxypropyl)-2H-indazol-5-yl]-6-(trifluoromethyl)pyridine-2-carboxamide Stage A Preparation of N-[2-(3-{[tert-butyl(dimethyl)silyl]oxy}propyl)-6-(2-hydroxypropan-2-yl)-2H-indazol-5-yl]-6-(trifluoromethyl)pyridine-2-carboxamide

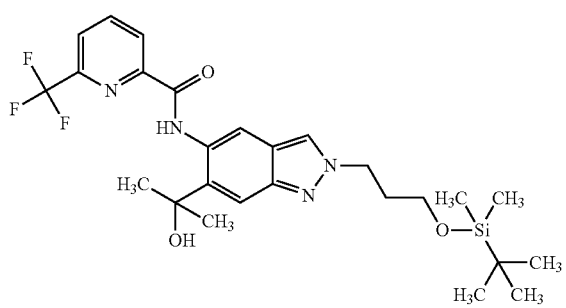 [SMILES: CC(C)(O)c1cc2nn(CCCO[Si](C)(C)C(C)(C)C)cc2cc1NC(=O)c1cccc(C(F)(F)F)n1]

50 mg (0.09 mmol) of methyl 2-(3-{[tert-butyl(dimethyl)silyl]oxy}propyl)-5-({[6-(trifluoromethyl)pyridin-2-yl]carbonyl}amino)-2H-indazole-6-carboxylate (Intermediate 4-6) were dissolved in 500 μl of THF and admixed with 326 μl (0.33 mmol) of a 1 M methylmagnesium bromide solution in THF. The reaction mixture was stirred at 25° C. for 60 min. Subsequently, 20 ml of a saturated ammonium chloride solution were added cautiously and the mixture was extracted twice with ethyl acetate. The combined organic phases were filtered through a hydrophobic filter, concentrated and dried under reduced pressure. The residue was purified by preparative HPLC. 40 mg of N-[2-(3-{[tert-butyl(dimethyl)silyl]oxy}propyl)-6-(2-hydroxypropan-2-yl)-2H-indazol-5-yl]-6-(trifluoromethyl)pyridine-2-carboxamide were obtained.

UPLC-MS (Method A1): $R_t$=1.58 min

MS (ESIpos): m/z=537 (M+H)$^+$ $^1$H NMR (300 MHz, DMSO-d6): δ [ppm]=0.02-0.05 (m, 6H), 0.84-0.91 (m, 9H), 1.62 (s, 6H), 2.02-2.18 (m, 2H), 3.55-3.62 (m, 2H), 4.45 (t, 2H), 5.96 (s, 1H), 7.57 (s, 1H), 8.16 (d, 1H), 8.31 (s, 1H), 8.33-8.42 (m, 1H), 8.45 (d, 1H), 8.72 (s, 1H), 12.37 (s, 1H).

Stage B

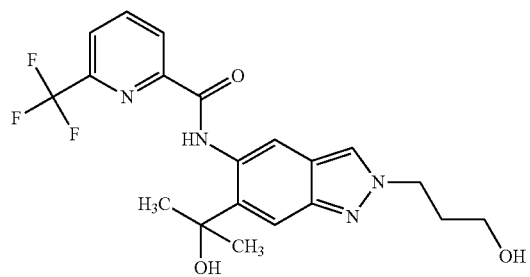 [SMILES: CC(C)(O)c1cc2nn(CCCO)cc2cc1NC(=O)c1cccc(C(F)(F)F)n1]

37 mg (0.07 mmol) of N-[2-(3-{[tert-butyl(dimethyl)silyl]oxy}propyl)-6-(2-hydroxypropan-2-yl)-2H-indazol-5-yl]-6-(trifluoromethyl)pyridine-2-carboxamide were dissolved in 500 μl of THF and admixed with 207 μl (0.21 mmol) of a 1 M solution of tetrabutylammonium fluoride in THF. The reaction mixture was stirred at 25° C. for 2 h. The mixture was diluted with water and extracted twice with ethyl acetate, and the combined organic phases were washed with saturated sodium chloride solution, filtered and concentrated. After purification by preparative HPLC, 10 mg of N-[6-(2-hydroxypropan-2-yl)-2-(3-hydroxypropyl)-2H-indazol-5-yl]-6-(trifluoromethyl)pyridine-2-carboxamide (Example 6, contained secondary component) were obtained.

UPLC-MS (Method A2): $R_t$=1.00 min
MS (ESIpos): m/z=423 (M+H)$^+$
$^1$H NMR selected signals (400 MHz, DMSO-d6): δ [ppm]=1.61 (s), 2.00-2.12 (m), 3.38 (t, 2H), 4.44 (t, 2H), 4.62 (br. s., 1H), 5.93 (br. s., 1H), 7.55 (s, 1H), 8.13 (d, 1H), 8.27-8.38 (m, 2H), 8.43 (d, 1H), 8.71 (s, 1H), 12.30 (br. s., 1H).

Example 7

N-[2-(2-Hydroxyethyl)-6-(hydroxymethyl)-2H-indazol-5-yl]-6-(trifluoromethyl)pyridine-2-carboxamide Stage A N-[2-(2-{[tert-Butyl(dimethyl)silyl]oxy}ethyl)-6-(hydroxymethyl)-2H-indazol-5-yl]-6-(trifluoromethyl)pyridine-2-carboxamide

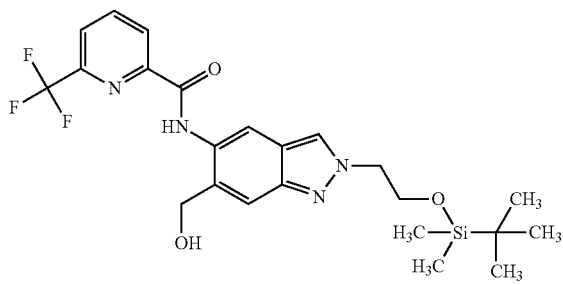 [SMILES: CC(C)(C)[Si](C)(C)OCCn1cc2cc(NC(=O)c3cccc(C(F)(F)F)n3)c(CO)cc2n1]

100 mg (0.19 mmol) of methyl 2-(2-{[tert-butyl(dimethyl)silyl]oxy}ethyl)-5-({[6-(trifluoromethyl)pyridin-2-yl]carbonyl}amino)-2H-indazole-6-carboxylate (Intermediate 4-5) were dissolved in 1 ml of THF and admixed with 191 μl (0.38 mmol) of a 2 M lithium borohydride solution. The mixture was left to stir at 25° C. for 24 h. 14 mg (0.38 mmol) of sodium borohydride and 500 μl of methanol were added, and the mixture was stirred at 25° C. for 4 h. Another 14 mg (0.38 mmol) of sodium borohydride were added, and the mixture was stirred at 25° C. for 24 h. Water was added cautiously to the reaction mixture and the organic phase was removed. The mixture was then extracted twice with ethyl acetate, and the combined organic phases were washed with saturated sodium chloride solution, filtered through a hydrophobic filter and concentrated. The residue was taken up in 2 ml of DMSO and purified by preparative HPLC. This gave 30 mg of N-[2-(2-{[tert-butyl(dimethyl)silyl]oxy}ethyl)-6-(hydroxymethyl)-2H-indazol-5-yl]-6-(trifluoromethyl)pyridine-2-carboxamide.

UPLC-MS (Method A2): $R_t$=1.44 min
MS (ESIpos): m/z=495 (M+H)$^+$ $^1$H NMR (300 MHz, DMSO-d6): δ [ppm]=-0.16--0.12 (m, 6H), 0.75-0.79 (m, 9H), 4.05 (t, 2H), 4.48 (t, 2H), 4.69 (d, 2H), 5.75-5.77 (m, 1H), 7.57 (s, 1H), 8.18 (dd, 1H), 8.30-8.33 (m, 1H), 8.38 (t, 1H), 8.45 (d, 1H), 8.51 (s, 1H), 11.20 (s, 1H).

Stage B

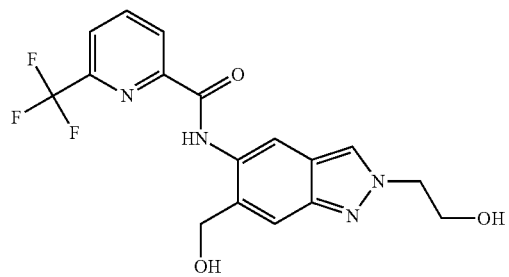 [SMILES: O=C(Nc1cc2cn(CCO)nc2cc1CO)c1cccc(C(F)(F)F)n1]

33 mg (0.07 mmol) of N-[2-(2-{[tert-butyl(dimethyl)silyl]oxy}ethyl)-6-(hydroxymethyl)-2H-indazol-5-yl]-6-(trifluoromethyl)pyridine-2-carboxamide were dissolved in 1 ml of THF and admixed with 100 μl (0.10 mmol) of a 1 M solution of tetrabutylammonium fluoride in THF. The reaction mixture was stirred at 25° C. for 1 h. The mixture was diluted with water and extracted twice with ethyl acetate, and the combined organic phases were washed with saturated sodium chloride solution, filtered through a hydrophobic filter, concentrated and dried under reduced pressure. 25 mg of N-[2-(2-hydroxyethyl)-6-(hydroxymethyl)-2H-indazol-5-yl]-6-(trifluoromethyl)pyridine-2-carboxamide (Example 7) were obtained.

UPLC-MS (Method A2): $R_t$=0.87 min
MS (ESIpos): m/z=381 (M+H)$^+$
$^1$H NMR (300 MHz, DMSO-d6): δ [ppm]=3.87 (q, 2H), 4.44 (t, 2H), 4.69 (d, 2H), 4.98 (t, 1H), 5.70-5.81 (m, 1H), 7.57 (s, 1H), 8.11-8.23 (m, 1H), 8.31-8.42 (m, 2H), 8.43-8.49 (m, 1H), 8.51 (s, 1H), 11.20 (s, 1H).

Example 8

N-[6-(2-Hydroxypropan-2-yl)-2-(oxetan-3-ylmethyl)-2H-indazol-5-yl]-6-(trifluoromethyl)pyridine-2-carboxamide

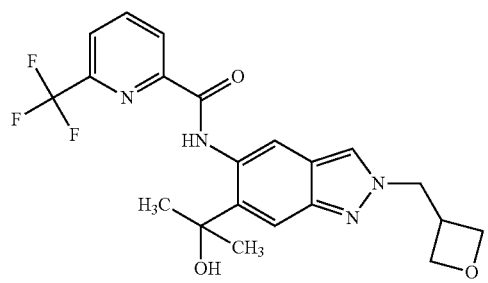 [SMILES: CC(C)(O)c1cc2nn(CC3COC3)cc2cc1NC(=O)c1cccc(C(F)(F)F)n1]

50 mg (0.12 mmol) of methyl 2-(oxetan-3-ylmethyl)-5-({[6-(trifluoromethyl)pyridin-2-yl]carbonyl}amino)-2H-indazole-6-carboxylate (Intermediate 4-1) were dissolved in 500 μl of THF and admixed with 576 μl (0.58 mmol) of a 1 M methylmagnesium bromide solution in THF. The reaction mixture was stirred at 25° C. for 60 min. Subsequently, 20 ml of a saturated aqueous ammonium chloride solution were added cautiously and the mixture was concentrated. The aqueous phase was extracted twice with ethyl acetate, and the organic phases were combined, dried over magnesium sulphate, filtered and concentrated. The residue was dissolved in 2.0 ml of DMSO and purified by preparative HPLC. The product-containing fractions were freeze-dried. 30 mg of the title compound were obtained.

UPLC-MS (Method A2): $R_t$=1.03 min

MS (ESIpos): m/z=435 (M+H)$^+$ $^1$H NMR (400 MHz, DMSO-d6): δ [ppm]=1.62 (s, 6H), 3.45-3.61 (m, 1H), 4.48 (t, 2H), 4.66 (dd, 2H), 4.72 (d, 2H), 5.94 (s, 1H), 7.57 (s, 1H), 8.16 (d, 1H), 8.33-8.42 (m, 2H), 8.42-8.47 (m, 1H), 8.72 (s, 1H), 12.36 (s, 1H).

Example 9

N-[6-(Hydroxymethyl)-2-(oxetan-3-ylmethyl)-2H-indazol-5-yl]-6-(trifluoromethyl)pyridine-2-carboxamide

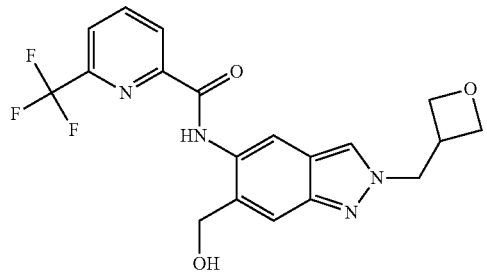 [SMILES: O=C(Nc1cc2cn(CC3COC3)nc2cc1CO)c1cccc(C(F)(F)F)n1]

75 mg (0.17 mmol) of methyl 2-(oxetan-3-ylmethyl)-5-({[6-(trifluoromethyl)pyridin-2-yl]carbonyl}amino)-2H-indazole-6-carboxylate (Intermediate 4-1) were dissolved in 1 ml of a mixture of THF/methanol (1:1), and 8 mg (0.21 mmol) of sodium borohydride were added. The mixture was left to stir at 25° C. for 60 min. The reaction mixture was concentrated, and the residue was admixed with water. The suspension was stirred vigorously for 15 min, and the solids were filtered off with suction, washed twice with water and twice with diethyl ether, and dried under reduced pressure. 48 mg of the title compound were obtained.

UPLC-MS (Method A2): $R_t$=0.94 min

MS (ESIpos): m/z=407 (M+H)$^+$ $^1$H NMR (300 MHz, DMSO-d6): δ [ppm]=3.55 (s, 1H), 4.48 (t, 2H), 4.61-4.77 (m, 6H), 7.57 (s, 1H), 8.18 (dd, 1H), 8.33-8.49 (m, 3H), 8.51 (s, 1H), 11.21 (s, 1H).

Example 10

N-{6-(2-Hydroxypropan-2-yl)-2-[3-(methylsulphonyl)propyl]-2H-indazol-5-yl}-6-(trifluoromethyl)pyridine-2-carboxamide

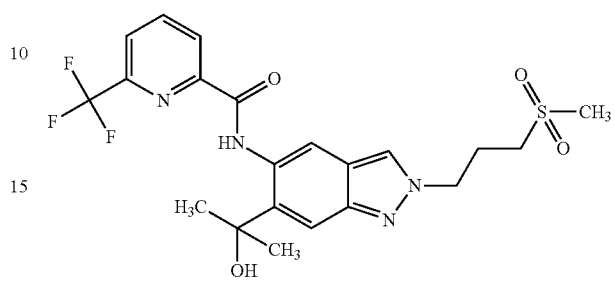

A mixture of 500 mg (1.32 mmol) of N-[6-(2-hydroxypropan-2-yl)-1H-indazol-5-yl]-6-(trifluoromethyl)pyridine-2-carboxamide (Intermediate 5-1), 569 mg of potassium carbonate and 114 mg of potassium iodide in 5.0 ml of DMF was stirred at room temperature for 15 min. 414 mg of 1-bromo-3-(methylsulphonyl)propane were added and the mixture was stirred at room temperature overnight. Water was added, the mixture was twice extracted with ethyl acetate and the extracts were washed with sodium chloride solution and concentrated. The residue was purified by column chromatography (dichloromethane/methanol gradient). Extracting the product fraction by stirring with diethyl ether gave 59 mg of the title compound.

UPLC-MS (Method A2): $R_t$=1.02 min

MS (ESIpos): m/z=485 (M+H)+

$^1$H-NMR (300 MHz, DMSO-d$_6$): δ [ppm]=1.63 (s, 6H), 2.26-2.42 (m, 2H), 2.99 (s, 3H), 3.06-3.16 (m, 2H), 4.55 (t, 2H), 5.96 (s, 1H), 7.60 (s, 1H), 8.16 (d, 1H), 8.33-8.48 (m, 3H), 8.73 (s, 1H), 12.37 (s, 1H).

Example 11

N-[2-(3-Hydroxy-3-methylbutyl)-6-(2-hydroxypropan-2-yl)-2H-indazol-5-yl]-6-(trifluoromethyl)pyridine-2-carboxamide

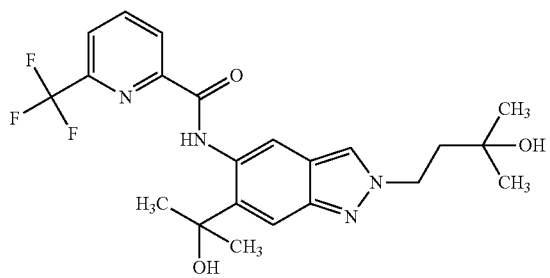 [SMILES: CC(C)(O)CCn1cc2cc(NC(=O)c3cccc(C(F)(F)F)n3)c(C(C)(C)O)cc2n1]

Preparation Method 1

705 mg (1.57 mmol) of methyl 2-(3-hydroxy-3-methylbutyl)-5-({[6-(trifluoromethyl)pyridin-2-yl]carbonyl}amino)-2H-indazole-6-carboxylate (Intermediate 4-4) were initially charged in 10 ml of THF and cooled in an ice-water cooling bath. 2.6 ml (5.0 equivalents) of 3M methylmagnesium bromide solution (in diethyl ether) were added and the mixture was left to stir while cooling with an ice bath for 1 h and at room temperature for 4.5 h. Another 1 equivalent of the methylmagnesium bromide solution was added and the mixture was left to stir at room temperature for 20.5 h. Another 1 equivalent again of the methylmagnesium bromide solution was added and the mixture was left to stir at room temperature for 22 h. The reaction mixture was admixed with saturated aqueous ammonium chloride solution, stirred and extracted three times with ethyl acetate. The combined organic phases were washed with sodium chloride solution, filtered through a hydrophobic filter and concentrated. This gave 790 mg of a residue which was purified by means of preparative HPLC. This gave 234 mg of the title compound and 164 mg of a product fraction which was extracted by stirring with diethyl ether. After filtration with suction followed by drying, a further 146 mg of the title compound were obtained.

UPLC-MS (Method A1): $R_t$=1.10 min (UV detector: TIC), mass found 450.00.

$^1$H-NMR (400 MHz, DMSO-$d_6$): δ [ppm]=1.14 (s, 6H), 1.61 (s, 6H), 1.99-2.08 (m, 2H), 4.42-4.55 (m, 3H), 5.93 (s, 1H), 7.56 (s, 1H), 8.15 (dd, 1H), 8.32-8.39 (m, 2H), 8.41-8.47 (m, 1H), 8.70 (s, 1H), 12.34 (s, 1H).

Preparation Method 2

A mixture of 500 mg (1.37 mmol) of N-[6-(2-hydroxypropan-2-yl)-1H-indazol-5-yl]-6-(trifluoromethyl)pyridine-2-carboxamide (Intermediate 5-1), 569 mg of potassium carbonate and 114 mg of potassium iodide in 5 ml of DMF was stirred at room temperature for 15 min. 344 mg (1.5 equivalents) of 4-bromo-2-methylbutan-2-ol were added and the mixture was heated to 100° C. for 2 h. Another 0.5 equivalent of 4-bromo-2-methylbutan-2-ol was added and the mixture was stirred at room temperature for 16 h. The mixture was admixed with water and extracted twice with ethyl acetate, and the combined organic phases were washed with saturated sodium chloride solution and filtered through a hydrophobic filter and concentrated. The residue was purified by column chromatography purification on silica gel (hexane/ethyl acetate). This gave 100 mg of a product fraction which was extracted by stirring with diethyl ether. After drying, 60 mg of the title compound were obtained.

$^1$H-NMR (400 MHz, DMSO-$d_6$): δ [ppm]=1.14 (s, 6H), 1.61 (s, 6H), 1.99-2.07 (m, 2H), 4.43-4.52 (m, 3H) 5.94 (s, 1H) 7.57 (s, 1H) 8.15 (dd, 1H) 8.33-8.40 (m, 2H) 8.42-8.48 (m, 1H), 8.71 (s, 1H), 12.35 (s, 1H)

Example 12

N-{6-(2-Hydroxypropan-2-yl)-2-[2-(methylsulphonyl)ethyl]-2H-indazol-5-yl}-6-(trifluoromethyl)pyridine-2-carboxamide

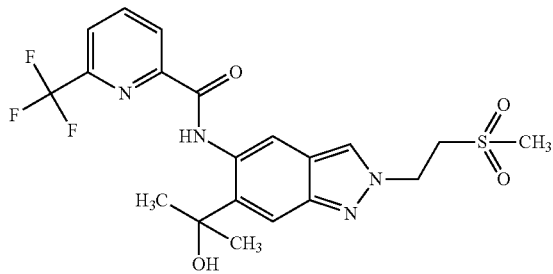 [SMILES: CC(C)(O)c1cc2nn(CCS(C)(=O)=O)cc2cc1NC(=O)c1cccc(C(F)(F)F)n1]

160 mg (0.44 mmol) of N-[6-(2-hydroxypropan-2-yl)-1H-indazol-5-yl]-6-(trifluoromethyl)pyridine-2-carboxamide (Intermediate 5-1) were suspended together with 182 mg of potassium carbonate and 36 mg of potassium iodide in 1.0 ml of DMF, and the mixture was stirred at room temperature for 15 min. Then 123 mg of 2-bromoethyl methyl sulphone (0.66 mmol) were added and the mixture was stirred at room temperature overnight. Water was added, the mixture was extracted twice with ethyl acetate and the extracts were washed with saturated aqueous sodium chloride solution, filtered through a hydrophobic filter and concentrated. Purification of the residue by preparative HPLC gave 20 mg of the title compound.

UPLC (Method A2): $R_t$=1.01 min;
MS (ESIpos): m/z=471 (M+H)+
$^1$H NMR (400 MHz, DMSO-$d_6$): δ [ppm]=1.63 (s, 6H), 2.90 (s, 3H), 3.85 (t, 2H), 4.86 (t, 2H), 5.97 (s, 1H), 7.59 (s, 1H), 8.13-8.19 (m, 1H), 8.37 (s, 1H), 8.41-8.48 (m, 2H), 8.74 (s, 1H), 12.37 (s, 1H).

Example 13

6-(Difluoromethyl)-N-[2-(3-hydroxy-3-methylbutyl)-6-(2-hydroxypropan-2-yl)-2H-indazol-5-yl]pyridine-2-carboxamide

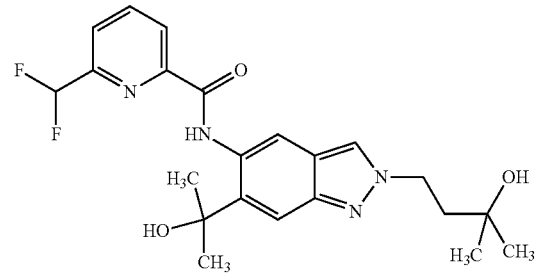 [SMILES: CC(C)(O)CCn1cc2cc(NC(=O)c3cccc(C(F)F)n3)c(C(C)(C)O)cc2n1]

Preparation Method 1

A mixture of 250 mg of 6-(difluoromethyl)-N-[6-(2-hydroxypropan-2-yl)-1H-indazol-5-yl]pyridine-2-carboxamide (crude product of Intermediate 5-2), 144 mg of potassium iodide and 239 mg of potassium carbonate in 2.5 ml of DMF was stirred at room temperature for 15 min. 145 mg (0.87 mmol) of 4-bromo-2-methylbutan-2-ol were added, the mixture was stirred at 110° C. for 3 h, another 96 mg of 4-bromo-2-methylbutan-2-ol were added and the mixture was stirred at 110° C. for 4 h. Water was added, the mixture was extracted twice with ethyl acetate and the extract was washed with semisaturated aqueous sodium chloride solution, filtered through a hydrophobic filter and concentrated. Purification was effected by column chromatography on silica gel (hexane/ethyl acetate). 61 mg of the title compound were obtained.

UPLC-MS (Method A1): $R_t$=1.00 min (UV detector: TIC), mass found 432.00.
$^1$H-NMR (300 MHz, DMSO-$d_6$): δ [ppm]=1.14 (s, 6H), 1.63 (s, 6H), 1.97-2.08 (m, 2H), 4.41-4.55 (m, 3H), 5.99 (s, 1H), 7.03 (t, 1H), 7.56 (s, 1H), 7.94-8.00 (m, 1H), 8.24-8.38 (m, 3H), 8.71 (s, 1H), 12.49 (s, 1H).

Preparation Method 2

Analogously to the preparation of Example 11 (Preparation Method 1), 3.00 g of methyl 5-({[6-(difluoromethyl)pyridin-2-yl]carbonyl}amino)-2-(3-hydroxy-3-methylbutyl)-2H-indazole-6-carboxylate (Intermediate 4-11) were reacted with 3M methylmagnesium bromide solution (in diethyl ether). After purification of the crude product by extractive stirring with diethyl ether followed by preparative HPLC, 1.37 g of the title compound were obtained.

Example 14

6-(Difluoromethyl)-N-{6-(2-hydroxypropan-2-yl)-2-[2-(methylsulphonyl)ethyl]-2H-indazol-5-yl}pyridine-2-carboxamide

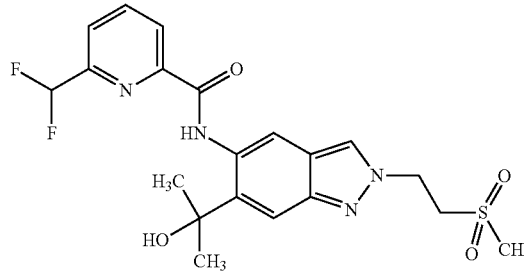 [SMILES: CC(C)(O)c1cc2nn(CCS(C)(=O)=O)cc2cc1NC(=O)c1cccc(C(F)F)n1]

A mixture of 250 mg of 6-(difluoromethyl)-N-[6-(2-hydroxypropan-2-yl)-1H-indazol-5-yl]pyridine-2-carboxamide (crude product of Intermediate 5-2), 144 mg of potassium iodide and 239 mg of potassium carbonate in 2.5 ml of DMF was stirred at room temperature for 15 min. 162 mg of 2-bromoethyl methyl sulphone (0.87 mmol) were added and the mixture was stirred at 110° C. for 3 h. Water was added, the mixture was extracted twice with ethyl acetate and the extract was washed with semisaturated aqueous sodium chloride solution, filtered through a hydrophobic filter and concentrated. The residue was purified by preparative HPLC and the product fractions were additionally purified by column chromatography purification on silica gel (hexane/ethyl acetate). 40 mg of the title compound were obtained.
$^1$H-NMR (400 MHz, DMSO-d$_6$): δ [ppm]=1.65 (s, 6H), 2.90 (s, 3H), 3.85 (t, 2H), 4.85 (t, 2H), 6.03 (s, 1H), 7.04 (t, 1H), 7.59 (s, 1H), 7.98 (d, 1H), 8.25-8.36 (m, 2H), 8.43 (s, 1H), 8.75 (s, 1H), 12.52 (s, 1H).

Example 15

6-(Difluoromethyl)-N-[6-(2-hydroxypropan-2-yl)-2-(3-hydroxypropyl)-2H-indazol-5-yl]pyridine-2-carboxamide Stage A Preparation of N-[2-(3-{[tert-butyl(dimethyl)silyl]oxy}propyl)-6-(2-hydroxypropan-2-yl)-2H-indazol-5-yl]-6-(difluoromethyl)pyridine-2-carboxamide

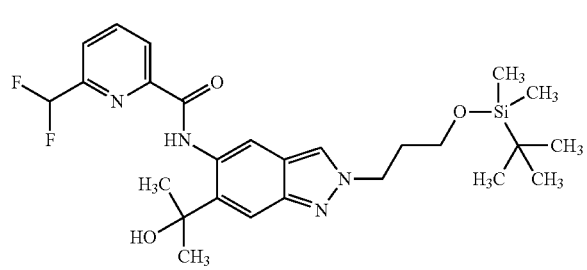 [SMILES: CC(C)(O)c1cc2nn(CCCO[Si](C)(C)C(C)(C)C)cc2cc1NC(=O)c1cccc(C(F)F)n1]

A mixture of 250 mg of 6-(difluoromethyl)-N-[6-(2-hydroxypropan-2-yl)-1H-indazol-5-yl]pyridine-2-carboxamide (Intermediate 5-2), 48 mg of potassium iodide and 239 mg of potassium carbonate in 2.5 ml of DMF was stirred at room temperature for 15 min. 219 mg (0.87 mmol, 1.5 equivalents) of (3-bromopropoxy)(tert-butyl)dimethylsilane were added and the mixture was stirred at 110° C. for 3 h. Another 1 equivalent of (3-bromopropoxy)(tert-butyl)dimethylsilane was added and the mixture was stirred at 100° C. for 4 h. Water was added, the mixture was extracted with ethyl acetate and the extract was washed with aqueous sodium chloride solution, filtered through a hydrophobic filter and concentrated. The residue was purified by column chromatography (hexane/ethyl acetate). 92 mg of the title compound were obtained.

Stage B

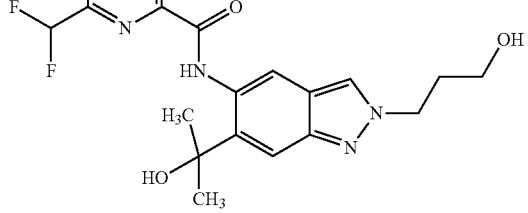

Analogously to the preparation of Example 6, Stage B, 92 mg of N-[2-(3-{[tert-butyl(dimethyl)silyl]oxy}propyl)-6-(2-hydroxypropan-2-yl)-2H-indazol-5-yl]-6-(difluoromethyl)pyridine-2-carboxamide were reacted with 0.53 ml of a 1 M solution of tetrabutylammonium fluoride in THF within 1 h. Aqueous workup as in Example 6 and purification by preparative HPLC gave 46 mg of the title compound.
UPLC-MS (Method A1): R$_t$=0.92 min (UV detector: TIC), mass found 404.00.
$^1$H-NMR (400 MHz, DMSO-d$_6$): δ [ppm]=1.64 (s, 6H), 2.05 (quin, 2H), 3.35-3.46 (m, 2H), 4.45 (t, 2H), 4.64 (t, 1H), 5.99 (s, 1H), 7.04 (t, 1H), 7.57 (s, 1H), 7.95-7.99 (m, 1H), 8.25-8.36 (m, 3H), 8.73 (s, 1H), 12.50 (s, 1H).

Example 16

N-[6-(2-Hydroxypropan-2-yl)-2-(4,4,4-trifluorobutyl)-2H-indazol-5-yl]-6-(trifluoromethyl)pyridine-2-carboxamide

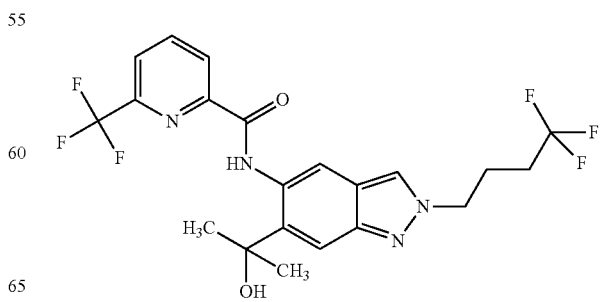

A mixture of 210 mg (0.58 mmol) of N-[6-(2-hydroxypropan-2-yl)-1H-indazol-5-yl]-6-(trifluoromethyl)pyridine-2-carboxamide (Intermediate 5-1) in 3 ml of DMF was admixed with 0.11 ml (0.87 mmol) of 1,1,1-trifluoro-4-iodobutane and 239 mg of potassium carbonate, and the mixture was stirred at 80° C. for 6 h. After addition of water, the mixture was extracted three times with ethyl acetate, and the combined organic phases were washed with saturated sodium chloride solution, filtered through a hydrophobic filter and concentrated. The crude product was purified by preparative HPLC. 19 mg of the title compound were obtained.

UPLC-MS (Method A1): $R_t$=1.27 min (UV detector: TIC), mass found 474.15.

$^1$H-NMR (400 MHz, DMSO-$d_6$): δ [ppm]=1.62 (s, 6H), 2.10-2.33 (m), 4.49 (t, 2H), 5.94 (s, 1H), 7.59 (s, 1H), 8.13-8.18 (m, 1H), 8.32-8.41 (m, 2H), 8.41-8.47 (m, 1H), 8.72 (s, 1H), 12.35 (s, 1H).

Example 17

N-{6-(2-Hydroxypropan-2-yl)-2-[3-(trifluoromethoxy)propyl]-2H-indazol-5-yl}-6-(trifluoromethyl)pyridine-2-carboxamide

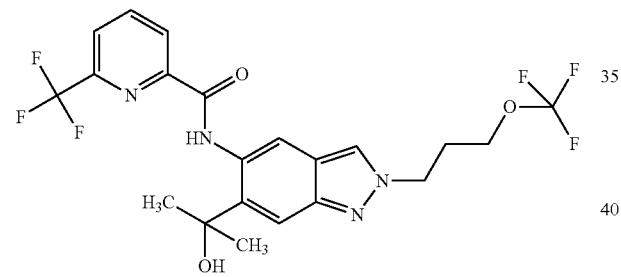 [SMILES: CC(C)(O)c1cc2nn(CCCOCC(F)(F)F)cc2cc1NC(=O)c1cccc(C(F)(F)F)n1]

150 mg (0.33 mmol) of N-[6-(2-hydroxypropan-2-yl)-1H-indazol-5-yl]-6-(trifluoromethyl)pyridine-2-carboxamide (Intermediate 5-1) were initially charged in 2 ml of THF. 58 mg (0.40 mmol) of 3-(trifluoromethoxy)propan-1-ol, 131 mg of triphenylphosphine and 71 μl of diisopropyl azodicarboxylate (DIAD, CAS 2446-83-5) were added and the mixture was stirred at room temperature for 19 h. 0.83 ml of sodium hydroxide solution (2M) was added and the mixture was stirred at 40° C. for 5 h. The mixture was diluted with water and extracted three times with ethyl acetate, and the combined organic phases were concentrated and purified by preparative HPLC. 16 mg of the title compound were obtained as a crude product.

UPLC-MS (Method A2): $R_t$=1.26 min (UV detector: TIC), mass found 490.14.

$^1$H-NMR (400 MHz, DMSO-$d_6$, selected signals): δ [ppm]=1.61 (s, 6H), 1.84 (d, 1H), 2.32 (quint., 2H), 4.08 (t, 2H), 4.51 (t, 2H), 7.58 (s, 1H), 8.15 (d, 1H), 8.31-8.39 (m, 2H), 8.44 (d, 1H), 8.72 (s, 1H), 12.35 (s, 1H).

Example 18

N-{6-(2-Hydroxypropan-2-yl)-2-[3-(2,2,2-trifluoroethoxy)propyl]-2H-indazol-5-yl}-6-(trifluoromethyl)pyridine-2-carboxamide

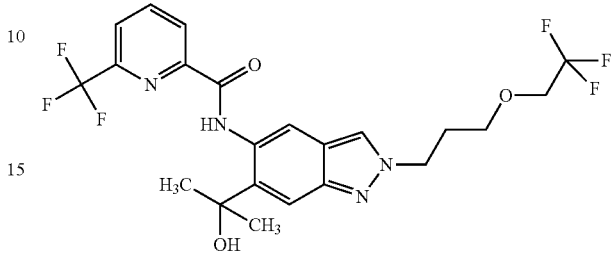

Analogously to the preparation of Example 11 (Preparation Method 1), 52 mg (0.10 mmol) of methyl 2-[3-(2,2,2-trifluoroethoxy)propyl]-5-({[6-(trifluoromethyl)pyridin-2-yl]carbonyl}amino)-2H-indazole-6-carboxylate (Intermediate 4-10) in 3 ml of THF were reacted with 2×171 μl of 3M magnesium bromide solution in diethyl ether. Purification by preparative HPLC gave 12 mg of the title compound.

UPLC-MS (Method A1): $R_t$=1.25 min (UV detector: TIC), mass found 504.16.

$^1$H-NMR (500 MHz, DMSO-$d_6$): δ [ppm]=1.63 (s, 6H), 2.20 (quin, 2H), 3.58 (t, 2H), 4.05 (q, 2H), 4.47 (t, 2H), 5.94 (s, 1H), 7.58 (s, 1H), 8.15 (dd, 1H), 8.32 (s, 1H), 8.36 (t, 1H), 8.45 (d, 1H), 8.73 (s, 1H), 12.36 (s, 1H).

Example 19

5-Fluoro-N-[2-(3-hydroxy-3-methylbutyl)-6-(2-hydroxypropan-2-yl)-2H-indazol-5-yl]-6-methylpyridine-2-carboxamide

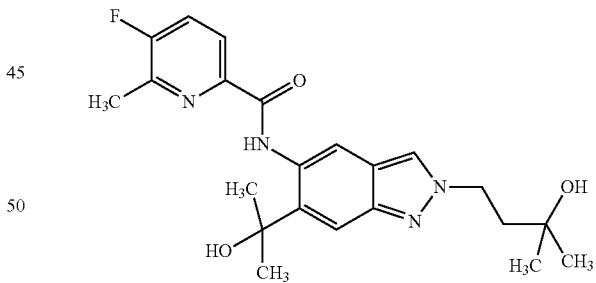

228 mg (0.31 mmol) of methyl 5-{[(5-fluoro-6-methylpyridin-2-yl)carbonyl]amino}-2-(3-hydroxy-3-methylbutyl)-2H-indazole-6-carboxylate (Intermediate 4-8) were initially charged in 4.5 ml of THF and cooled with an ice cooling bath. 0.63 ml of 3M methylmagnesium bromide solution (in diethyl ether) was added and the mixture was left to stir while cooling with an ice bath for 2 h and at room temperature for 21 h. The reaction mixture was admixed with saturated aqueous ammonium chloride solution and extracted three times with ethyl acetate. The combined organic phases were concentrated. The residue was purified by preparative HPLC. 82 mg of the title compound were obtained.

UPLC-MS (Method A2): $R_t$=1.03 min (UV detector: TIC), mass found 414.21.

$^1$H-NMR (400 MHz, DMSO-$d_6$): δ [ppm]=1.13 (s, 6H), 1.63 (s, 6H), 1.99-2.05 (m, 2H), 2.55-2.59 (m, 3H), 4.42-4.50 (m, 3H), 5.95 (s, 1H), 7.54 (s, 1H), 7.83 (t, 1H), 8.05 (dd, 1H), 8.31 (s, 1H), 8.68 (s, 1H), 12.33 (s, 1H).

Example 20

N-[2-(3-Hydroxy-3-methylbutyl)-6-(2-hydroxypropan-2-yl)-2H-indazol-5-yl]-6-methylpyridine-2-carboxamide

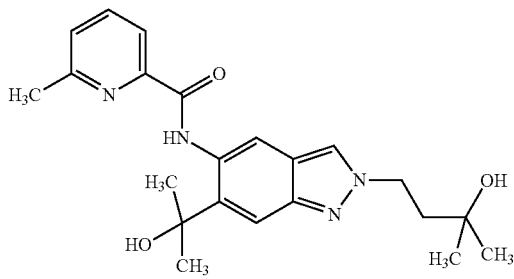 [SMILES: Cc1cccc(C(=O)Nc2cc3cn(CCC(C)(C)O)nc3cc2C(C)(C)O)n1]

278 mg (0.48 mmol) of methyl 2-(3-hydroxy-3-methylbutyl)-5-{[(6-methylpyridin-2-yl)carbonyl]amino}-2H-indazole-6-carboxylate (Intermediate 4-9) were initially charged in 5.0 ml of THF and cooled with an ice cooling bath. 0.97 ml of 3M methylmagnesium bromide solution (in diethyl ether) was added and the mixture was left to stir while cooling with an ice bath for 2 h and at room temperature for 20.5 h. Another 0.48 ml of 3M methylmagnesium bromide solution was added and the mixture was left to stir at room temperature for 67 h. The mixture was admixed with saturated aqueous ammonium chloride solution and extracted three times with ethyl acetate, and the extracts were washed with sodium chloride solution, filtered through a hydrophobic filter and concentrated. The residue was purified by preparative HPLC. 111 mg of the title compound were obtained.

UPLC-MS (Method A2): $R_t$=0.97 min (UV detector: TIC), mass found 396.22.

$^1$H-NMR (400 MHz, DMSO-$d_6$): δ [ppm]=1.15 (s, 6H), 1.64 (s, 6H), 2.00-2.08 (m, 2H), 2.61 (s, 3H), 4.41-4.59 (m, 3H), 5.92 (s, 1H), 7.50 (dd, 1H), 7.56 (s, 1H), 7.90-7.99 (m, 2H), 8.33 (s, 1H), 8.70 (s, 1H), 12.39 (s, 1H).

Example 21

6-(2-Hydroxypropan-2-yl)-N-[6-(2-hydroxypropan-2-yl)-2-(4,4,4-trifluorobutyl)-2H-indazol-5-yl]pyridine-2-carboxamide

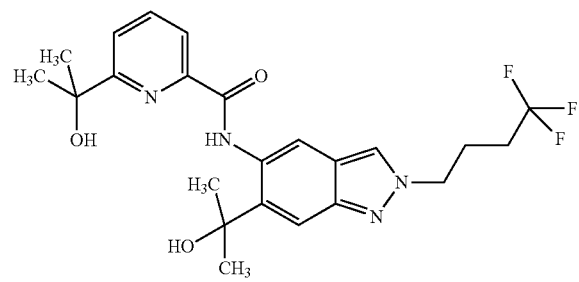 [SMILES: CC(C)(O)c1cccc(C(=O)Nc2cc3cn(CCCC(F)(F)F)nc3cc2C(C)(C)O)n1]

A solution of 72 mg (0.16 mmol) of methyl 5-({[6-(2-hydroxypropan-2-yl)pyridin-2-yl]carbonyl}amino)-2-(4,4,4-trifluorobutyl)-2H-indazole-6-carboxylate (Intermediate 4-7) in 10 ml of THF was cooled in an ice/water cooling bath. 0.26 ml of 3M methylmagnesium bromide solution in diethyl ether was added and the mixture was stirred for 2 h and then at room temperature for 20 h. Another 1 equivalent of the 3M methylmagnesium bromide solution was added and the mixture was stirred at room temperature for 24 h. Saturated aqueous ammonium chloride solution was added, the mixture was three times extracted with ethyl acetate and the extracts were washed with sodium chloride solution and concentrated. Preparative HPLC gave 22 mg (31% of theory) of the title compound.

UPLC-MS (Method A2): $R_t$=1.15 min (UV detector: TIC), mass found 464.20.

$^1$H-NMR (400 MHz, DMSO-$d_6$): δ [ppm]=1.56 (s, 6H), 1.64 (s, 6H), 2.07-2.34 (m, 4H), 4.49 (t, 2H), 5.32 (s, 1H), 6.05 (s, 1H), 7.60 (s, 1H), 7.87 (dd, 1H), 7.99-8.05 (m, 2H), 8.35 (s, 1H), 8.79 (s, 1H), 12.45 (s, 1H).

Example 22

N-{2-[2-(1-Hydroxycyclopropyl)ethyl]-6-(2-hydroxypropan-2-yl)-2H-indazol-5-yl}-6-(trifluoromethyl)pyridine-2-carboxamide

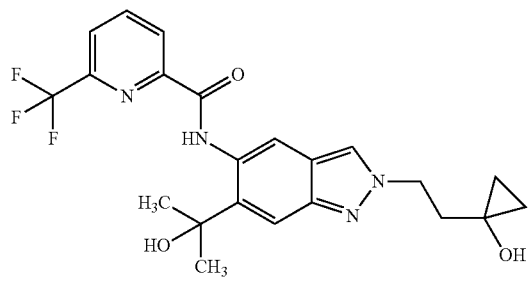 [SMILES: CC(C)(O)c1cc2nn(CCC3(O)CC3)cc2cc1NC(=O)c1cccc(C(F)(F)F)n1]

250 mg (0.69 mmol) of N-[6-(2-hydroxypropan-2-yl)-1H-indazol-5-yl]-6-(trifluoromethyl)pyridine-2-carboxamide (Intermediate 5-1) were initially charged in 5 ml of DMSO. 159 mg (0.96 mmol) of 1-(2-bromoethyl)cyclopropanol, 285 mg of potassium carbonate and 171 mg of potassium iodide were added and the mixture was stirred at 100° C. for 5 h. Water was added and the mixture was extracted three times with ethyl acetate. The combined organic phases were washed with sodium chloride solution, filtered through a hydrophobic filter and concentrated. The residue was purified by preparative HPLC (column: Waters XBridge C18 5μ 100×30 mm, eluent A: water+0.1% by volume of formic acid (99%), eluent B: acetonitrile). Freeze-drying gave 45 mg of the title compound.

$^1$H-NMR (500 MHz, DMSO-d6): δ [ppm]=0.18-0.22 (m, 2H), 0.48-0.52 (m, 2H), 1.62 (s, 6H), 2.08 (t, 2H), 4.54-4.60 (m, 2H), 5.36 (s, 1H), 5.96 (s, 1H), 7.57 (s, 1H), 8.16 (dd, 1H), 8.34-8.39 (m, 2H), 8.45 (d, 1H), 8.72 (s, 1H), 12.36 (s, 1H).

Assessment of Physiological Efficacy in Various Autoimmune Disorders

IRAK4 Kinase Assay

The IRAK4-inhibitory activity of the inventive substances was measured in the IRAK4 TR-FRET assay (TR-FRET=Time Resolved Fluorescence Resonance Energy Transfer) described hereinafter.

Recombinant fusion protein from N-terminal GST (glutathione S-transferase) and human IRAK4, expressed in baculovirus-infected insect cells (Hi5, BTI-TN-5B1-4, cell line purchased from Invitrogen, catalogue No. B855-02) and purified via affinity chromatography, was used as enzyme. The substrate used for the kinase reaction was the biotinylated peptide biotin-Ahx-KKARFSRFAGSSPSQAS-FAEPG (C-terminus in amide form) which can be purchased, for example, from Biosyntan GmbH (Berlin-Buch).

For the assay, 11 different concentrations in the range from 20 µM to 0.073 nM were prepared from a 2 mM solution of the test substance in DMSO. 50 nl of the respective solution were pipetted into a black low-volume 384-well microtitre plate (Greiner Bio-One, Frickenhausen, Germany), 2 µl of a solution of IRAK4 in assay buffer [50 mM HEPES pH 7.5, 5 mM MgCl2, 1.0 mM dithiothreitol, 30 µM activated sodium orthovanadate, 0.1% (w/v) of bovine gamma-globulin (BGG), 0.04% (v/v) nonidet-P40 (Sigma)] were added and the mixture was incubated for 15 min to allow prebinding of the substances to the enzyme prior to the kinase reaction. The kinase reaction was then started by addition of 3 µl of a solution of adenosine triphosphate (ATP, 1.67 mM=final concentration in 5 µl of assay volume: 1 mM) and peptide substrate (0.83 µM=final concentration in 5 µl assay volume: 0.5 µM) in assay buffer, and the resulting mixture was incubated at 22° C. for the reaction time of 45 min. The concentration of the IRAK4 was adjusted to the respective activity of the enzyme and set such that the assay was carried out in the linear range. Typical concentrations were in the order of about 0.2 nM. The reaction was stopped by addition of 5 µl of a solution of TR-FRET detection reagents [0.1 µM streptavidin-XL665 (Cisbio Bioassays; France, catalogue No. 610SAXLG)] and 1.5 nM anti-phosphoserine antibody [Merck Millipore, "STK Antibody", catalogue No. 35-002] and 0.6 nM LANCE EU-W1024-labelled anti-mouse-IgG antibody (Perkin-Elmer, product No. AD0077; alternatively, it is possible to use a terbium cryptate-labelled anti-mouse-IgG antibody from Cisbio Bioassays) in aqueous EDTA solution (100 mM EDTA, 0.4% [w/v] bovine serum albumin [BSA] in 25 mM HEPES pH 7.5).

The resulting mixture was incubated at 22° C. for 1 h to allow formation of a complex of the biotinylated phosphorylated substrate and the detection reagents. The amount of the phosphorylated substrate was then evaluated by measuring the resonance energy transfer from europium chelate-labelled anti-mouse-IgG antibody to streptavidin-XL665. To this end, the fluorescence emissions at 620 nm and 665 nm were measured after excitation at 350 nm in a TR-FRET measuring instrument, for example a Rubystar (BMG Labtechnologies, Offenburg, Germany) or a Viewlux (Perkin-Elmer). The ratio of the emissions at 665 nm and 622 nm was taken as a measure of the amount of phosphorylated substrate. The data were normalized (enzyme reaction without test substance=0% inhibition; all other assay components but no enzyme=100% inhibition). Typically, the test substances were tested on the same microtitre plates at 11 different concentrations in the range from 20 µM to 0.073 nM (20 µM, 5.7 µM, 1.6 µM, 0.47 µM, 0.13 µM, 38 nM, 11 nM, 3.1 nM, 0.89 nM, 0.25 nM and 0.073 nM). The dilution series were prepared prior to the assay (2 mM to 7.3 nM in 100% DMSO) by serial dilutions. The $IC_{50}$ values were calculated by a 4-parameter fit.

TABLE 1

$IC_{50}$ values compounds in the IRAK4 kinase assay of the example

| Example | $IC_{50}$ [nM] |
|---|---|
| 1 | 30.6 |
| 2 | 135.6 |
| 3 | 7.2 |
| 4 | 52.7 |
| 5 | 264.5 |
| 6 | 35.7 |
| 7 | 867.3 |
| 8 | 15.0 |
| 9 | 103.8 |
| 10 | 18.5 |
| 11 | 3.4 |
| 12 | 10.7 |
| 13 | 1.3 |
| 14 | 10.8 |
| 15 | 12.3 |
| 16 | 21.5 |
| 17 | 36.0 |
| 18 | 47.5 |
| 19 | 8.9 |
| 20 | 13.3 |
| 21 | 117.2 |
| 22 | 3.7 |

The inhibitory activity of the compounds of the general formula (III) with respect to IRAK4 was likewise measured in the IRAK4 TR-FRET assay described above. The following are mentioned by way of example: the compound Intermediate 4-2 with an $IC_{50}$=21.7 nM, Intermediate 4-3 with an $IC_{50}$=13.0 nM and Intermediate 4-4 with an $IC_{50}$=6.2 nM.

TNF-α Secretion in THP-1 Cells

With the aid of this test, it is possible to test substances for their ability to inhibit secretion of TNF-α (tumour necrosis factor alpha) in THP-1 cells (human monocytic acute leukaemia cell line). TNF-α is a key cytokine involved in inflammatory processes of the cited autoimmune disorders such as rheumatoid arthritis, psoriatic arthritis, Bekhterev's disease, psoriasis, Crohn's disease, ulcerative colitis, etc. In this test, TNF-α secretion is triggered by incubation with bacterial lipopolysaccharide (LPS).

THP-1 cells were kept in continuous suspension cell culture [RPMI 1460 medium with L-Glutamax (Gibco, Cat. No. 61870-044) supplemented with foetal calf serum (FCS) 10% (Invitrogen, Cat. No. 10082-147), 1% penicillin/streptomycin (Gibco BRL, Cat. No. 15140-114)] and should not exceed a cell concentration of $1 \times 10^6$ cells/ml. The assay is carried out in cell culture medium (RPMI 1460 medium with L-Glutamax supplemented with FCS 10%).

In each case 2-2.5 µl of the cell suspension (corresponds to 4000 cells) per well were dispensed into a 384-well test plate (Greiner, Cat. No. 784076), in each of which 40-50 nl substance had been dissolved in 100% DMSO. This was done using 10 different concentrations in the range from 20 µM to 0.073 nM for each substance. The cells were incubated at room temperature for 15 min. 2-2.5 µl of 0.1 µg/ml LPS (Sigma, *Escherichia coli* 055:B5, Cat. No. L5418) dissolved in cell culture medium (final concentration 0.05 µg/ml) were then dispensed into each well. As neutral control, cells were treated with 0.05 µg/ml LPS and 1% DMSO and, as inhibitor control, with 1% DMSO only.

The plates were centrifuged at 80 g for 30 s and incubated at 37° C., 5% $CO_2$ and 95% atmospheric humidity for 17 h. The amount of TNF-α was determined using the TNF-alpha HTRF Detection Kit (Cisbio, Cat. No. 62TNFPEB/C). To this end, 2 µl of the detection solution in each case, consisting of anti-TNF-α-XL665 conjugate and anti-TNF-α-cryptate conjugate dissolved in the reconstitution buffer in accordance with the manufacturer's instructions, were added for the HTRF (Homogeneous Time-Resolved Fluorescence) test. After the addition, the mixture was incubated either at room temperature for 3 h or at 4° C. overnight. The signals were then read at 620/665 nm using an HTRF-enabled measuring instrument such as the BMG PheraStar.

The activity of the substances is expressed as the ratio between neutral and inhibitor control in percent. The $IC_{50}$ values were calculated using a 4-parameter fit.

TABLE 2

$IC_{50}$ values of the example compounds with respect to the secretion of TNF-α in THP-1 cells

| Example | $IC_{50}$ [nM] |
|---|---|
| 1 | 1.0 |
| 2 | 15.1 |
| 3 | 0.7 |
| 4 | 5.6 |
| 5 | 5.4 |
| 6 | 0.9 |
| 7 | 16.4 |
| 8 | 1.0 |
| 9 | 6.5 |
| 10 | 1.0 |
| 11 | 0.2 |
| 12 | 0.3 |
| 13 | 0.1 |
| 14 | 0.2 |
| 15 | 0.2 |
| 16 | 0.2 |
| 17 | 0.5 |
| 18 | 0.3 |
| 19 | 0.1 |
| 20 | 0.2 |
| 21 | 1.8 |

In Vitro LPS (Lipopolysaccharide)-Induced Cytokine Production in Human PBMCs (Peripheral Blood Mononuclear Cells)

The effect of the compounds of the general formula (I) on induced cytokine production in human PBMCs was examined. Cytokine production was induced here by LPS, a TLR4 ligand, which leads to activation of the IRAK4-mediated signal path.

The human PBMCs were obtained from anti-coagulated human whole blood. For this purpose, 15 ml of Ficoll-Paque (Biochrom, Cat. No. L6115) were initially charged in Leucosep tubes and 20 ml of human blood were added. After centrifugation of the blood at 800 g for 15 min at room temperature, the plasma including the platelets was removed and discarded. The PBMCs were transferred into centrifugation tubes and made up with PBS (phosphate-buffered saline) (Gibco, Cat. No. 14190). The cell suspension was centrifuged at room temperature at 250 g for 10 min and the supernatant was discarded. The PBMCs were resuspended in complete medium (RPMI 1640, without L-glutamine (PAA, Cat. No. E15-039), 10% FCS; 50 U/ml penicillin, 50 µg/ml streptomycin (PAA, Cat. No. P11-010) and 1% L-glutamine (Sigma, Cat. No. G7513)).

The assay was also carried out in complete medium. The PBMCs were sown in 96-well plates at a cell density of $2.5 \times 10^5$ cells/well. The compounds of the general formula (I) were subjected to serial dilution in a constant volume of 100% DMSO and used in the assay at 8 different concentrations in the range from 10 µM to 3 nM such that the final DMSO concentration was 0.4% DMSO. Prior to the actual stimulation, the cells were then pre-incubated therewith for 30 min. To induce cytokine secretion, the cells were stimulated with 0.1 µg/ml LPS (Sigma, Escherichia coli 0128: B12, Cat. No. L2887) for 24 hours. Cell viability was determined using the CellTiter-Glo luminescent assay (Promega, Cat. No. G7571 (G755/G756A)) in accordance with the manufacturer's instructions. The amount of secreted TNF-α in the cell culture supernatant was determined using the Human ProInflammatory 9-Plex Tissue Culture Kit (MSD, Cat. No. K15007B) in accordance with the instructions of the manufacturer. By way of example, Example Compound 11 and Example Compound 12 have activity≤1 µM.

In Vitro TLR4/TLR7-Induced Interleukin (IL)-23 Secretion of Human Dendritic Cells (DCs)

The effect of the compounds of the general formula (I) on the induced production of the proinflammatory cytokine IL-23 which plays an essential role for the generation of TH-17 cells (IL-17-producing T-helper cells) was examined in human DCs. It is stated that TH-17 cells play a crucial role in the pathogenesis of disorders such as rheumatoid arthritis, psoriatic arthritis, Bekhterev's disease (ankylosing spondylitis), psoriasis, atopic dermatitis, systemic lupus erythematosus or else multiple sclerosis (Lubberts, Nat. Rev. Rheumatol., 2015; Marinoni et al., Auto. Immun. Highlights, 2014; Isailovic et al., J. Autoimmun., 2015; Richtlin & Krueger, Curr Opin Rheumatol. 2016 May; 28(3):204-10 Leonardi et al., Allergy Asthma Proc. 2015; Araújo et al., Rev Bras Rheumatol. 2016; Staschke et al., J Immunol., 2009). To detect the effect of the compounds of the general formula (I) on IL-23 production, human primary monocytes (isolated from human PBMCs with the aid of magnetic separation [Miltenyi Biotech, Monocyte Isolation Kit, Cat. No. 130-091-153] with addition of growth factors (recombinant human GM-CSF [PeproTech, Cat. No. 300-03] and IL-4 [PeproTech, Cat. No. 200-04]) in complete medium (VLE (very low endotoxin) RPMI 1640 [Biochrom AG, Cat. No. FG1415], 10% Fetal Bovine Serum (FBS) [Gibco, Cat-No. 10493-106]; 50 µM β-mercaptoethanol [Gibco, Cat. No. 31350], 50 U/ml penicillin and streptomycin [Gibco, Cat. No. 15140-114]) were differentiated in culture over 6 days to give DCs. After the DCs had been harvested, they were resuspended in complete medium and sown in a cell density of $2 \times 10^7$ cells/well in a 96-well plate (Costar, Cat. No. 3599). The compounds of the general formula (I) were subjected to serial dilution in a constant volume of 100% DMSO and used in the assay at 9 different concentrations in the range from 10 µM to 1 nM. It was ensured here that the DMSO concentration present was always 0.1% DMSO for each of the 9 concentrations used. There was a 30-minute preincubation of the DCs with the compounds of the general formula (I). Thereafter, the DCs were then stimulated to produce IL-23 by means of 10 ng/ml of LPS (Sigma, Escherichia coli serotype 0127:B8, Cat. No. L3129) (TLR4 ligand) and 2.5 µg/ml of TLR7/8 ligand R848 (Invivogen, Cat. No. tlrl-r848-5), both of which bring about the activation of the IRAK4-mediated signalling pathway, in an incubator (37° C., 95% rH, 5% $CO_2$) for 24 hours. After this incubation time of 24 hours, the supernatants were removed and analysed with the aid of a commercially available hIL-23 ELISA (eBiosciences, Cat. No. 88-7237-88), which was conducted according to the manufacturer's instructions.

The results of the inhibition of IL-23 in human DCs are shown by way of example for Example Compound 12 in FIG. 1.

In Vitro Stimulation of Human Th17 Cells for Secretion of Interleukin (IL)-17

Figure 2A:
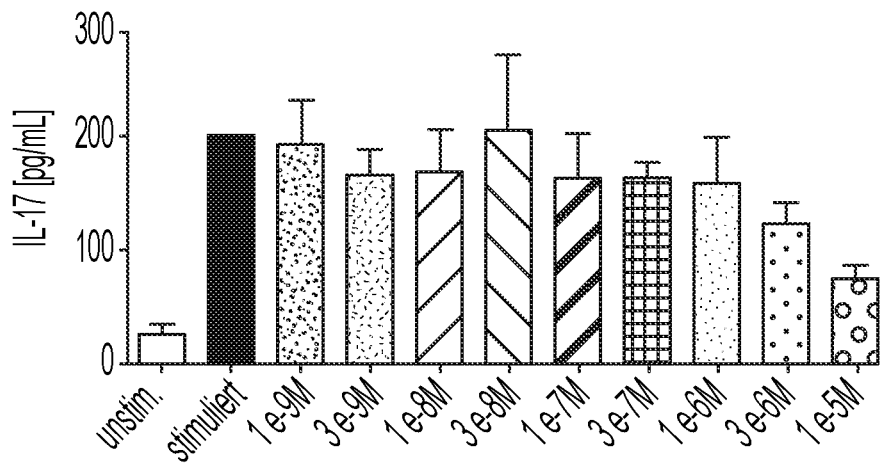
FIG. 2A: Inhibition of 6-day Th17 cell differentiation measured by the production of IL-17 after stimulation of human CD4+ T cells with anti-CD3/anti-CD28/rhIL-23/rhIL-6/rhl-1beta/rhIL-2 (TH17 cell differentiation cocktail), shown in an exemplary manner for Example Compound 12 for a first donor. Data is shown as mean values with standard deviations.
Figure 2B:
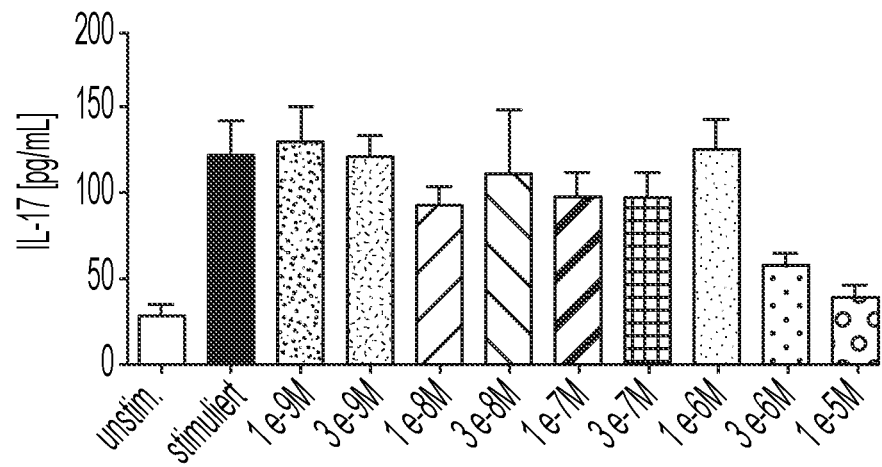
FIG. 2B: Inhibition of 6-day Th17 cell differentiation measured by the production of IL-17 after stimulation of human CD4+T cells with_anti-CD3/anti-CD28/rhIL-23/rhIL-6/rhl-1beta/rhIL-2 (TH17 cell differentiation cocktail), shown in an exemplary manner for Example Compound 12 for a second donor. Data is shown as mean values with standard deviations.

The inhibitory action of the compounds of the general formula (I) on induced production of the proinflammatory cytokine IL-17, which is considered to be a key cytokine in the pathogenesis of rheumatoid arthritis, psoriatic arthritis, Bechterew disease (ankylosing spondylitis), reactive arthritis, psoriasis, atopic dermatitis, systemic lupus erythematosus, chronic-inflammatory bowel diseases and also multiple sclerosis, was investigated in human Th17 cells. To this end, first, human PBMCs were obtained from anticoagulated human whole blood as follows: 20 ml of human blood were added to leucosep tubes which had been initially charged with 15 ml of Ficoll-Paque (Biochrom, Cat. No. L6115) beforehand. The blood was centrifuged at 800 g for 15 min at room temperature, and plasma including platelets was then removed and discarded. The PBMCs were transferred into centrifuge tubes and made up with PBS (phosphate-buffered saline) (Gibco, Cat. No. 14190). The cell suspension was centrifuged at 250 g for 10 min at room temperature, and the supernatant was discarded. The PBMCs were resuspended in complete medium (RPMI 1640, without L-glutamine (PAA, Cat. No. E15-039), 10% FCS; 50 U/ml penicillin, 50 µg/ml streptomycin (PAA, Cat. No. P11-010) and 1% L-glutamine (Sigma, Cat. No. G7513)). Subsequently, CD4+ T-cells were isolated by magnetic cell separation (CD4+ T cell isolation kit, Miltenyi Biotech, Cat. No. 130-096-533) on a column (LS column, Miltenyi Biotech, Cat. No. 130-042-401) from the PBMCs. The CD4+ T cells obtained in this manner were sown in 96-well plates (flat bottom, Costar, Cat. No. 3599) at a cell density of $5 \times 10^4$ CD4+ T cells/well. This assay, too, was carried out using complete medium. The compounds of the general formula (I) were subjected to serial dilution in a constant volume of 100% DMSO and employed in the assay at 9 different concentrations in the range from 10 µM to 1 nM such that the final DMSO concentration was 0.1% DMSO. The cells were preincubated with the respective concentration of the compounds of the general formula (I) in an incubator for 30 minutes. A Th17 differentiation cocktail consisting of anti-CD3/anti-CD28 beads (2500 beads per 50 000 cells; T cell activation kit, Miltenyi Biotech, Cat. No. 130-091-441), recombinant human (rh) IL-23 (20 ng/ml; eBioscience, Cat. No. 14-8239-63), rhIL-1beta (20 ng/ml; eBioscience, Cat. No. 34-8018), rhIL-6 (20 ng/ml; eBioscience, Cat. No. 34-8069) and rhIL-2 (100 IU/ml; eBioscience, Cat. No. SRP3085), with the aid of which the CD4+ T cells differentiated to Th17 cells over 6 days and were simultaneously stimulated to produce IL-17, was then added. After 6 days of cultivation in the incubator the cell culture supernatants were removed and analysed using a commercial hIL-17 ELISA (human IL-17a ELISA Ready-SET-Go, eBiosciences, Cat. No. 88-7176-88), which was carried out according to the instructions of the manufacturer. The results of the inhibition of Th17 cell differentiation and thus ultimately also IL-17 production are shown by way of example for Example Compound 12 in FIG. 2A and FIG. 2B.

In Vitro TLR7/8- or TLR9-Induced IFN-α Production of Human Plasmacytoid Dendritic Cells (pDCs)

Figure 3A:
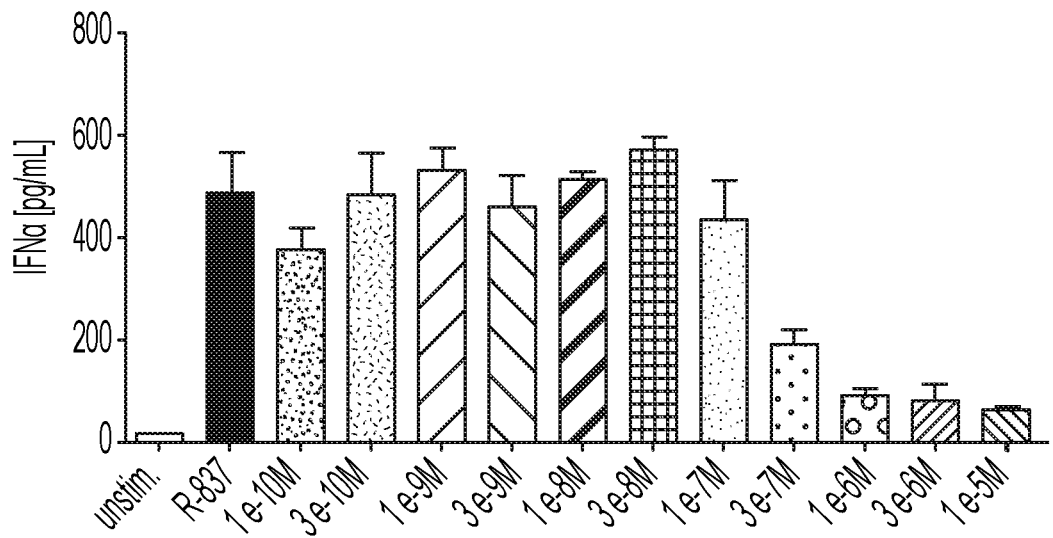
FIG. 3A: Inhibition of INF-α in imiquimod (R837, TLR7/8 ligand)-stimulated human plasmacytoid DCs for Example Compound 12. Data is shown as mean values with standard deviations.
Figure 3B:
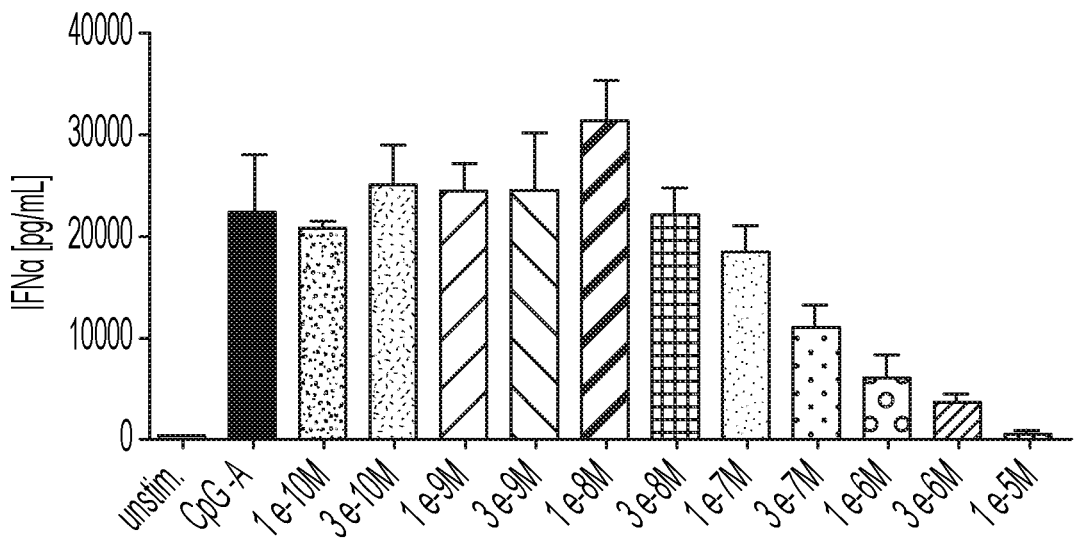
FIG. 3B: Inhibition of INF-α in CpG-A-(TLR9 ligand)-stimulated human plasmacytoid DCs for Example Compound 12. Data is shown as mean values with standard deviations.

With the aid of this test, the effect of the compounds of the general formula (I) on the production of IFN-α (interferon-alpha), a key cytokine in the pathogenesis of systemic lupus erythematosus (Mathian et al., Arthritis Rheum, 2009; Crow M. K., Rheum Dis Clin N Am, 2010), can be studied in human pDCs. For this purpose, as described above, human PBMCs were isolated from whole blood and the plasmacytoid DCs (pDCs) were isolated therefrom with the aid of a commercially available cell separation kit (Miltenyi Biotech, Plasmacytoid Dendritic Cell Isolation Kit II, Cat. No. 130-097-415) The pDCs thus obtained were resuspended in complete medium (RPMI 1640+GlutaMax [Gibco, Cat. No. 61870-010] supplemented with 10% FBS [Gibco, Cat. No. 10493-106] and 50 U penicillin/streptomycin [Gibco, Cat. No. 15140-114]) and plated out in a cell density of $5 \times 10^4$ cells/well in a 96-well microtitre plate (Costar, Cat. No. 3599). The compounds of the general formula (I) were subjected to serial dilution in a constant volume of 100% DMSO and used in the assay at 9 different concentrations in the range from 10 µM to 1 nM. It was ensured here that the DMSO concentration present was always 0.1% DMSO for each of the 9 concentrations used. There was a 30-minute preincubation of the pDCs with the compounds of the general formula (I). The pDCs were stimulated either with a TLR7/8 ligand (imiquimod, R837, Invivogen, Cat. No. tlrl-imq) or with a TLR9 ligand (CPG-A, ODN2216, Invivogen, Cat. No. tlrl-2216-1) and this led to activation of the IRAK-4-mediated signalling pathways. After incubation for 24 hours, the cell culture supernatants were removed and analysed by means of a commercially available human IFN-α ELISA (IFNalpha Multi-Subtype ELISA Kit, pbl Assay Science, Cat. No. 41105-1). The results of the inhibition of IFN-α in human plasmacytoid DCs are shown by way of example for Example Compound 12 in FIG. 3A and FIG. 3B.

In Vivo Model of TLR-Mediated Inflammation

Figure 4A:
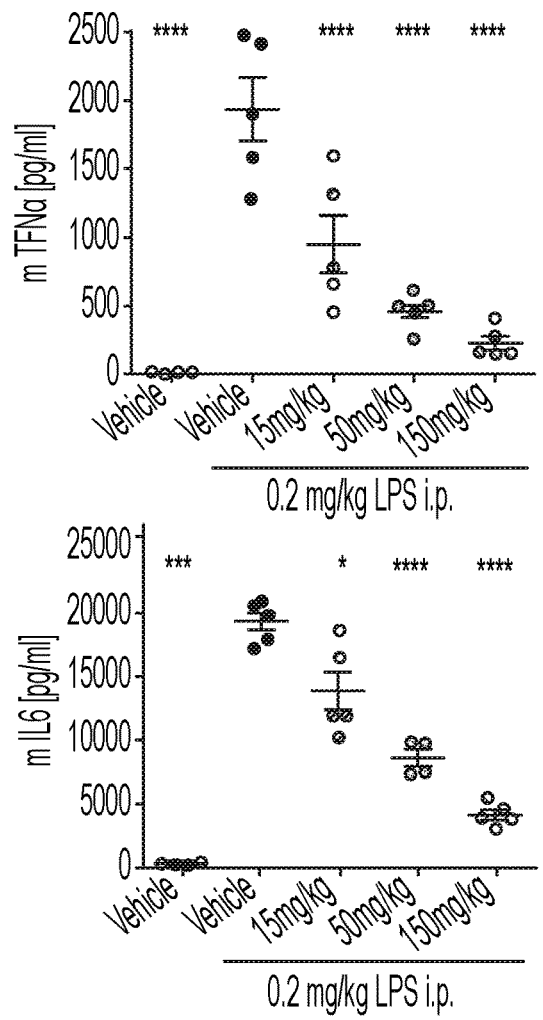
FIG. 4A: Treatment of an LPS-induced inflammation with Example Compound 12 leads to a reduced amount of secreted TNFα and IL-6 in the plasma of the mice. Data is shown as mean values with standard deviations. Single-factor ANOVA variance analysis with subsequent multiple comparative analysis with the LPS control group by means of Dunnett's test: *$p<0.05$; $p<0.01$; *$p<0.001$; ****$p<0.0001$.
Figure 4B:
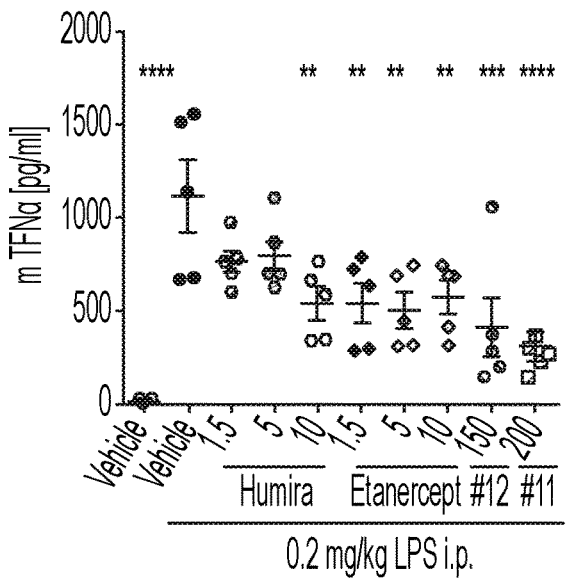
FIG. 4B: Inhibition of TNFα by Example Compound 11 and 12 is in this case comparable to clinically relevant TNF-antagonists [adalimumab (Humira®), etanercept]. Data is shown as mean values with standard deviations. Single-factor ANOVA variance analysis with subsequent multiple comparative analysis with the LPS control group by means of Dunnett's test: *$p<0.05$; *$p<0.01$; *$p<0.001$; **$p<0.0001$.
Figure 5A:
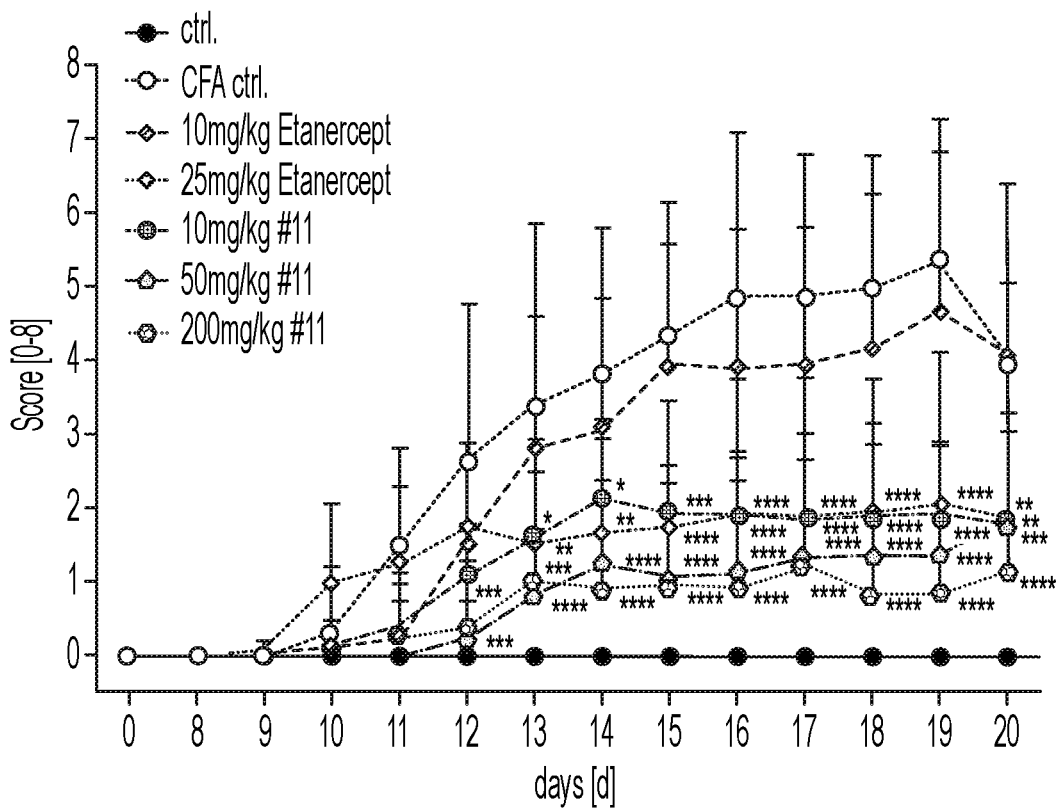
FIG. 5A: Anti-inflammatory effects of Example Compound 11 in an animal model of arthritis (adjuvant-induced rat model). Significant and dose-dependent inhibition of arthritic joint inflammation after prophylactic (from day 0) treatment is shown in comparison to the clinically relevant comparative substance etanercept. The data corresponds to the mean values + standard deviations. Single-factor ANOVA variance analysis with subsequent multiple comparative analysis with the CFA control group by means of Dunnett's test: *$p<0.05$; $p<0.01$; *$p<0.001$; ****$p<0.0001$. Abbreviations: "Score" means disease activity score: "days" means days after induction of arthritis; Etanerc.—etanercept: ctrl.—healthy control: CFA ctrl.—arthritis control.
Figure 5B:
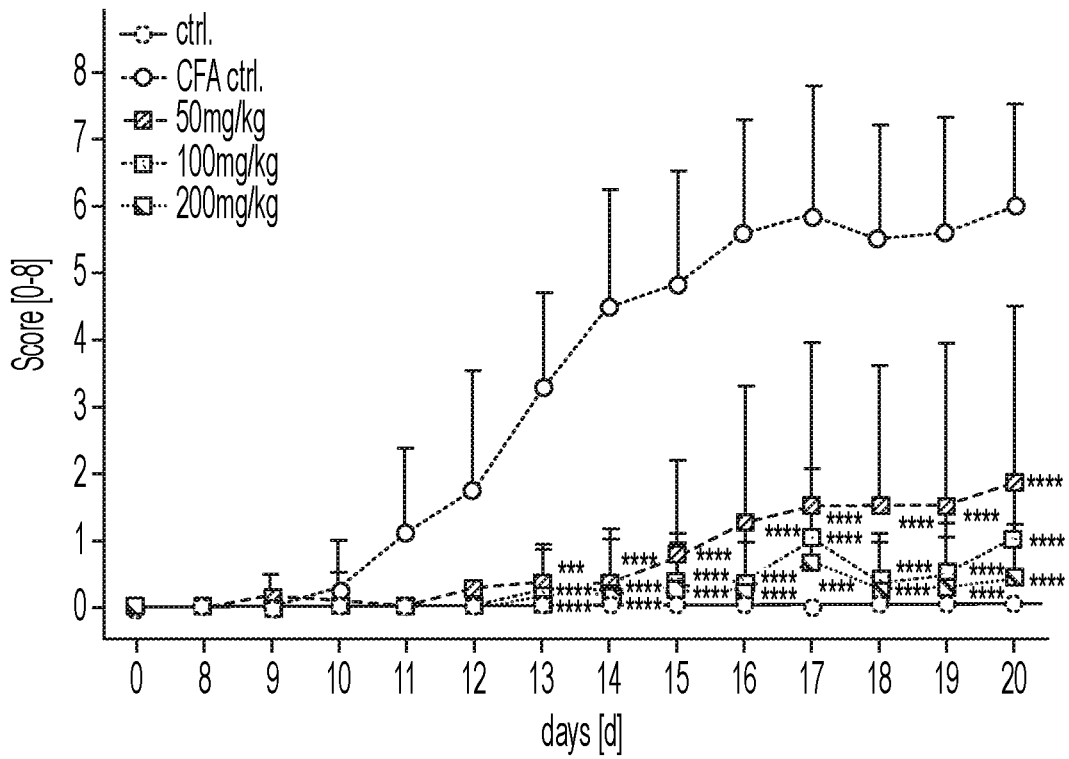
FIG. 5B: Anti-inflammatory effects of Example Compound 11 in an animal model of arthritis (adjuvant-induced rat model). Significant and dose-dependent inhibition of arthritic joint inflammation after therapeutic treatment (<day 9) was measured using the Disease Activity Scores. The data corresponds to the mean values + standard deviations. Single-factor ANOVA variance analysis with subsequent multiple comparative analysis with the CFA control group by means of Dunnett's test: *$p<0.05$; $p<0.01$; *$p<0.001$; ****$p<0.0001$. Abbreviations: "Score" means disease activity score; "days" means days after induction of arthritis; Etanerc.—etanercept; ctrl.—healthy control; CFA ctrl.—arthritis control.
Figure 5C:
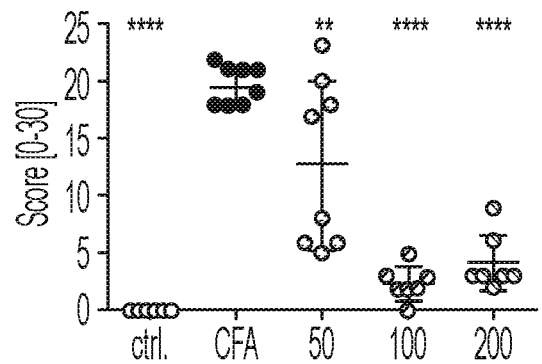
FIG. 5C: Anti-inflammatory effects of Example Compound 11 in an animal model of arthritis (adjuvant-induced rat model). Histopathological analysis of the joints after preventative treatment by means of haematoxylin/eosin staining confirmed significant and dose-dependent inhibition of arthritic joint inflammation. The data corresponds to the mean values + standard deviations. Single-factor ANOVA variance analysis with subsequent multiple comparative analysis with the CFA control group by means of Dunnett's test: *$p<0.05$; $p<0.01$: *$p<0.001$; ****$p<0.0001$ Abbreviations: "Score" means "Histopathology Score".
Figure 5D:
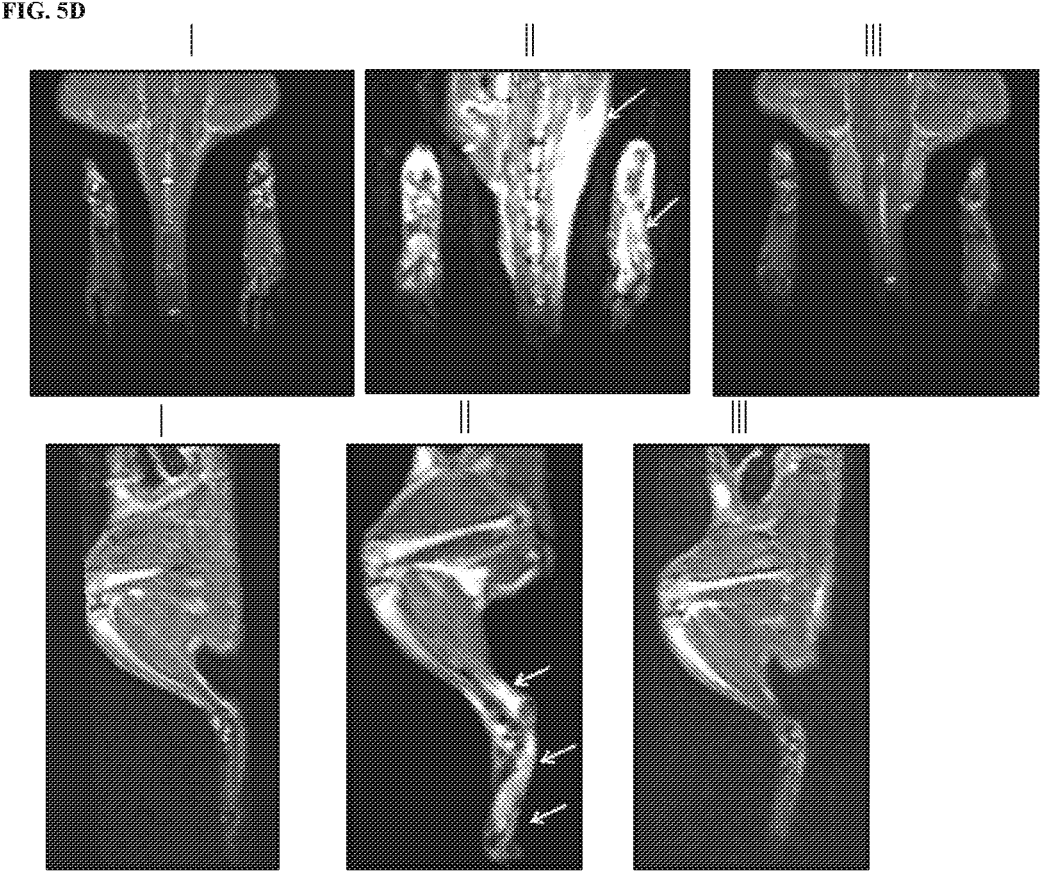
FIG. 5D: Anti-inflammatory effects of Example Compound 11 in an animal model of arthritis (adjuvant-induced rat model). The imaging process by MRI (magnetic resonance imaging) confirme significant and dose-dependent inhibition of arthritic joint inflammation. The data corresponds to the mean values + standard deviations. Single-factor ANOVA variance analysis with subsequen multiple comparative analysis with the CFA control group by means of Dunnett's test; *$p<0.05$; $p<0.01$; $p<0.001$; *$p<0.0001$. Abbreviations: I=ctrl. (healthy control); II=CFA ctrl (arthritis control); III=CFA+200mg/kg#11 (treatment with IRAK4 inhibitor example 11**).
Figure 5E:
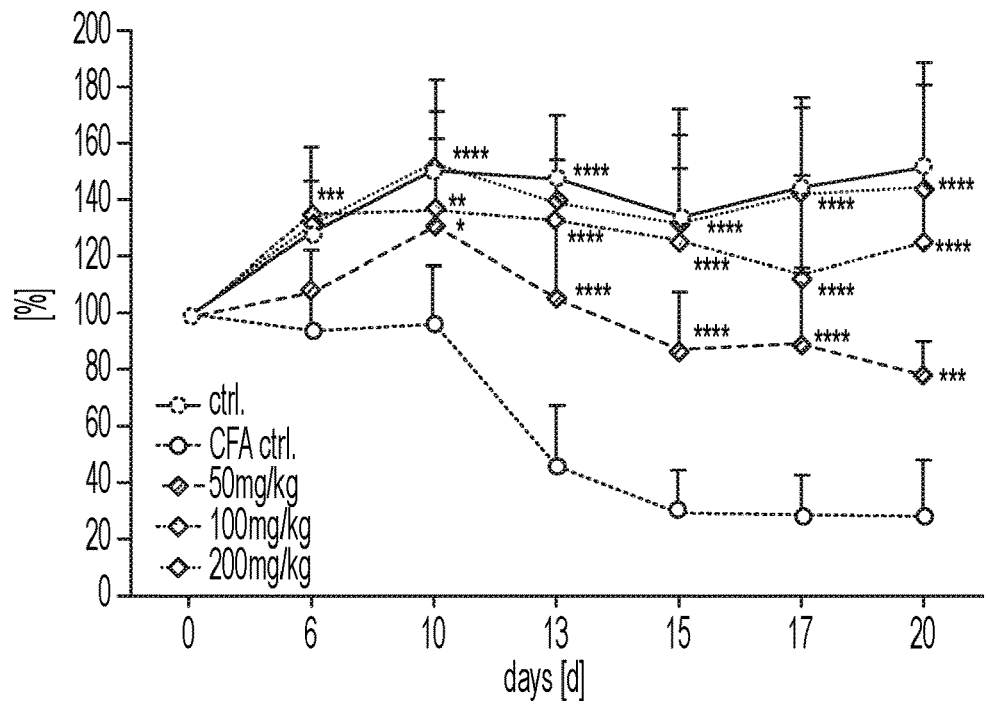
FIG. 5E: Anti-inflammatory effects of Example Compound 11 in an animal model of arthritis (adjuvant-induced rat model). Marked inhibition of hyperalgesia, measured via the grip strength of the mice, was observed during the course of the experiments. The data corresponds to the mean values + standard deviations. Single-factor ANOVA variance analysis with subsequent multiple comparative analysis with the CFA control group by means of Dunnett's test; *$p<0.05$; *$p<0.01$; *$p<0.001$: **$p<0.0001$.Abbreviations: "%" means grip strength; "days" means days after induction of arthritis.
Figure 5F:
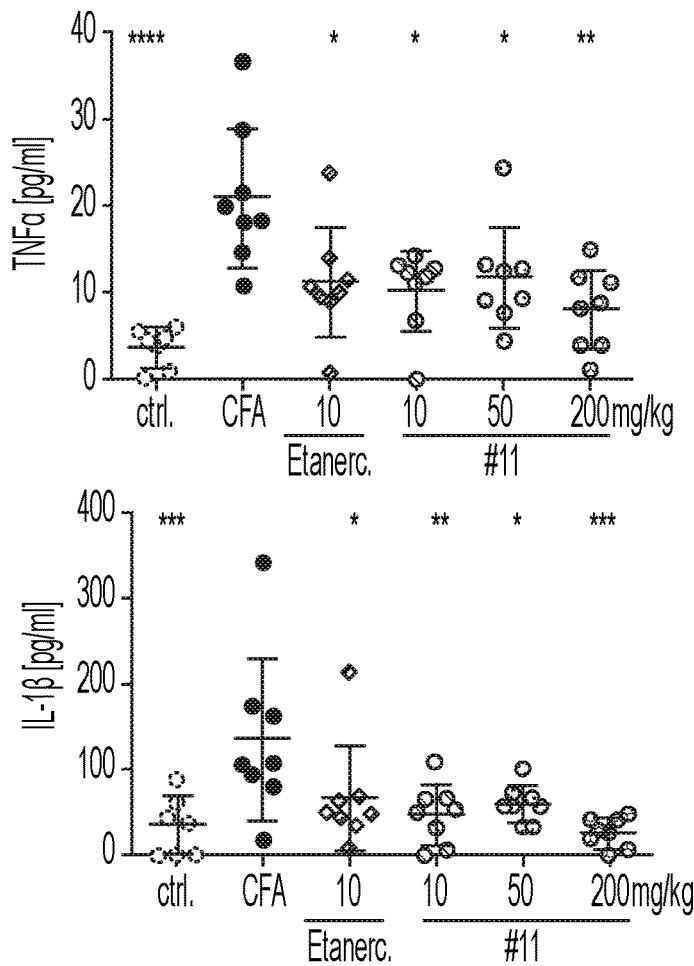
FIG. 5F: Anti-inflammatory effects of Example Compound 11 in an animal model of arthritis (adjuvant-induced rat model). Ex vivo analyses of the synovial fluid showed significant inhibition of cytokine concentrations by treatment with Example Compound 11. The data corresponds to the mean values + standard deviations. Single-factor ANOVA variance analysis with subsequent multiple comparative analysis with the CFA control group by means of Dunnett's test: *$p<0.05$; $p<0.01$; *$p<0.001$; ****$p<0.0001$.
Figure 5G:
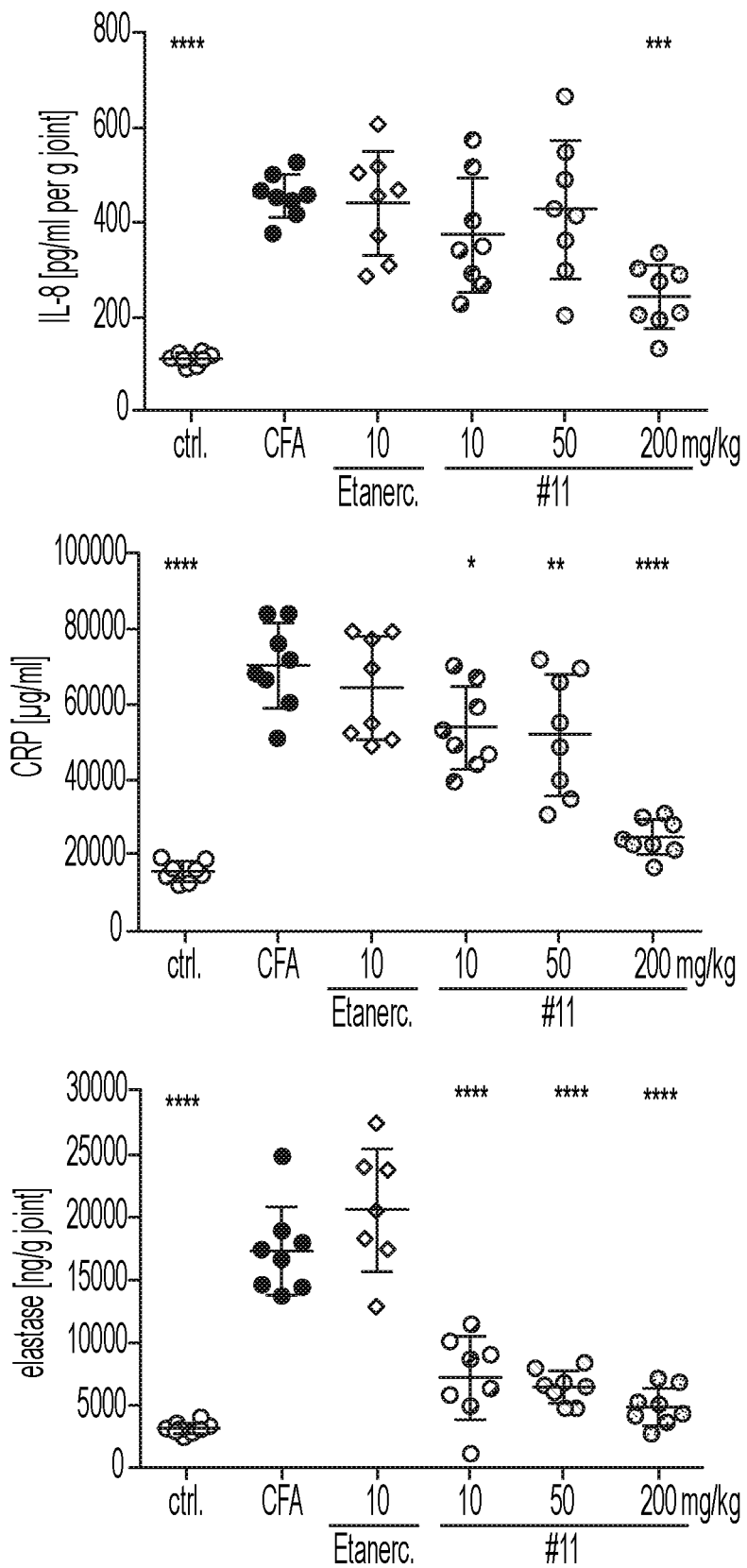
FIG. 5G: Anti-inflammatory effects of Example Compound 11 in an animal model of arthritis (adjuvant-induced rat model). Ex vivo analyses of the arthritic hind paws showed significant inhibition of cytokine concentrations by treatment with Example Compound 11. The data corresponds to the mean values + standard deviations. Single-factor ANOVA variance analysis with subsequent multiple comparative analysis with the CFA control group by means of Dunnett's test: *$p<0.05$; $p<0.01$; *$p<0.001$; ****$p<0.0001$.

The compounds of the general formula (I) were examined for their in vivo efficacy in a model of in vivo TLR-mediated inflammation. This mechanistic model particularly shows the potential effect of the compounds of the general formula (I) on TLR4-mediated disorders, since an LPS-mediated inflammation model was used. In this model, female NMRI mice (about 6 weeks old; Charles River Laboratories, Germany) were divided into groups of 5 animals each. The healthy control group was treated with the vehicle (ethanol-peanut oil 10:90 v/v) in which the substance had been dissolved (substance vehicle) and also with the vehicle in which the LPS had been dissolved. As well as the substrate treatment groups, the positive control group was also administered intraperitoneally (i.p.) with 0.2 mg in each case of LPS/kg body weight (Sigma, Cat. No. L4391) (lipopolysaccharides from E. coli 0111:B4). In addition, the positive control group was treated with the substance vehicle described above. The substance was administered orally 1 hour before induction of inflammation by administration of LPS. To examine the effect of the compounds of the general formula (I) on the inflammation, a final blood sample was taken from the animals after 1.5 hours. The concentration of the cytokines TNF-α and IL-6 in the plasma was determined using the mouse TNF-α and mouse IL-6 Ready-SET-Go ELISA Kits (eBioscience, mTNFα Cat. No. 88-7324-88, mIL-6 Cat. No. 88-7064-88) in accordance with the manufacturer's instructions. IRAK4 inhibitors are effective in the TLR-mediated inflammation model. Application of LPS leads to a rapid induction of proinflammatory cytokines such as TNF-α and IL-6 in the plasma, which is inhibited in a dose-dependent manner by treatment with the compounds of the general formula (I). This is shown by way of example for Compound 12 and 11 in FIG. 4A and FIG. 4B. In some experiments, clinically relevant comparative substances were also tested in the animal model for comparison of inhibitory effectiveness, such as, for example the TNF antagonists adalimumab (Humira®) or etanercept, both of which were in each case administered subcutaneously 1 h prior to induction of the inflammation with LPS at dosages of 1.5 mg/kg, 5 mg/kg and 10 mg/kg.

In Vivo Adjuvant-Induced Arthritis Model

To determine the anti-inflammatory activity of the compounds of the general formula (I), they were examined for their in vivo efficacy in an arthritis model. For this purpose, male Lewis rats (about 100-125 g, Charles River Laboratories, Germany) were each administered subcutaneously with 100 µl of a complete Freund's adjuvant (CFA) solution (*M. tuberculosis* H37Ra [Difo Lab, Cat. No.-231141] dissolved in Incomplete Freund's adjuvant [Difco Lab, Cat. No.-263910]) into the tailhead on day 0. There were n=8 rats in each group. Both a healthy control group and a disease control group were included in the study. Each control group was given p.o. treatment only with the vehicle (Cremophor-ethanol-water 40:10:50 v/v/v) of the test substance either in a preventative manner (from day 0) or in a therapeutic manner (from day 9). The treatment with different dosages of the test substance likewise started either in a preventative manner or in a therapeutic manner by oral application. On day 0, the starting condition of the animals was determined beforehand in terms of the disease activity scores (rating of the severity of arthritis based on a points system). In this points system (score), according to the extent of joint inflammation, points were awarded from 0 to 4 for the presence of an erythema including joint swelling (0=none; 1=slight; 2=moderate; 3=distinct; 4=severe) for both hind paws and added up. To determine the anti-inflammatory efficacy of the compounds, the disease status of the animals was scored by means of disease activity scoring starting from day 8, when the animals first exhibit signs of arthritis, and subsequently 3 times per week, until the end (day 20). In addition, during the course of the experiment, the grip strength of the animals was determined as a measure for hyperalgesia using an automatic grip strength test meter (IITC Life Science Inc., USA). As a measure for joint swelling, the volume of the paws was measured, too, via plethysometer (IITC Life Science Inc., USA) as a measure for joint swelling. On day 20, the experiment was terminated and a magnetic resonance imaging scan was carried out in the MRT (magnetic resonance tomograph; MAGNETOM Avanto syngo MR B17, Siemens, Germany) under inhalative anaesthesia (isoflurane) using the MRT sequence STIR (short-tau inversion recovery for fat signal suppression and for the detection of oedema) as imaging method for analysing the degree of severity of the arthritis. Furthermore, inter alia, the synovial fluid was obtained from the arthritic joints by intraarticular rinsing of the knee joint with 150 µl of sterile saline and examined for the cytokine concentrations present using a commercial multiplex ELISA instrument from Meso Scale Discovery (MSD) (proinflammatory panel 1; Cat. No. K15059D-1). Knee joint biopsies were then used for analysing cytokine concentrations (by multiplex-ELISA from MSD) or CRP levels (rat C-reactive protein, Cat. No. 557825, BD Bioscience) or elastase activity (as a measure for neutrophile infiltration) in the tissue or examined histopathologically for symptoms of inflammation in the synovia and in the intra- and periarticular tissue. To this end, knee joint biopsies were pulverized in a cooled bead mill at −196° C. (CryoMill; Retsch GmBH, Germany), in each case 200 mg were dissolved in the appropriate buffer for cytokine analyses (in 0.5 ml of RPMI1640 medium, Gibco) or for elastase activity (in 1 ml of homogenate buffer [pH 7.0; storage room temperature; 5 g of 5% hexadecyltrimethylammonium bromide, 2.09 g of 10 mM MOPS, add 900 ml of aqua bidest at 30-35° ]). For the quantification of the protease activity of neutrophile elastase (NE), a fluorescent-labelled substrate [MeOSuc-AAPV-AMC (N-methoxysuccinyl-Ala-Ala-Pro-Val-7-amino-4-methylcoumarin), Cat. No. 1-1270, Bachem, Germany] with high specificity for NE (Castillo et al., 1979; Wiesner et al., 2005) was used. Recombinant murine NE (Cat. No. 4517-SE-010, R&D Systems, Germany; dissolved in homogenate buffer, see above) was used as standard curve, and the homogenate buffer as blank value. For the elastase assay, in each case 25 µl of joint homogenate were used and pipetted into a black 96-well microtitter plate (flat bottom, NUNC, Germany) and then mixed with 25 µl of a 1 mM MeOSuc-AAPV-AMC substrate solution in cold TrisBSA buffer (0.1% BSA [fraction V], 0.1 M tris(hydroxymethyl)aminomethane, 1 M NaCl in 1 litre of water; pH 8.5; storage at 4° C.). Using a pre-warmed plate reader (SpectraMax M2, Molecular Devices) the fluorescence in the microtitter plate was measured after 30 min at 37° C. and $\lambda_{Ex}$=380 nm and $\lambda_{Em}$=460 nm, and the amount of neutrophil elastase was calculated using the NE standard curve by means of the software SoftmaxPro 6.4. For the histopathological assessment, in turn, a score was used which, depending on the extent of the damage of the respective parameter in question (inflammation, cartilage damage, synovial hyperplasia, pannus, bone damage, periosteal changes), awards points from 0 to 4 (0=none; 1=slight; 2=moderate; 3=significant; 4=massive) for the presence or the severity of the pathological joint damage. Statistical analysis was effected using single-factor variance analysis (ANOVA) and comparison with the control group by means of multiple comparative analysis (Dunnett's test).

The s.c. administration of CFA in rats leads to acute arthritis with distinct joint inflammation in rats. In an exemplary manner, this rat arthritis model represents joint inflammation in cases of human arthritides such as psoriatic arthritis, rheumatoid arthritis, reactive arthritis and Bechterew disease (Bendele, J Musculoskel Neuron Interact 2001; McCann et al., Arthritis Res Ther, 2010). By preventative, but also therapeutic, treatment with the Example Compound 11, it was possible to markedly inhibit the adjuvant-induced arthritis, and the histological and MRI data in particular indicate a disease modifying action like that of a DMARD (disease-modifying antirheumatic drug). This is illustrated by FIG. 5A, FIG. 5B, FIG. 5C, FIG. 5D, FIG. 5E, FIG. 5G, FIG. 5F, and FIG. 5G. In some experiments, the clinically relevant comparative substance, i.e. the TNF antagonist etanercept (10 mg/kg or 25 mg/kg from day 0), which was administered subcutaneously every third day, was also tested in the animal model for comparison of the inhibitory effectiveness.

In Vivo Collagen Antibody-Induced Arthritis Model in Mice

The anti-inflammatory effect of the compounds of the general formula (I) was examined in a further murine arthritis model. For this purpose, female Balb/c mice (about 9 weeks old, Charles River Laboratories, Kingston, Canada) were each injected intravenously on day 0 with 200 µl of a collagen antibody cocktail (10 mg/ml; ArthritoMab, MD Bioproducts) into the tail vein (except for the healthy control group included in the study). On day 6, these mice then each received a further intraperitoneal injection of 200 µl of LPS. There were n=10 mice in each group. Both a healthy control group and a disease control group were included in the study. Each control group was given p.o. treatment only with the vehicle (ethanol:peanut oil 10:90 v/v) of the test substance in a preventative manner (i.e. from day 0) or in a therapeutic manner (from day 9). The treatment with different dosages of the test substance likewise started in a preventative manner or in a therapeutic manner by oral administration. Over the course of the experiment, the extent of disease was scored on the basis of the points award system for the disease activity score on all four paws. In this awarding of points, no points are awarded for a healthy paw, whereas points from 1 [mild inflammation, for example, of the toe(s)] to 4 [severe inflammation extending over the entire paw] are awarded in each case for the particular extent of joint inflammation that has arisen from the toes through the metatarsal joint to the ankle joint, as explained as follows:

0=normal
1=erythema and mild swelling limited to the tarsal or ankle or toes
2=erythema and mild swelling extending from the ankle to the metatarsus (2 segments)
3=erythema and moderate swelling extending from the ankle as far as the metatarsal joints
4=erythema and severe swelling encompassing the metatarsus, foot and toes.

At the same time, in the course of the experiment, the paw volume was measured via plethysometer (IITC Life Science Inc., USA) as a measure of the joint swelling. For this parameter, the starting condition was determined beforehand in each case one day before the start of the experiment (day −1) and the disease activity score and the paw volume were subsequently scored three times per week from day 8 onwards. On day 21, the experiment was terminated and knee joint biopsies were examined for histopathological analyses of inflammation symptoms in the synovia and in the intra- and periarticular tissue. For the histopathological assessment, likewise, a score was used which, depending on the extent of the damage of the respective parameter in question (inflammation, cartilage damage, synovial hyperplasia, pannus, bone damage, periosteal changes), awards points from 0 to 4 (0=none; 1=slight; 2=moderate; 3=significant; 4=massive) for the presence or the severity of the pathological joint damage. Statistical analysis was effected using single-factor variance analysis (ANOVA) and comparison with the control group by means of multiple comparative analysis (Dunnett's test).

Figure 6A:
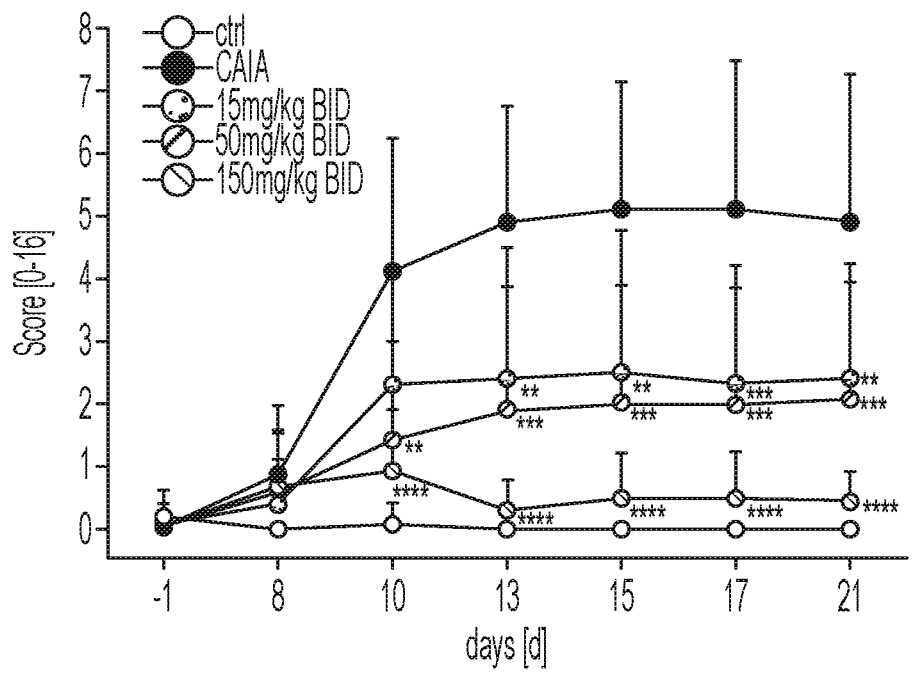
FIG. 6A: Anti-inflammatory effects of Example Compound 12 in an animal model of arthritis (collagen antibody-induced mouse model, CAIA). Significant and dose-dependent inhibition of arthritic joint inflammation after prophylactic (day 0) was measured using the Disease Activity Scores. Inhibition of arthritis by Example Compound 12. The data corresponds to the mean values + standard deviations. The statistical significances between collagen antibody (AK) control and the treatment groups were calculated by means of single-factor ANOVA variance analysis with subsequent multiple comparative analysis (Dunnett's test) (*$p<0.05$; $p<0.01$; *$p<0.001$; ****$p<0.0001$). Abbreviations: "Score" means disease activity score: "days" means days after arthritis induction; ctrl.—healthy control; CAIA—arthritis control.
Figure 6B:
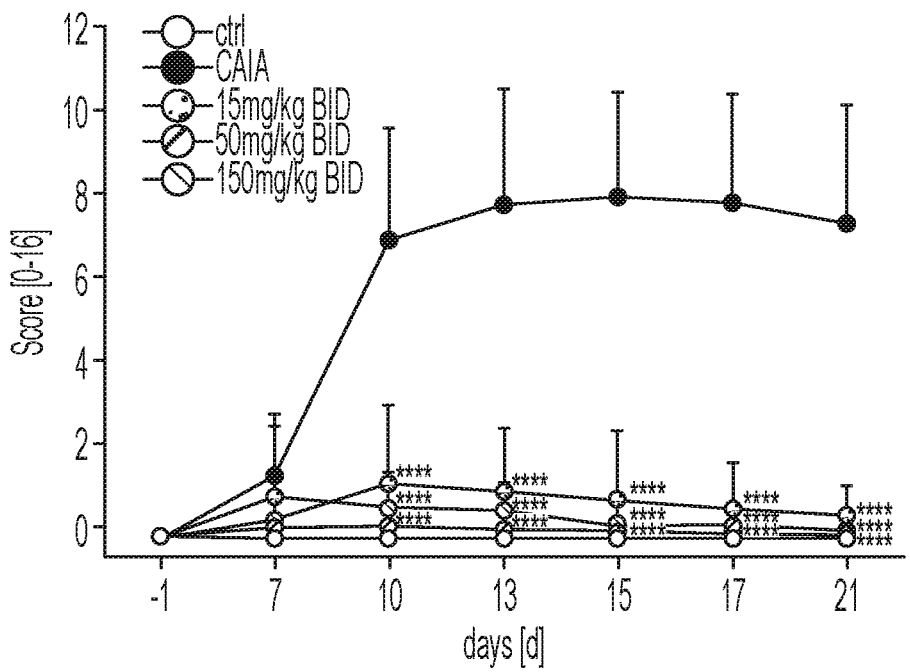
FIG. 6B: Anti-inflammatory effects of Example Compound 12 in an animal model of arthritis (collagen antibody-induced mouse model, CAIA). Significant and dose-dependent inhibition of arthritic joint inflammation after therapeutic treatment (> day 9) was measured using the Disease Activity Scores. Inhibition of arthritis by Example Compound 12. The data corresponds to the mean values + standard deviations. The statistical significances between collagen antibody (AK) control and the treatment groups were calculated by means of single-factor ANOVA variance analysis with subsequent multiple comparative analysis (Dunnett's test) (*$p<0.05$; $p<0.01$; *$p<0.001$; ****$p<0.0001$). Abbreviations: "Score" means disease activity score; "days" means days after arthritis induction; ctrl.—healthy control; CAIA—arthritis control.
Figure 6C:
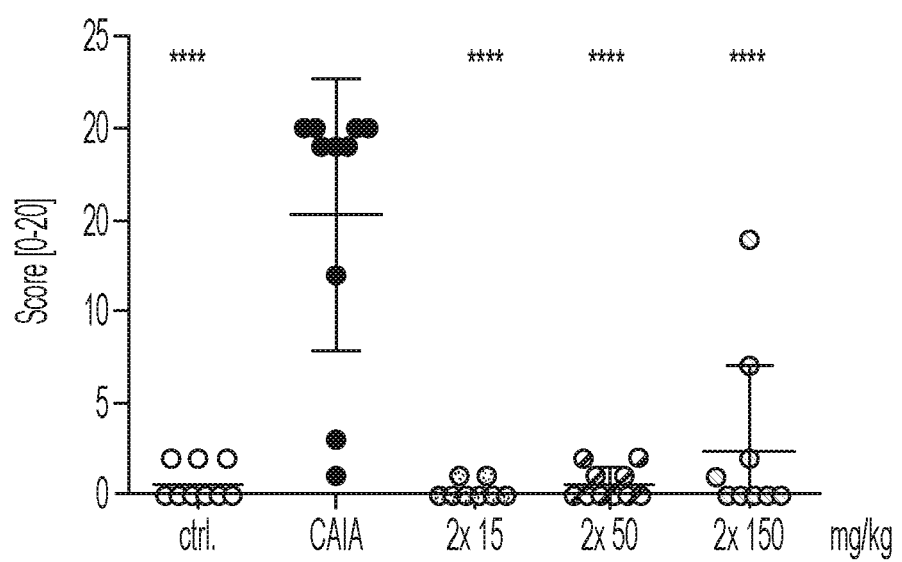
FIG. 6C: Anti-inflammatory effects of Example Compound 12 in an animal model of arthritis (collagen antibody-induced mouse model, CAIA). Histopathological analysis of the arthritic joints by haematoxylin/eosin staining confirmed the anti-inflammatory activity after therapeutic treatment. Inhibition of arthritis by Example Compound 12. The data corresponds to the mean values + standard deviations. The statistical significances between collagen antibody (AK) control and the treatment groups were calculated by means of single-factor ANOVA variance analysis with subsequent multiple comparative analysis (Dunnett's test) (*$p<0.05$; $p<0.01$; *$p<0.001$; ****$p<0.0001$). Abbreviations: "Score" means "histopathology score".
Figure 7A:
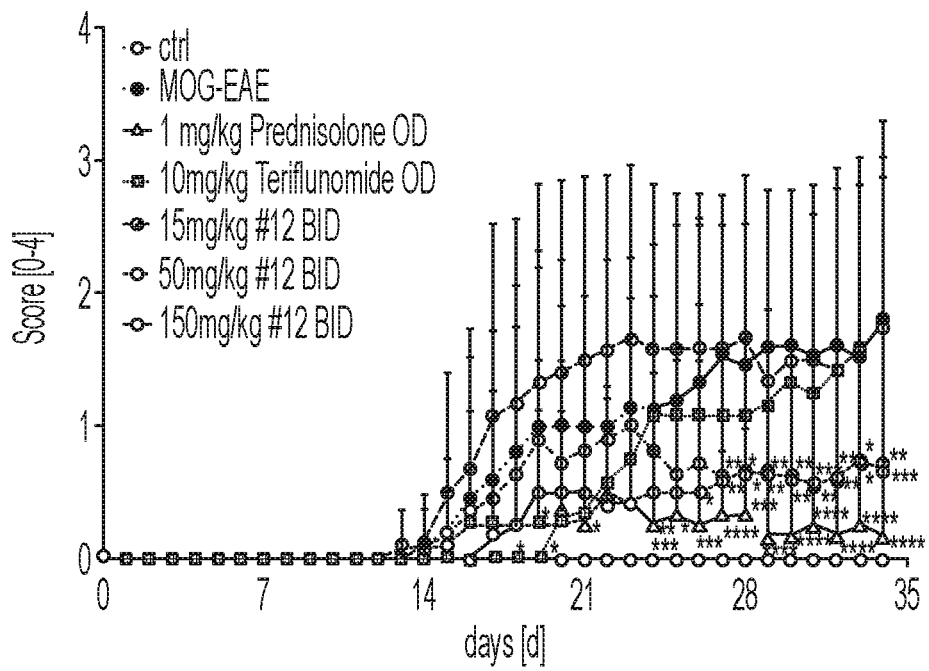
FIG. 7A: Anti-inflammatory action of the Example Compound 12 in an animal model of multiple sclerosis (MOG$_{33-35}$-induced EAE mouse model) in comparison to trifluonomide and prednisolone. Significanr and dose-dependent inhibition of the clinical severity of the disorder (EAE disease activity score) was assessed by neuroaxial degeneration (degeneration, neuroaxonal, white matter) and lymphocyte infiltration into the white matter (infiltrate, lymphohitiocytic, white matter) or into the grey matter (cortex, infiltrate, lumphohitiocytic, grey matter) after treatment with Compound 12. The data corresponds to mean value + standatd deviations. The statistical significances between MOG-EAE control and the treatment groups were calculated by the means of a single-factor ANOVA variance analysis with subsequent multiple comparative analysis (Dunnett's test) (*$p<0.05$; $p<0.01$; *$p<0.001$; ****$p<0.0001$). Abbreviations: "Score" means EA disease activiy score; "days" means days after EAE introduction; ctrl.—healthy control; MOG-EAE—EAE control.
Figure 7B:
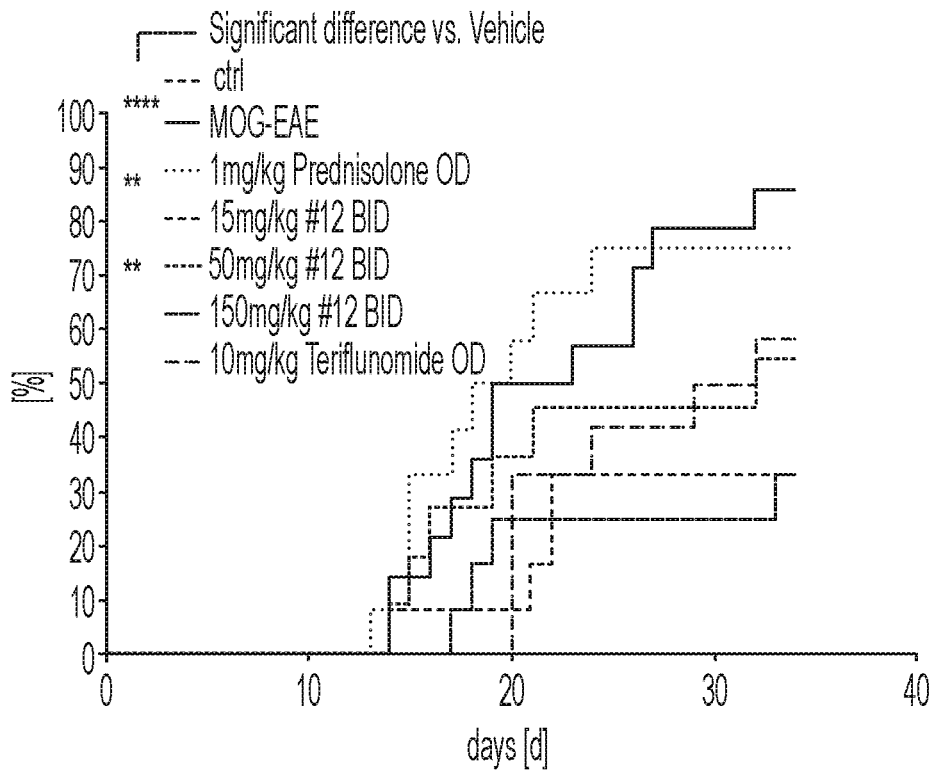
FIG. 7B: Anti-inflammatory action of the Example Compound 12 in an animal model of multiple sclerosis (MOG$_{33-35}$-induced EAE mouse model) in comparison to teriflunomide and prednisolone. Significant and dose-dependent inhibition of the incidence rate of the disorder was assessed by neuroaxial degeneration (degeneration, neuroaxonal, white matter) and lymphocyte infiltration into the white matter (infiltrate, lymphohitiocytic, white matter) or into the grey matter (cortex; infiltrate, lymphohitiocytic, grey matter) after treatment with Compound 12. The data correspond to mean valued + standard deviations. The statistical significances beterrn MOG-EAE control and the treatment groups were calculated by means of single-factor ANOVA variance analysis with subsequent multiple comparative analysis (Dunnett's test) (*$p<0.05$; $p<0.01$;*$p<0.001$; ****$p<0.0001$). Abbreviations: „%" means EAE disease prevalance; „days "means days after EAE induction.
Figure 7C:
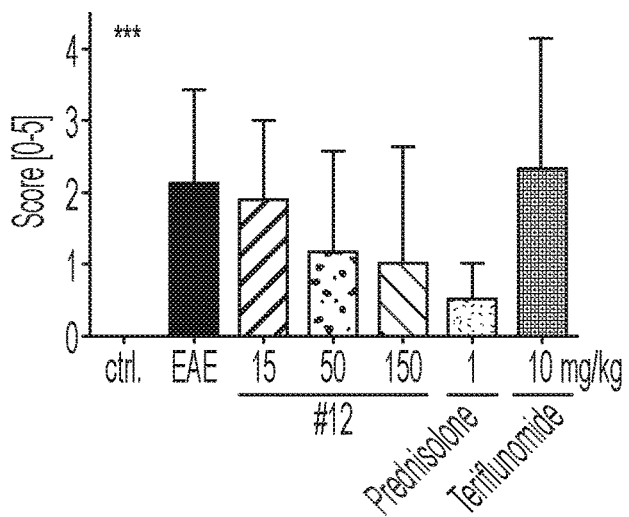
FIG. 7C: Anti-inflammatory action of the Example Compound 12 in an animal model of multiple sclerosis (MOG$_{33-35}$-induced EAE mouse model) in comparison to teriflunomide and prednisolone. Significant and dose-dependent inhibition of the histopathological damage of the spinal marrow was assessed by neuroaxial degeneration in the white matter after treatment with Compound 12. The data correspond to mean values + standard deviations. The statistical significances between MOG-EAE control and the treatment groups were calculated by means of single-factor ANOVA variance analysis with subsequent multiple comparative analysis (Dunnett's test) (*$p<0.05$; $p<0.01$ ;*$p<0.001$; ****$p<0.0001$). Abbreviations: "Score"means histopathological score with respect to neuroaxonal degeneration in the white matter.
Figure 7D:
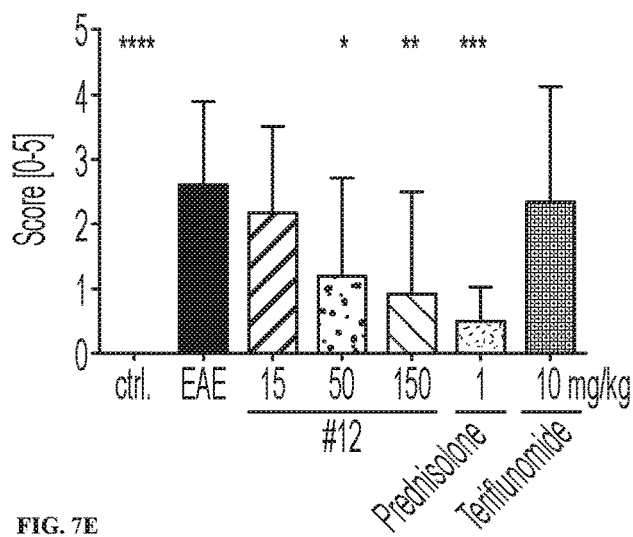
FIG. 7D: Anti-inflammatory action of the Example Compound 12 in an animal model of multiple sclerosis (MOG$_{33-35}$-induced EAE mouse model) in comparison to teriflunomide and prednisolone. Significant and dose-dependent inhibition of the histopathological damage of the spinal marrow was assessed by lymphocyte infiltration into the white matter (infiltrate, lymphohitiocytic, white matter) after treatment with Compound 12. The data correspond to mean values + standard deviations. The statistical significances between MOG-EAE control and the treatment groups were calculated by means of single-factor ANOVA variance analysis with subsequent multiple comparative analysis (Dunnett's test) (*$p<0.05$; $p<0.01$ ;*$p<0.001$; ****$p<0.0001$). Abbreviations: "Score" means histopathological score with respect to lymphohistiocytic infiltrates in the white matter.
Figure 7E:
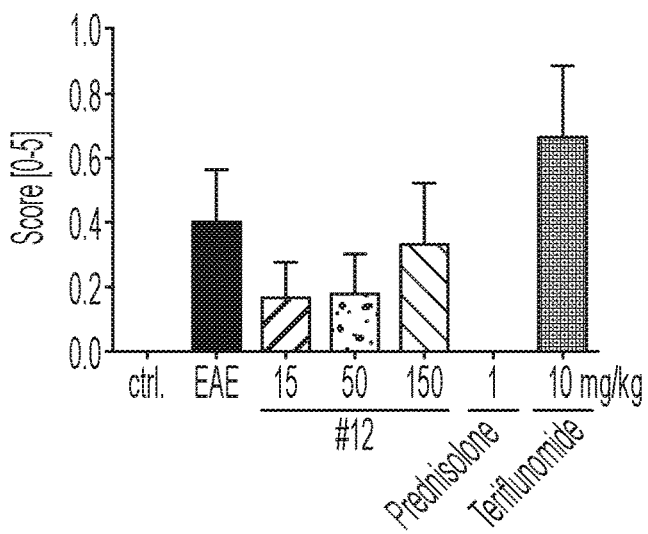
FIG. 7E: Anti-inflammatory action of the Example Compound 12 in an animal model of multiple sclerosis (MOG$_{33-35}$-induced EAE mouse model) in comparison to teriflunomide and prednisolone. Significant and dose-dependent inhibition of the histopathological damage of the spinal marrow was assessed by lymphocyte infiltration into the grey matter (cortex; infiltrate, lymphohitiocytic, grey matter) after treatment with Compound 12. The data correspond to mean values + standard deviations. The statistical significances between MOG-EAE control and the treatment groups were calculated by means of single-factor ANOVA variance analysis with subsequent multiple comparative analysis (Dunnett's test) (*p<0.05; p<0.01;*p<0.001; ****p<0.0001). Abbreviations: "Score" means histopathological score with respect to lymphohistiocytic infiltrates in the grey matter.

The i.v. administration of a collagen antibody cocktail including the subsequent i.p. administration of LPS in mice leads to acute arthritis with distinct joint inflammation in mice (Holmdahl et al., APMIS 1989; McCann et al., Arthritis Res Ther, 2010) and thus represents a further animal model for the arthritic indications psoriatic arthritis, rheumatoid arthritis, reactive arthritis and Bechterew disease. By preventative, but also therapeutic, treatment with the Example Compound 12, it was possible to markedly inhibit this collagen antibody-induced arthritis, and the histopathological data of the hind paw joints indicate disease-modifying action. This is illustrated by FIG. 6A, FIG. 6B, and FIG. 6C.

In Vivo $MOG_{33-35}$-Induced Chronic EAE (Experimental Autoimmune Encephalomyelitis) Model in the Mouse To determine the anti-inflammatory activity of the compounds of the general formula (I), these were examined in an experimental animal model of multiple sclerosis (MS) for their in vivo efficacy. The chronic $MOG_{33-35}$ (myelin oligodendrocyte glycoprotein)-induced EAE (experimental autoimmune encephalomyelitis) model is the standard animal model for testing pharmacological substances for potential use in MS patients. To this end, female C57BL/6 mice (19-20 g; Jackson Laboratories, Bar Harbor, USA) were randomized and used at a group strength of 10 to 15 animals per group. Using a subcutaneous injection of in each case 0.1 ml of solution comprising 200 g of $MOG_{33-35}$ peptide emulsified in 100 µl of CFA (complete freund adjuvant; 2 mg/ml) supplemented with *Mycobacterium tuberculosis* (MT; 8 mg/ml, strain H37RA), on day 0 the EAE disorder was induced with additional intraperitoneal administration (day 0 and day 2) of 200 ng of pertussis toxin (PTx; dissolved in 0.1 ml of PBS (2 µg/ml)), and its progression was monitored over 34 days. The experiment also comprised both a healthy control group and a disease control group, both of which had been treated p.o. with the vehicle (ethanol:peanut oil 10:90 v/v) of the Example Compound 12. Instead, the treatment groups received different daily doses of the Example Compound 12 as preventative therapy, i.e. from day 0, by oral administration. Parameters such as incidence rate and symptoms of an EAE were checked daily. Here, the EAE symptoms were scored using a point system which represents the degree of severity of the disorder (EAE disease activity score):

0=normal, healthy
1=limp/paralysed mouse tail
2=limp/paralysed mouse tail and weakness in the hind paws
3=limp/paralysed mouse tail and complete paralysis of the hind paws
4=paralysed tail, complete paralysis of the hind paws and partial paralysis of the front paws
5=complete paralysis of all front and hind paws, euthanasia On day 34 after EAE induction, the experiment was terminated and, inter alia, blood was withdrawn from the mice for subsequent biomarker analysis, and spinal marrow was withdrawn for histopathological assessment of neuroaxial degeneration and lymphocyte infiltration. For the histopathological assessment of the degree of severity of the disorder, the spinal marrow was stained with haematoxylin, eosin and luxol fast blue, and neuroaxial degeneration, lymphocyte infiltration into the white matter and lymphocyte infiltration into the grey matter was then scored blind using a point system (0=normal, no findings; 1=minimal findings; 2=slight findings; 3=moderate findings; 4=significant findings; 5=severe findings). The statistical analysis was carried out using the monofactorial variance analysis ANOVA and the comparison with the control group by multiple comparative analysis (Dunnett test). By treatment with the Example Compound 12, it was possible to inhibit induced EAE, an experimental model for MS. Here, the example compound was comparable or even superior to the efficacy of a steroid (prednisolone; 1 mg/kg daily p.o. from day 0) or teriflunomide (Aubagio®; 10 mg/kg daily p.o. from day 0) which were also tested in the experiment as clinical comparative substances. This is illustrated in FIG. 7A, FIG. 7B, FIG. 7C, FIG. 7D, and FIG. 7E.

In Vivo Imiquimod-Induced Psoriasis Model in the Mouse

The compounds of the general formula (I) were examined for their anti-inflammatory effects in an animal model of psoriasis. In mice, topical administration of imiquimod (IMQ) a TLR7/8 ligand and potent immune activator, leads to a psoriasis-like phenotype on the skin. Thus, over 7 days, each day 3.5 mg of imiquimod (equivalent to 70 mg of 5% Aldara® cream, Meda AB) were applied topically to mice onto the skin of the back, which had been shaved beforehand, and to both ears (outside). A healthy control group, which was also tested, received paraffin oil instead. Subsequently, the IMQ disease control, like the healthy control group, were treated preventatively, i.e. from day 0, orally (p.o.) daily with the vehicle (Solutol HS15-water (40/60 v/v)) of the test compound. The daily p.o. treatment with different dosages of the test compound was also initiated on day 0. In each case, the group size was n=10 animals. During the experiment, the manifestation of the psoriasis was assessed visually every day by means of a point system using the clinical scores described below:

| Score | Erythema | Flaking | Thickness of the skin (back) |
|---|---|---|---|
| 0 | none | none | normal |
| 1 | slight | slight | slight |
| 2 | moderate | moderate | moderate |
| 3 | marked | marked | marked |
| 4 | considerable | considerable | considerable |

Parallel thereto, every day the skin of the back and both ears was measured with respect to thickness and/or formation of oedema using a digital caliper (Kutimeter; Horex Digital Caliper, Helios-Preisser, Germany). Every 2 days, the body weight of each mouse was checked. On day 7, the experiment was terminated and, after the animals had been sacrificed, the skin of the back and the ears were fixed in formalin for subsequent histopathological assessment. This histopathological assessment of the ear and the skin of the back after haematoxylin/eosin staining of the paraffin skin sections (2 μm) in a microtome (Leica, Germany) was carried out by a pathologist, in blinded form. Here, the following aspects were examined and assessed for their degree of severity by means of a point system (for each parameter examined): parakeratosis (impaired cornification characterized by cell nuclei or cell nuclei residues remaining in the horny layer)/hyperkeratosis (excessive cornification of the skin) and infiltration of immune cells into the dermis or epidermis. Here, each histological parameter examined was assessed as follows:

0=normal
1=slight change
2=moderate change
3=significant change

Figure 8A:
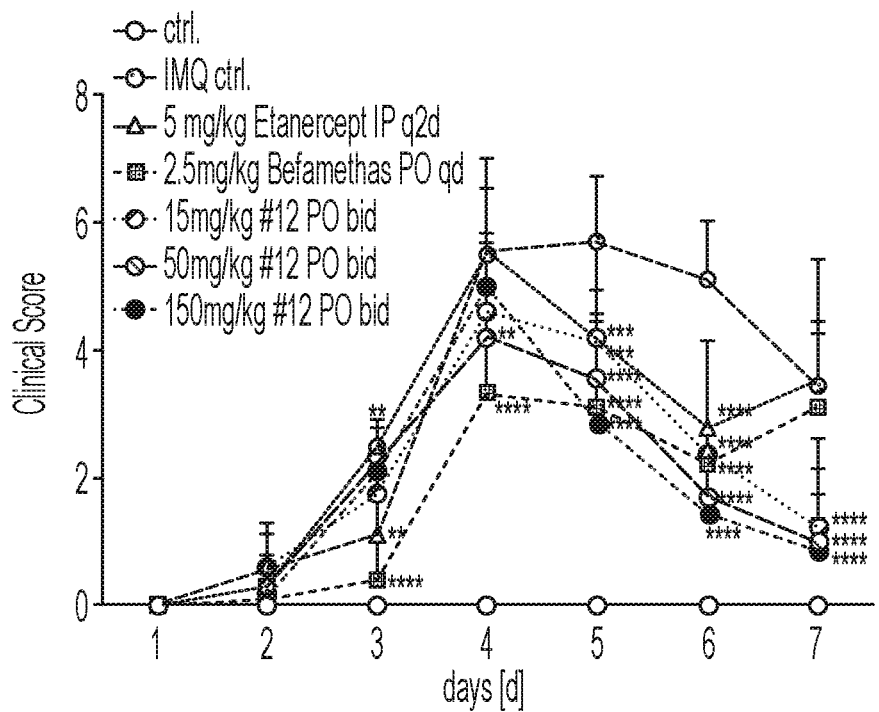
FIG. 8A: The anti-inflammatory action of Example Compound 12 in an animal model of the psoriasis (IMQ-induced mouse model). Significant inhibition of the clinical score was used to assesses the pathological parameters parakeratosis, inflammation and exocytosis. The data correspond to the mean values + standard deviations. The statistical significances between IMQ control and the treatment groups were calculated by means of single-factor ANOVA variance analysis with subsequent multiple comparative analysis (Dunnett's test) (*p<0.05; p<0.01;*p <0.001; ****p<0.0001). Abbreviations: Etanerc.—etanercept; Betameth—betamethasone; po—per oral: ip—intraperitoneal injection; bid—twice daily; q2d—every other day.
Figure 8B:
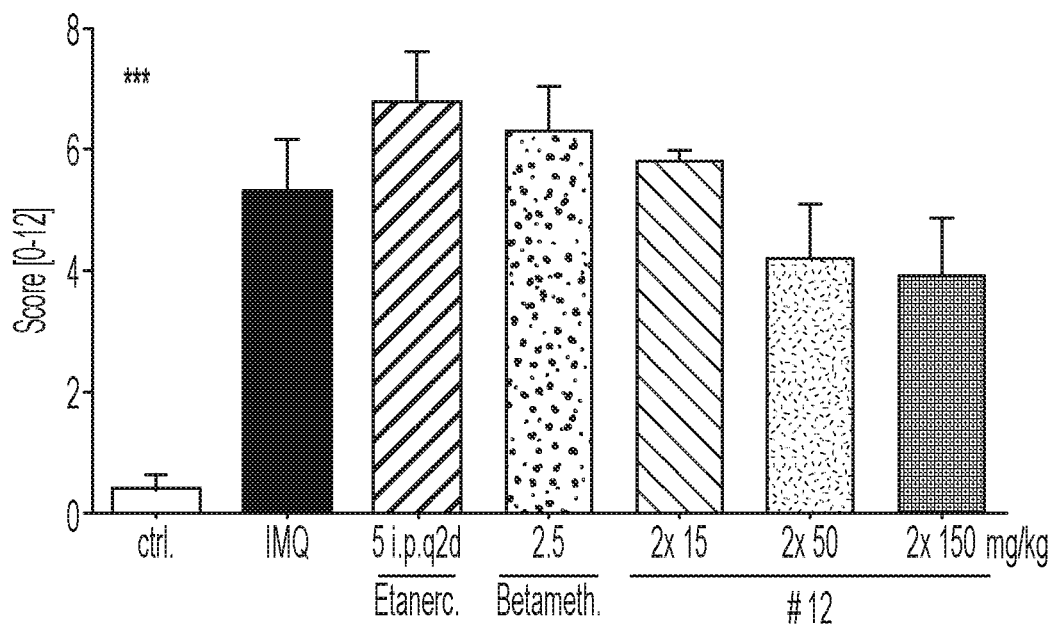
FIG. 8B: The anti-inflammatory action of Example Compound 12 in an animal model of the psoriasis (IMQ-induced mouse model). Significant inhibition of the clinical symptoms erythema, flaking and thickness of the skin on the back and of the histopathological assessment of the ears was used to assess assesses the pathological parameters parakeratosis, inflammation and exocytosis. The data correspond to the mean values + standard deviations. The statistical significances between IMQ control and the treatment groups were calculated by means of single-factor ANOVA variance analysis with subsequent multiple comparative analysis (Dunnett's test) (*p<0.05; p<0.01 ;*p <0.001; ****p<0.0001). Abbreviations: Etanerc.—etanercept; Betameth—betamethasone; po—per oral: ip—intraperitoneal injection; bid—twice daily: q2d—every other day.
Figure 8C:
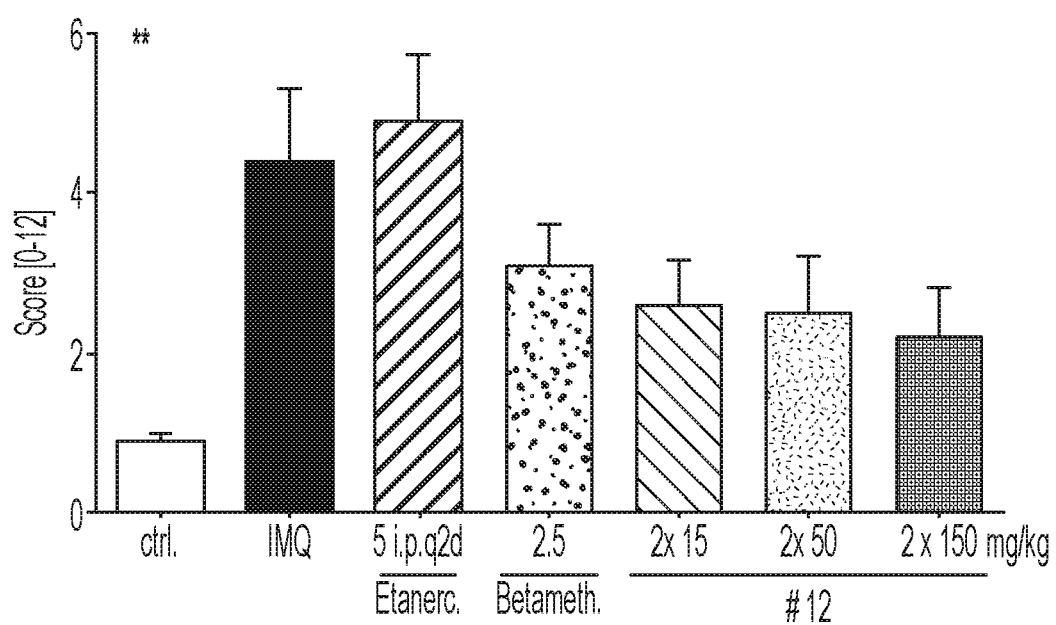
FIG. 8C: The anti-inflammatory action of Example Compound 12 in an animal model of the psoriasis (IMQ-induced mouse model). Significant inhibition of the histopathological assessment of the skin of the back was used to assess the pathological parameters parakeratosis, inflammation and exocytosis. The data correspond to the mean values + standard deviations. The statistical significances between IMQ control and the treatment groups were calculated by means of single- factor ANOVA variance analysis with subsequent multiple comparative analysis (Dunnett's test) (*p<0.05; p<0.01;*p<0.001; ****p<0.0001). Abbreviations: Etanerc.—etanercept; Betameth —betamethasone; po—per oral; ip—intraperitoneal injection; bid—twice daily; q2d—every other day.

All histological parameters were then added up and represented as a total histology score. In addition, the thickness of the epidermis in the skin section was measured. The IMQ-mediated skin inflammation in the mouse represents an animal model for the indication psoriasis or for the skin phenotype in psoriatic arthritis (van der Fits et al., J Immunol 2009). By treatment with the Example Compound 12, it was possible to inhibit induced psoriasis. Here, the example compound was comparable or even superior to the efficacy of a steroid (Betamethasone, Celestene®; 2.5 mg/kg daily p.o.) or of a TNF antagonist (etanercept; 5 mg/kg every other day i.p.), which were also tested in the experiment, as clinical comparative substances. This is illustrated by FIG. 8A, FIG. 8B, and FIG. 8C.

In Vivo DNFB-Induced Skin Inflammation Model in the Mouse

The model of the DNFB (2,4-dinitro-1-fluorobenzene)-induced allergic contact dermatitis (contact allergy) in the mouse represents an inflammatory skin disorder with the background of an immune reaction of the delayed type (delayed-type hypersensitivity; DTH) mainly mediated by T-helper lymphocytes of type 1 (Th1 cells). This Th1-mediated inflammatory reaction of the skin represents an example of the inflammatory processes during psoriasis, psoriatic arthritis and allergic contact eczema (Roese et al., Exp Dermatol. 2012). For triggering the skin inflammations, female NMRI mice (22-24 g, Charles River, Germany) were sensitized beforehand, on day 0 and day 1, on the shaved skin of the back (area about 10 cm$^2$) using in each case 25 μl of a 0.5% strength (w/v) DNFB solution (2,4-dinitrofluorobenzene, Cat. No. 70-34-8, Sigma Aldrich, Germany; dissolved in acetone/olive oil; 4/1; v/v). In each case, the group size was n=10 mice. The skin inflammation was then triggered on day 5 by topical application of in each case 20 μl of a 0.3% strength (w/v) DNFB solution (in acetone/olive oil; 4/1; v/v) to the outside of both ears (area per ear about 2 cm$^2$). Both a healthy control group ("sensitization and triggering" only with the solvent acetone/olive oil [4/1; v/v]), a disease control group (sensitization and triggering with DNFB) and an irritation control (sensitisation only with solvent, triggering with DNFB) were also tested in the experiment. These control groups were only treated, 1 h prior to triggering the skin inflammation, with the vehicle (ethanol:peanut oil, 10:90 v/v) of the test substance, p.o., the treatment groups received the appropriate dosage of the test substance, likewise orally. On day 6 (24 hours after triggering the inflammation), the ear thickness was determined individually for each ear using a digital caliper, and the weight of the ears of each mouse was determined. By subsequent analyses in ear homogenates obtained by homogenization (automatic homogenizer produced by Feinmechanik-Werkstatt, Bayer AG, Germany) of the ears in 1.5 ml of homogenate buffer for 20 see with subsequent centrifugation (15 000 rpm; 12° C., 20 min) and removal of the supernatants, it was possible to determine, inter alia, elastase activity as a measure for the infiltration of neutrophils into the inflamed tissue. In order to quantify the protease activity of neutrophil elastase (NE), a fluorescently labelled substrate (MeOSuc-AAPV-AMC; Cat. No. I-1270, Bachem, Germany), which is highly specific for NE (Castillo et al., 1979; Wiesner et al., 2005), was used. Here, recombinant murine NE (Cat. No. 4517-Se-010, R&D Systems, Germany; dissolved in homogenate buffer) was used as standard curve and the homogenate buffer was used as blank value. For the elastase assay, in each case 25 μl of ear homogenate were used and pipetted into a black 96-well microtiter plate (flat bottom, NUNC, Germany) and then mixed with 25 μl of a 1 mM MeOSuc-AAPV-AMC substrate solution in cold TrisBSA buffer. Using a prewarmed plate reader (Spectra-Max M2, Molecular Devices) the fluorescence in the microtiter plate was measured after 30 min at 37° C. and $\lambda_{Ex}$=380 nm and $\lambda_{Em}$=460 nm and the amount of neutrophil elastase was calculated with the software SoftmaxPro 6.4, using the NE standard curve.

Figure 9:
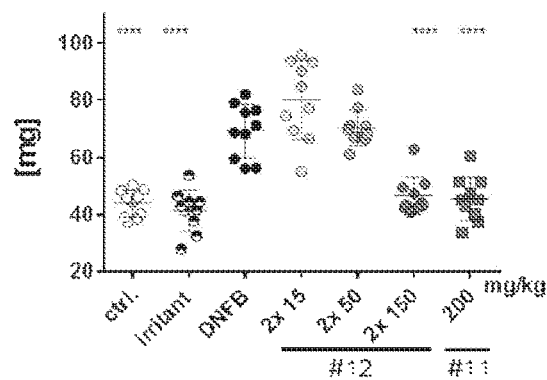
FIG. 9: Anti-inflammatory effects of Example Compound 12 in an animal model of TH1-mediated skin inflammation (DNFB-induced skin inflammation model in the mouse). Significant and dose-dependent inhibition of the skin inflammation as evidenced by the ear weight (in mg), which correlates with oedema formation during the inflammation. The statistical significances between DNFB-control and the treatment groups were calculated by means of single-factor ANOVA variance analysis with subsequent multiple comparative analysis (Dunnett's test) (*p<0.05; p<0.01; *p<0.001; ****p<0.0001). Abbreviations: "mg" on the y-axis means ear weight; ctrl—healthy control; irritant—irritation control.

By treatment with the Example Compound 11 and the Example Compound 12, it was possible to inhibit the ThH1-mediated skin inflammation triggered by DNFB. This is shown in FIG. 9.

In Vivo TMA-Induced Skin Inflammation Model in the Mouse

Figure 10:
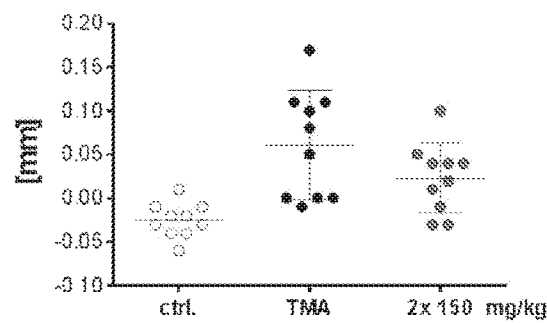
FIG. 10: Anti-inflammatory effects of Example Compound 12 in an animal model of TH2-mediated skin inflammation (TMA-induced skin inflammation model in the mouse). Inhibition of skin inflammation shown as an increase of ear thickness (delta [delta] ear thickness in mm) in comparison to baselines. An increased ear thickness is seen as a measure for the inflammation and represents oedema formation in the ear tissue during the inflammation reaction. Abbreviations: "mm" on the y-axis means the change (delta) in ear weight; ctrl—healthy control.

The model of the TMA (trimellitic anhydride)-induced allergic contact dermatitis (contact allergy) in the mouse represents an inflammatory skin disorder with the background of an immune reaction of the delayed type (delayed-type hypersensitivity; DTH) mainly mediated by eosinophils and T-helper lymphocytes of type 2 (THh2 cells). This Th2-mediated inflammatory reaction of the skin represents an example of the inflammatory processes during atopic dermatitis and during contact allergy (Sur et al., BMC Complement Altern Med. 2015). For triggering the skin inflammations, female NMRI mice (22-24 g, Charles River, Germany) were sensitized beforehand, on day 0, on the shaved skin of the back (area about 10 cm²) using in each case 50 µl of a 3% strength (w/v) TMA solution (Cat. No. 552-30-7, Sigma Aldrich, Germany; dissolved in acetone/isopropyl myristate; 4/1; v/v). In each case, the group size was n=10 mice. The skin inflammation was then triggered on day 5 by topical application of in each case 10 µl of a 3% strength (w/v) TMA solution (in acetone/isopropyl myristate; 4/1; v/v) to the outside of both ears (area per ear about 2 cm²). Both a healthy control group ("sensitization and triggering" only with the solvent acetone/isopropyl myristate [4/1; v/v]) and a disease control group (sensitization and triggering with TMA) were also tested in the experiment. Whereas these control groups were only treated, 1 h prior to triggering the skin inflammation, with the vehicle (ethanol:peanut oil 10:90 v/v) of the test substance, p.o., the treatment groups received the appropriate dosage of the test substance, likewise orally. On day 6 (24 hours after triggering the inflammation) the ear thickness was determined individually for each ear using a digital caliper, and the weight of the ears of each mouse was determined. By subsequent analyses in ear homogenates, which can be obtained as described above, it is possible to determine, inter alia, elastase activity as a measure for the infiltration of neutrophils into inflamed tissue, as described above (under "DNFB-induced skin model"). By treatment with the Example Compound 12, it was possible to inhibit the Th2-mediated skin inflammation, triggered by TMA. This is shown in FIG. 10 using the parameter ear thickness (delta ear thickness=ear thickness day 6 minus original ear thickness), which represents oedema formation during the course of the inflammation.

In Vivo DSS-Induced Colitis Model in the Mouse

Figure 12:
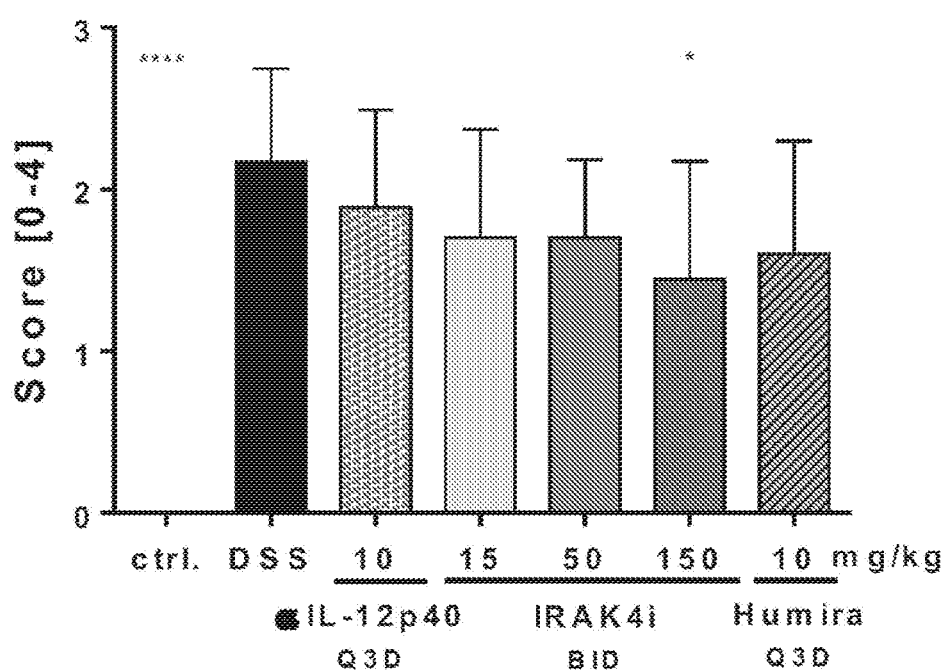
FIG. 12: Anti-inflammatory effect of example compound 12 in IBD (Inflammatory Bowel Disease) animal model (DSS-induced colitis in mice). Significant inhibition of bowel inflammation including ulceration, determined by endoscopy on day 16. The endoscopic assessment was made by means of a scoring system with regard to the severity and extent of colon inflammation. The data correspond to the mean values+standard deviations. The statistical significances between DSS control and the treatment groups were calculated by means of single-factor variance analysis ANOVA with subsequent multiple comparative analysis (Dunnet's test) (*p<0.05; p<0.01; *p<0.001; ****p<0.0001). Abbreviations: "Score" means endoscopy score; αIL-12p40—anti-mouse IL-12p40 monoclonal antibody; IRAK4i means IRAK4 inhibitor, example compound 11 here; BID—twice daily; Q3D—every third day.

To determine the anti-inflammatory potential of the compounds of the general formula (I), these compounds are assessed in an animal model of intestinal inflammation, the DSS (dextran sodium sulphate)-induced colitis model. Administration of DSS via the drinking water to susceptible mice leads to the development of an acute intestinal inflammation (colitis) with typical clinical symptoms such as bloody diarrhoea, weight loss, formation of oedema in the colon. It is thus an experimental animal model for IBD (inflammatory bowel disease) which comprises the indications Crohn's disease and ulcerative colitis (Okaysu et al., Gastroenterol, 1990; Dieleman et al., Gastroenterol, 1994). Male C57BL/6 mice (6-8 weeks; Charles River, USA; n=10-12 mice/group) receive, from day 0 up to and including day 5, 3% strength DSS (35-48 kDa; Cat. No. DB001; TDB Consultancy AB, Sweden), daily freshly prepared, via the drinking water for triggering colitis. A healthy control group (n=8 mice), which is also tested, receives normal drinking water instead. In each case, the control groups (healthy control and colitis disease control) are only treated with the vehicle (ethanol:peanut oil 10:90 v/v) of the test substance, p.o. Treatment with the various dosages of the test substance is carried out preventatively, i.e. from day 0, by oral administration with the first DSS dose. Here, during the course of the experiment, body weight and the presence of possibly even bloody diarrhoea (assessment via point system [score] of 0-4 points, where 0=normal shaped stool, 1=soft shaped stool, 2=soft unshaped stool, 3=aqueous stool/diarrhoea, 4=bloody diarrhoea) are assessed daily. Here, occult bloody stool is detected using a haemoccult test (Cat. No. 3060; Beckman Coulter, Germany). In addition, on day 10 and day 16, a video endoscopy (Karl Storz Endoskope, Germany) is carried out under inhalative anaesthesia with isoflurane to assess the severity of the colitis, where the extent of intestinal damage is assessed using a point system (score) of 0 to 4 points, as follows:

0=normal, healthy
1=loss of vascularity
2=loss of vascularity, and friability
3=friability and erosions
4=ulcerations and bleeding After the last endoscopy, the experiment is terminated, blood is removed via the vena cava and the colon is examined for its length and its weight, both of which represent, as indirect markers, a colitis-associated thickening of the intestinal wall which correlates with the severity of the colitis. The intestine (one 2 cm piece each from the distal and the proximal side) is additionally also analysed histopathologically after fixation in formalin by haematoxylin/eosin staining of paraffin sections. Induced DSS colitis in mice, an experimental model for chronic inflammatory bowel disease (IBD), was able to be inhibited by treatment with example compound 12. The efficacy of example compound 12 was comparable to the efficacy of approved biologics (anti-IL-12p40 at 10 mg/kg Q3D [every third day] i.p. from day 0 or anti-TNF Humira® [Adalimumab] at 10 mg/kg Q3D s.c. from day 0), which were included in the experiment as clinically relevant reference substances. This is illustrated in FIG. 12.

In Vivo Pristane-Induced SLE Model in the Mouse

Figure 11:
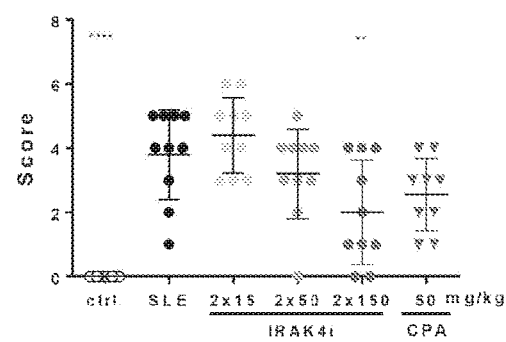
FIG. 11: The anti-inflammatory effect of example compound 12 in the animal model of systemic lupus erythematosus (pristane-induced mouse model). Significant inhibition of kidney damage shown by histopathological assessments of kidneys. The data correspond to the mean values+standard deviations. The statistical significances between SLE control and the treatment groups were calculated by means of single-factor variance analysis ANOVA with subsequent multiple comparative analysis (Dunnet's test) (*p<0.05; p<0.01; *p<0.001; ****p<0.0001). Abbreviations: "Score" means renal histopathology score; IRAK4i means IRAK4 inhibitor, example compound 11 here; CPA—cyclophosphamide; ctrl.—healthy control; 2×—twice daily.

To determine the anti-inflammatory activity of the compounds of the general formula (I), the compounds are assessed in an SLE (systemic lupus erythematosus)-model for their in vivo efficacy. Pristane, a mineral oil (2,6,10,14-tetramethylpentadecane), leads, after injection into mice, to systemic lupus erythematosus with characteristic organ involvement (e.g. nephritis, mild erosive arthritis), typical auto-antibody production, for example anti-double strand (ds) DNA antibodies (Leiss et al., Lupus 2013) and dependency on type 1 interferon (e.g. IFN-alpha) and TLR signals, as described in men (Satoh et al., Proc Natl Acad Sci USA, 1995; Thibault et al., Arthritis Res Ther. 2009; Thibault et al., J Clin Invest. 2008; Wu et al., Acta Pharmacol Sin. 2015; Hagberg and Rönnblom, Scand J Immunol, 2015). Thus, on day 0, in each case 500 µl of pristane (Sigma, Cat. No. 1921-70-6) are administered intraperitoneally to female Balb/c mice (20-22 g, Charles River Laboratories, USA). In each case, the group size is n=10 mice. Both a healthy control group and a disease control group are also tested in the experiment. Both control groups are treated only with the vehicle (ethanol:peanut oil 10:90 v/v) of the test substance, p.o. Treatment with various dosages of the test substance is carried out preventatively, i.e. from day 0, by oral administration about 1 h after the pristane injection. Additionally, on day 0, the baseline of the animals with respect to the protein status in urine (proteinuria measured using Coomassie brilliant blue G 250 with BSA [bovine serum albumine] as reference), the auto-antibody concentration (e.g. anti-dsDNA) and the creatinine values in the serum and the paw volume (using a plethysometer) are determined. During the course of the experiment, these parameters are then monitored: paw volume every week, protein status in the urine and auto-antibodies and creatinine in the serum in week 2, 4 and 6 after pristane injection. Six weeks after triggering of SLE by pristane, the experiment is terminated and the kidneys are fixated in 10% neutral-buffered formalin for histopathological assessment and subsequently 5-µm-paraffin sections are assessed pathologically by staining with haematoxylin and eosin (H&E). Here, the histological findings are assessed and classified using a point system (0=healthy, 1=minimal changes of the kidney tissue, 2=slight changes, 3=moderate changes, 4=marked changes of the kidney tissue). Lupus nephritis as a crucial characteristic in pristane-induced SLE was able to be inhibited by treatment with example compound 12. Example compound 12 was slightly superior to the immunosuppressant cyclophosphamide (50 mg/kg once per week p.o. from day 0), which was included in the experiment as clinical reference substance. This is illustrated in FIG. 11 by the assessment of renal pathology.

In Vivo $PLP_{139-151}$-Induced Relapsing-Remitting EAE Model in the Mouse

To determine the anti-inflammatory potential of the compounds of the general formula (I), these compounds are assessed in a relapsing-remitting animal model of MS for their in vivo efficacy for therapeutic treatment of an acute MS episode or for preventing new episodes. The relapsing-remitting $PLP_{139-151}$ (proteolipid-protein)-induced EAE model is a standard animal model for testing pharmacological substances for potential use in MS patients. For triggering relapsing-remitting EAE, on day 0 on four different sides of the back of the mouse (2 in the upper neck region, 2 in the lower region about 2 cm cranial from the tail base), an emulsion containing $PLP_{139-151}$/CFA (Hooke Kit™ $PLP_{139-151}$/CFA Emulsion; Cat. No. EK-0120; Hooke Laboratories, Lawrence Mass., USA) is injected (0.05 ml/injection site) subcutaneously into female SJL mice (8-10 weeks old, Jackson Laboratories Bar Harbor, USA). A healthy control group (n=5 mice), which is also tested, is not immunized. In addition to this control group, an EAE disease control is also tested in the experiment. During the course of the study, both control groups are treated with the vehicle (ethanol:peanut oil 10:90 v/v) of the test substance p.o. The daily p.o. treatment with different dosages of the test substance or its vehicle is carried out therapeutically during the first episode or after the episode. Here, the therapeutic treatment after onset of EAE (first episode; treatment start day 12) serves to determine the possibility of treating an acute MS episode, whereas the therapeutic treatment with the example compound after the first episode (treatment start day 19) is intended to find out to what extent the test substance can prevent a new episode. In this $PLP_{139-151}$-induced EAE model, first EAE symptoms appear about day 11. From day 9, the clinical EAE symptoms are assessed daily, blinded, assessment being carried out using a point system (score; points from 0=healthy to 5=moribund) which represents the severity of the disorder (same score index as in the MOG-EAE model). Also monitored during the course of the study are body weight and mortality.

The invention claimed is:

1. A method of treating multiple sclerosis, in a subject in need thereof, comprising:
   administering to the subject an effective amount of a compound, wherein the compound is:
   N-[2-(3-Hydroxy-3-methylbutyl)-6-(2-hydroxypropan-2-yl)-2H-indazol-5-yl]-6-(trifluoromethyl)pyridine-2-carboxamide; or
   N-{6-(2-Hydroxypropan-2-yl)-2-[2-(methylsulphonyl)ethyl]-2H-indazol-5-yl}-6-(trifluoromethyl)pyridine-2-carboxamide,
   or a pharmaceutically acceptable salt thereof.

2. The method of claim 1, wherein the compound is N-[2-(3-Hydroxy-3-methylbutyl)-6-(2-hydroxypropan-2-yl)-2H-indazol-5-yl]-6-(trifluoromethyl)pyridine-2-carboxamide, or a pharmaceutically acceptable salt thereof.

3. The method of claim 1, wherein the compound is N-{6-(2-Hydroxypropan-2-yl)-2-[2-(methylsulphonyl)ethyl]-2H-indazol-5-yl}-6-(trifluoromethyl)pyridine-2-carboxamide, or a pharmaceutically acceptable salt thereof.

4. The method of claim 1, wherein the subject is a human subject.

5. The method of claim 1, wherein the subject is an animal subject.

6. A method of treating pain in a subject in need thereof, comprising:
   administering to the subject an effective amount of a compound, wherein the compound is:
   N-[2-(3-Hydroxy-3-methylbutyl)-6-(2-hydroxypropan-2-yl)-2H-indazol-5-yl]-6-(trifluoromethyl)pyridine-2-carboxamide; or
   N-{6-(2-Hydroxypropan-2-yl)-2-[2-(methylsulphonyl)ethyl]-2H-indazol-5-yl}-6-(trifluoromethyl)pyridine-2-carboxamide,
   or a pharmaceutically acceptable salt thereof.

7. The method of claim 6, wherein the pain is acute pain, chronic pain, inflammatory pain, or neuropathic pain, or any combination thereof.

8. The method of claim 6, wherein the pain is hyperalgesia, allodynia, or lower back pain, or any combination thereof.

9. The method of claim 6, wherein the compound is N-[2-(3-Hydroxy-3-methylbutyl)-6-(2-hydroxypropan-2-yl)-2H-indazol-5-yl]-6-(trifluoromethyl)pyridine-2-carboxamide, or a pharmaceutically acceptable salt thereof.

10. The method of claim 6, wherein the compound is N-{6-(2-Hydroxypropan-2-yl)-2-[2-(methylsulphonyl)ethyl]-2H-indazol-5-yl}-6-(trifluoromethyl)pyridine-2-carboxamide, or a pharmaceutically acceptable salt thereof.

11. The method of claim 6, wherein the subject is a human subject.

12. The method of claim 6, wherein the subject is an animal.

* * * * *